United States Patent
Hung et al.

(10) Patent No.: US 10,138,453 B2
(45) Date of Patent: *Nov. 27, 2018

(54) CELL CULTURE ARRAY SYSTEM FOR AUTOMATED ASSAYS AND METHODS OF OPERATION AND MANUFACTURE

(71) Applicant: EMD Millipore Corporation, Burlington, MA (US)

(72) Inventors: Paul J. Hung, Berkeley, CA (US); Philip J. Lee, Alameda, CA (US)

(73) Assignee: EMD Millipore Corporation, Burlington, MA (US)

( * ) Notice: Subject to any disclaimer, the term of this patent is extended or adjusted under 35 U.S.C. 154(b) by 203 days.

This patent is subject to a terminal disclaimer.

(21) Appl. No.: 15/163,368

(22) Filed: May 24, 2016

(65) Prior Publication Data

US 2016/0289623 A1   Oct. 6, 2016

Related U.S. Application Data

(63) Continuation of application No. 12/348,907, filed on Jan. 5, 2009, now Pat. No. 9,376,658.

(Continued)

(51) Int. Cl.
*C12M 3/06* (2006.01)
*B01L 3/00* (2006.01)
(Continued)

(52) U.S. Cl.
CPC ......... *C12M 23/16* (2013.01); *B01L 3/50273* (2013.01); *B01L 3/502715* (2013.01);
(Continued)

(58) Field of Classification Search
CPC ...... C12M 23/16; C12M 23/12; C12M 41/48; C12M 29/10; B01L 3/50273;
(Continued)

(56) References Cited

U.S. PATENT DOCUMENTS 4,055,613 A   10/1977   Kapral
4,661,455 A   4/1987    Hubbard
(Continued)

FOREIGN PATENT DOCUMENTS

CN   201803927 U   4/2011
DE   19948087 A1   5/2001
(Continued)

OTHER PUBLICATIONS

Office action dated Feb. 20, 2018 in co-pending U.S. Appl. No. 15/163,398.
(Continued)

*Primary Examiner* — Michael L Hobbs
(74) *Attorney, Agent, or Firm* — Nields, Lemack & Frame, LLC

(57) ABSTRACT

A number of novel improved microfluidic configurations and systems and methods of manufacture and operation. In one embodiment, three wells are used for independent cell culture systems in a cell culture array. In a second aspect, artificial sinusoids with artificial epithelial barriers are provided with just one (optionally shared or multiplexed) fluidic inlet and one (optionally shared or multiplexed) fluidic output, where the medium output also functions as a cellular input. A pneumatic cell loader combined with other components provides a fully automated cell culture system. Magnetic alignment of plate molds provides advantages and ease of molded manufacture.

15 Claims, 38 Drawing Sheets

24 Unit Array Plate

Single Flow Unit

Culture Chamber

Related U.S. Application Data

(60) Provisional application No. 61/037,297, filed on Mar. 17, 2008, provisional application No. 61/018,882, filed on Jan. 3, 2008.

(51) Int. Cl.
     *C12M 1/32*     (2006.01)
     *C12M 1/00*     (2006.01)
     *C12M 1/36*     (2006.01)
     *G01N 35/00*     (2006.01)

(52) U.S. Cl.
     CPC ........ *B01L 3/502761* (2013.01); *C12M 23/12* (2013.01); *C12M 29/10* (2013.01); *C12M 41/48* (2013.01); *G01N 35/00029* (2013.01); *G01N 35/0099* (2013.01); *B01L 3/5025* (2013.01); *B01L 3/5027* (2013.01); *B01L 2300/0829* (2013.01); *B01L 2300/0848* (2013.01); *B01L 2300/0861* (2013.01); *B01L 2400/0457* (2013.01); *B01L 2400/0487* (2013.01); *G01N 2035/00148* (2013.01)

(58) Field of Classification Search
     CPC ......... B01L 3/502715; B01L 3/502761; B01L 3/5025; B01L 3/5027; B01L 2300/0861; B01L 2300/0829; B01L 2400/0861; B01L 2400/0487; G01N 35/0029; G01N 35/0099; B01N 2035/00148
     See application file for complete search history.

(56) References Cited

U.S. PATENT DOCUMENTS

| | | |
|---|---|---|
| 4,734,373 A | 3/1988 | Bartal |
| 4,748,124 A | 5/1988 | Vogler |
| 5,079,168 A | 1/1992 | Amiot |
| 5,153,131 A | 10/1992 | Wolf et al. |
| 5,310,676 A | 5/1994 | Johansson et al. |
| 5,330,908 A | 7/1994 | Spaulding |
| 5,376,252 A | 12/1994 | Ekstrom et al. |
| 5,416,022 A | 5/1995 | Amiot |
| 5,424,209 A | 6/1995 | Kearney |
| 5,437,998 A | 8/1995 | Schwarz et al. |
| 5,451,524 A | 9/1995 | Coble et al. |
| 5,462,874 A | 10/1995 | Wolf et al. |
| 5,565,353 A | 10/1996 | Klebe et al. |
| 5,589,112 A | 12/1996 | Spaulding |
| 5,593,814 A | 1/1997 | Matsuda et al. |
| 5,602,028 A | 2/1997 | Minchinton |
| 5,627,070 A | 5/1997 | Gruenberg |
| 5,637,469 A | 6/1997 | Wilding et al. |
| 5,641,644 A | 6/1997 | Klebe |
| 5,658,797 A | 8/1997 | Bader |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,714,384 A | 2/1998 | Wilson et al. |
| 5,763,261 A | 6/1998 | Gruenberg |
| 5,763,275 A | 6/1998 | Nagels et al. |
| 5,763,279 A | 6/1998 | Schwarz et al. |
| 5,786,215 A | 7/1998 | Brown et al. |
| 5,793,440 A | 8/1998 | Nakasaka et al. |
| 5,801,054 A | 9/1998 | Kiel et al. |
| 5,866,345 A | 2/1999 | Wilding et al. |
| 5,882,918 A | 3/1999 | Goffe |
| 5,900,361 A | 5/1999 | Klebe |
| 5,912,177 A | 6/1999 | Turner et al. |
| 5,924,583 A | 7/1999 | Stevens et al. |
| 5,932,315 A | 8/1999 | Lum et al. |
| 5,942,443 A | 8/1999 | Parce et al. |
| 6,039,897 A | 3/2000 | Lochhead et al. |
| 6,048,498 A | 4/2000 | Kennedy |
| 6,096,532 A | 8/2000 | Armstrong et al. |
| 6,107,085 A | 8/2000 | Coughlin et al. |
| 6,153,073 A | 11/2000 | Dubrow et al. |
| 6,190,913 B1 | 2/2001 | Singh |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,251,343 B1 | 6/2001 | Dubrow et al. |
| 6,274,337 B1 | 8/2001 | Parce et al. |
| 6,277,642 B1 | 8/2001 | Mentzen et al. |
| 6,297,046 B1 | 10/2001 | Smith et al. |
| 6,323,022 B1 | 11/2001 | Chang et al. |
| 6,326,211 B1 | 12/2001 | Anderson et al. |
| 6,403,369 B1 | 6/2002 | Wood |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,481,648 B1 | 11/2002 | Zimmermann |
| 6,495,104 B1 | 12/2002 | Unno et al. |
| 6,518,035 B1 | 2/2003 | Ashby et al. |
| 6,534,013 B1 | 3/2003 | Kennedy |
| 6,548,263 B1 | 4/2003 | Kapur et al. |
| 6,551,841 B1 | 4/2003 | Wilding et al. |
| 6,555,365 B2 | 4/2003 | Barbera-Guillem et al. |
| 6,562,616 B1 | 5/2003 | Toner et al. |
| 6,569,675 B2 | 5/2003 | Wall et al. |
| 6,576,458 B1 | 6/2003 | Sarem et al. |
| 6,585,744 B1 | 7/2003 | Griffith |
| 6,585,939 B1 | 7/2003 | Dapprich et al. |
| 6,593,136 B1 | 7/2003 | Geiss |
| 6,637,463 B1 | 10/2003 | Lei et al. |
| 6,648,015 B1 | 11/2003 | Chow |
| 6,653,124 B1 | 11/2003 | Freeman |
| 6,673,595 B2 | 1/2004 | Barbera-Guillem |
| 6,756,019 B1 | 6/2004 | Dubrow et al. |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,821,772 B2 | 11/2004 | Barbera-Guillem et al. |
| 6,846,668 B1 | 1/2005 | Garman et al. |
| 6,857,449 B1 | 2/2005 | Chow |
| 6,908,767 B2 | 6/2005 | Bader |
| 6,915,679 B2 | 7/2005 | Chien et al. |
| 6,969,166 B2 | 11/2005 | Clark et al. |
| 7,005,292 B2 | 2/2006 | Wilding et al. |
| 7,018,830 B2 | 3/2006 | Wilding et al. |
| 7,022,518 B1 | 4/2006 | Feye |
| 7,067,263 B2 | 6/2006 | Parce et al. |
| 7,141,386 B2 | 11/2006 | Dunfield et al. |
| 7,155,344 B1 | 12/2006 | Parce et al. |
| 7,160,687 B1 | 1/2007 | Kapur et al. |
| 7,171,983 B2 | 2/2007 | Chien et al. |
| 7,192,769 B2 | 3/2007 | Pykett et al. |
| 7,223,371 B2 | 5/2007 | Hayenga et al. |
| 7,343,248 B2 | 3/2008 | Parce et al. |
| 7,745,209 B2 | 6/2010 | Martin et al. |
| 7,919,319 B2 | 4/2011 | Jervis et al. |
| 8,257,964 B2 | 9/2012 | Hung et al. |
| 8,673,625 B2 | 3/2014 | Hung et al. |
| 8,709,790 B2 | 4/2014 | Hung et al. |
| 9,206,384 B2 | 12/2015 | Lee et al. |
| 9,260,688 B2 | 2/2016 | Hung et al. |
| 9,353,342 B2 | 5/2016 | Hung et al. |
| 9,353,343 B2 | 5/2016 | Hung et al. |
| 9,354,156 B2 | 5/2016 | Lee et al. |
| 9,371,929 B2 | 6/2016 | Hung et al. |
| 9,376,658 B2 | 6/2016 | Hung et al. |
| 9,388,374 B2 | 7/2016 | Hung et al. |
| 9,428,723 B2 | 8/2016 | Lee et al. |
| 9,637,715 B2 * | 5/2017 | Hung ................... C12M 23/12 |
| 2002/0039785 A1 | 4/2002 | Schroeder et al. |
| 2002/0108860 A1 | 8/2002 | Staats |
| 2002/0110905 A1 | 8/2002 | Barbera-Guillem et al. |
| 2002/0177221 A1 | 11/2002 | Nishiguchi et al. |
| 2003/0008388 A1 | 1/2003 | Barbera-Guillem et al. |
| 2003/0008389 A1 | 1/2003 | Carll |
| 2003/0030184 A1 | 2/2003 | Kim et al. |
| 2003/0040104 A1 | 2/2003 | Barbera-Guillem |

(56) References Cited

U.S. PATENT DOCUMENTS

| | | |
|---|---|---|
| 2003/0124623 A1 | 7/2003 | Yager et al. |
| 2003/0143727 A1 | 7/2003 | Chang |
| 2003/0156992 A1 | 8/2003 | Anderson et al. |
| 2003/0211012 A1 | 11/2003 | Bergstrom et al. |
| 2003/0215941 A1 | 11/2003 | Campbell et al. |
| 2004/0029266 A1 | 2/2004 | Barbera-Guillem |
| 2004/0043481 A1 | 3/2004 | Wilson |
| 2004/0072278 A1 | 4/2004 | Chou et al. |
| 2004/0096960 A1 | 5/2004 | Mehta et al. |
| 2004/0132175 A1 | 7/2004 | Vetillard et al. |
| 2004/0202579 A1 | 10/2004 | Larsson et al. |
| 2004/0229349 A1 | 11/2004 | Daridon |
| 2004/0238484 A1 | 12/2004 | Le Pioufle et al. |
| 2005/0009179 A1 | 1/2005 | Gemmiti et al. |
| 2005/0019213 A1 | 1/2005 | Kechagia et al. |
| 2005/0032208 A1 | 2/2005 | Oh |
| 2005/0072946 A1 | 4/2005 | Studer et al. |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0214173 A1 | 9/2005 | Facer et al. |
| 2005/0221373 A1 | 10/2005 | Enzelberger et al. |
| 2005/0260745 A1 | 11/2005 | Domansky et al. |
| 2005/0266582 A1 | 12/2005 | Modlin et al. |
| 2006/0003436 A1 | 1/2006 | DiMilla et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0154361 A1 | 7/2006 | Wikswo et al. |
| 2006/0166354 A1 | 7/2006 | Wikswo et al. |
| 2006/0199260 A1 | 9/2006 | Zhang et al. |
| 2007/0026516 A1 | 2/2007 | Martin et al. |
| 2007/0084706 A1 | 4/2007 | Takayama et al. |
| 2007/0090166 A1 | 4/2007 | Takayama et al. |
| 2007/0122314 A1 | 5/2007 | Strand et al. |
| 2007/0128715 A1 | 6/2007 | Vukasinovic et al. |
| 2007/0243523 A1 | 10/2007 | Ionescu-Zanetti et al. |
| 2007/0264705 A1 | 11/2007 | Dodgson |
| 2007/0275455 A1 | 11/2007 | Hung et al. |
| 2008/0032380 A1 | 2/2008 | Kleis et al. |
| 2008/0038713 A1 | 2/2008 | Gao et al. |
| 2008/0085556 A1 | 4/2008 | Graefing et al. |
| 2008/0176318 A1 | 7/2008 | Wilson et al. |
| 2008/0194012 A1 | 8/2008 | Lee et al. |
| 2008/0227176 A1 | 9/2008 | Wilson |
| 2008/0233607 A1 | 9/2008 | Yu et al. |
| 2009/0023608 A1 | 1/2009 | Hung et al. |
| 2009/0123961 A1 | 5/2009 | Meyvantsson et al. |
| 2009/0148933 A1 | 6/2009 | Battrell et al. |
| 2009/0203126 A1 | 8/2009 | Hung et al. |
| 2010/0151571 A1 | 6/2010 | Vukasinovic et al. |
| 2010/0196908 A1 | 8/2010 | Opalsky et al. |
| 2010/0234674 A1 | 9/2010 | Wheeler et al. |
| 2012/0003732 A1 | 1/2012 | Hung et al. |
| 2012/0164036 A1 | 6/2012 | Stern et al. |
| 2013/0059322 A1 | 3/2013 | Hung et al. |
| 2013/0081757 A1 | 4/2013 | Hung et al. |
| 2013/0090268 A1 | 4/2013 | Hung et al. |
| 2013/0171679 A1 | 7/2013 | Lee et al. |
| 2013/0171682 A1 | 7/2013 | Hung et al. |
| 2014/0057311 A1 | 2/2014 | Kamm et al. |
| 2014/0090735 A1 | 4/2014 | Hung et al. |
| 2014/0099705 A1 | 4/2014 | Hung et al. |
| 2014/0287489 A1 | 9/2014 | Lee et al. |
| 2016/0075984 A1 | 3/2016 | Hung et al. |
| 2016/0312166 A1 | 10/2016 | Lee et al. |
| 2016/0327470 A1 | 11/2016 | Lee et al. |
| 2016/0333297 A1 | 11/2016 | Hung et al. |
| 2016/0333298 A1 | 11/2016 | Hung et al. |
| 2016/0340630 A1 | 11/2016 | Hung et al. |
| 2017/0267961 A1 | 9/2017 | Hung et al. |

FOREIGN PATENT DOCUMENTS

| | | |
|---|---|---|
| EP | 0155237 A2 | 9/1985 |
| EP | 0725134 A2 | 8/1996 |
| EP | 0890636 A1 | 1/1999 |
| GB | 1539263 A | 1/1979 |
| WO | 91/15570 A1 | 10/1991 |
| WO | 00/56870 A1 | 9/2000 |
| WO | 00/60352 A2 | 10/2000 |
| WO | 00/78932 A1 | 12/2000 |
| WO | 01/92462 A1 | 12/2001 |
| WO | 03/085080 A1 | 10/2003 |
| WO | 03/098218 A1 | 11/2003 |
| WO | 2004/059299 A1 | 7/2004 |
| WO | 2004/106484 A2 | 12/2004 |
| WO | 2005/035728 A2 | 4/2005 |
| WO | 2007/008606 A1 | 1/2007 |
| WO | 2007/008609 A2 | 1/2007 |
| WO | 2009/089189 A2 | 7/2009 |
| WO | 2009/102453 A2 | 8/2009 |
| WO | 2012/024646 A2 | 2/2012 |

OTHER PUBLICATIONS

Notice of allowance dated Feb. 2, 2018 in co-pending U.S. Appl. No. 15/161,665.
European communication dated Apr. 3, 2012 in co-pending European patent application No. 06786499.1.
International Search Report and Written Opinion dated Apr. 9, 2009 in PCT application No. PCT/US06/26364 (corresponding to U.S. Appl. No. 11/994,997).
International Search Report and Written Opinion dated Jul. 30, 2009 in corresponding PCT application No. PCT/US2009/030168.
European communication dated Oct. 21, 2013 in corresponding European patent application No. 09701350.2.
International Search Report dated May 14, 2013 in co-pending PCT application No. PCT/US2013/024999.
International Search Report dated Mar. 19, 2013 in co-pending PCT application No. PCT/US2012/067632.
International Preliminary Report on Patentability dated Jun. 12, 2014 in co-pending PCT application No. PCT/US2012/067632.
European communication dated Jul. 28, 2015 in co-pending European patent application No. 12852539.1.
Japanese communication, with English translation, dated Nov. 17, 2015 in co-pending Japanese patent application No. 2015-503203.
Chinese communication, with English translation, dated Jun. 20, 2016 in co-pending Chinese patent application No. 201380018324.1.
Engineering Aspects of Food Biotechnology, Chapter 5, CRC Press: Boca Raton, FL, 2004, copyright 2014, p. 127, "Meet the Stem Cells; Production of Cultured Meat from a Stem Cell Biology Perspective", Brinkhof, et al., 3 pages.
Cellasic Corporation, Onix Application Note, "Microincubator for long term live cell microscopy", Feb. 3, 2012, pp. 1-4.
Optics Express, vol. 14, No. 13, Jun. 2006, pp. 6253-6256, "Fabrication of polymer microlens arrays using capillary forming with a soft mold of micro-holes array and UV-curable polymer", Chang, et al.
Lab Chip, 2007, vol. 7, pp. 641-643, published by the Royal Society of Chemistry, "Rapid fabrication of microchannels using microscale plasma activated templating (uPLAT) generated water molds", Chao, et al.
Lab on a Chip, 2007, vol. 7, pp. 763-769, "A hydrogel-based microfluidic device for the studies of directed cell migration", Cheng, et al.
Lab Chip, 2005, vol. 5, No. 4, pp. 401-406, published by The Royal Society of Chemistry, "Human neural stem growth and differentiation in a gradient-generating microfluidic device", Chung, et al.
Lab on a Chip, 2008, vol. 9, Iss.2 pp. 269-275, "Cell Migration into Scaffolds Under Co-culture Conditions in a Microfluidic Platform," Chung et al.
J. Biochem., vol. 130, pp. 367-376, (2001), "A Method for Micrometer Resolution Patterning of Primary Culture Neurons for SPM Analysis", Degenaar, et al.

(56) References Cited

OTHER PUBLICATIONS

Biotechnology and Bioengineering, vol. 89, No. 1, Jan. 5, 2005, pp. 1-8, "Continuous Perfusion Microfluidic Cell culture Array for High-Throughput Cell-Based Assays", Hung, et al.
Lab Chip, 2005, vol. 5, pp. 44-48, "A novel high aspect ratio microfluidic design to provide a stable and uniform microenvironment for cell growth in a high throughput mammalian cell culture array", Hung, et al.
Lab Chip, 2008, vol. 8, No. 1, pp. 34-57, published by The Royal Society of Chemistry, "Biomolecular gradients in cell culture systems", Keenan, et al.
Keenan et al., "A new method for studying gradient-induced neutrophil desensitization based on an open microfluidic chamber", Lab Chip, 2010, vol. 10, pp. 116-122.
Lab on a Chip, 2009, vol. 9, p. 1797-1800, "Selective and tunable gradient device for cell culture and chemotaxis study", Kim, et al.
Biotechnology and Bioengineering, vol. 97, No. 5, Aug. 1, 2007, pp. 1340-1346, "An Artificial Liver Sinusoid With a Microfluidic Endothelial-Like Barrier for Primary Hepatocyte Culture", Lee, et al.
Lab Chip, 2009, vol. 9, No. 1, pp. 164-166, published by The Royal Society of Chemistry, "Dynamic cell culture: a microfluidic function generator for live cell microscopy", Lee, et al.
Journal of the Association for Laboratory Automation (JALA), 2007, vol. 12, No. 6, pp. 363-367, "Microfluidic System of Automated Cell-Based Assays", Lee, et al.
Lee et al., "Microfluidic Systems for Live Cell Imaging", Methods in Cell Biology, 2011, vol. 102, pp. 77-103.
Lab Chip, 2003, vol. 3, pp. 318-323, published by the The Royal Society of Chemistry, "Fabrication of microfluidic mixers and artificial vasculatures using a high-brightness diode-pumped Nd:YAG laser direct write method", Lim, et al.
Biomed Microdevices (2008), vol. 10, pp. 499-507, "Microfluidic switching system for analyzing chemotaxis responses of wortmannin-inhibited HL-60 cells", Liu, et al.
Biomaterials, 2008, vol. 29, No. 22, pp. 3237-3244, "A gel-free 3D microfluidic cell culture system", Ong, et al.
Lab on a Chip, 2007, vol. 7, pp. 1673-1680, "Gradient generation by an osmotic pump and the behavior of human mesenchymal stem cells under the fetal bovine serum concentration gradient", Park, et al.
Angew. Chem. Int. Ed., 2004. vol. 43, pp. 1531-1536, "Minimal Functional Model of Hemostasis in a Biomimetic Microfluidic system", Runyon, et al.
Biomedical Microdevices, 2003, vol. 5, No. 3, pp. 235-244, "Microfluidic Patterning of Cellular Biopolymer Matrices for Biomimetic 3-D Structures", Tan, et al.
Office Action dated Feb. 22, 2013 in co-pending U.S. Appl. No. 13/436,992.
Office Action dated Sep. 6, 2013 in co-pending U.S. Appl. No. 13/436,992.
Final Rejection dated Apr. 11, 2014 in co-pending U.S. Appl. No. 13/436,992.
Office Action dated Nov. 6, 2014 in co-pending U.S. Appl. No. 13/436,992.
Final Rejection dated Mar. 23, 2015 in co-pending U.S. Appl. No. 13/436,992.
Office action dated Nov. 20, 2015 in co-pending U.S. Appl. No. 13/436,992.
Final rejection dated Mar. 11, 2016 in co-pending U.S. Appl. No. 13/436,992.
Office Action dated Jun. 19, 2015 in co-pending U.S. Appl. No. 14/221,615.
Notice of Allowance dated Jan. 6, 2016 in co-pending U.S. Appl. No. 14/221,615.
Notice of Allowance dated Apr. 11, 2016 in co-pending U.S. Appl. No. 14/221,615.
Notice of Allowance dated Dec. 6, 2016 in co-pending U.S. Appl. No. 13/436,992.
Office action dated Jul. 6, 2017 in co-pending U.S. Appl. No. 15/161,665.
Office Action dated Feb. 23, 2017 in co-pending U.S. Appl. No. 15/175,749.
Office action dated Nov. 1, 2017 in co-pending U.S. Appl. No. 15/175,749.
Notice of allowance dated Jun. 11, 2018 in co-pending U.S. Appl. No. 15/163,398.
Notice of allowance dated Jul. 5, 2018 in co-pending U.S. Appl. No. 15/163,818.
Office action dated Jul. 10, 2018 in co-pending U.S. Appl. No. 15/175,749.
Notice of allowance dated May 31, 2018 in co-pending U.S. Appl. No. 15/161,665.
Final rejection dated Mar. 27, 2018 in co-pending U.S. Appl. No. 15/175,749.
Office action dated Mar. 21, 2018 in co-pending U.S. Appl. No. 15/163,818.
Office action dated Apr. 18, 2018 in co-pending U.S. Appl. No. 15/175,449.
Ex parte Quayle action mailed Apr. 24, 2018 in co-pending U.S. Appl. No. 15/163,398.
Ex parte Quayle action mailed May 21, 2018 in co-pending U.S. Appl. No. 15/163,818.
Notice of allowance dated Aug. 6, 2018 in co-pending U.S. Appl. No. 15/161,665.
Notice of allowance dated Sep. 12, 2018 in co-pending U.S. Appl. No. 15/175,449.

* cited by examiner

Cells are cultured in this area

4μm wide and 40μm tall channels prevent cells from growing out.

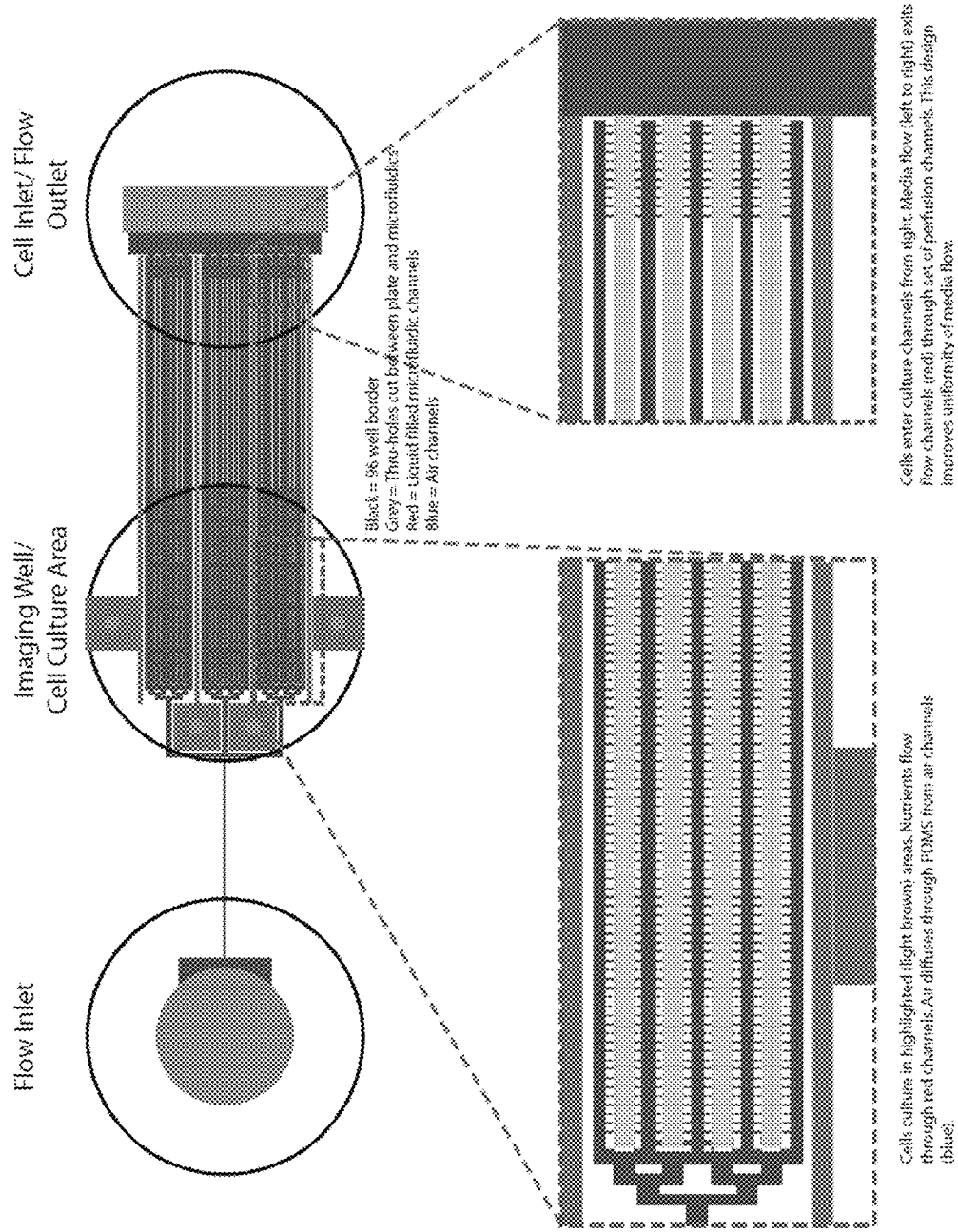
FIG. 8 E.G., 2,500 CELLS IN EACH SINUSOID 50 micron width 100 micron width 75 micron width 125 micron width Soft polymer attached to the
primed acrylic wafer Replicated microfluidic array

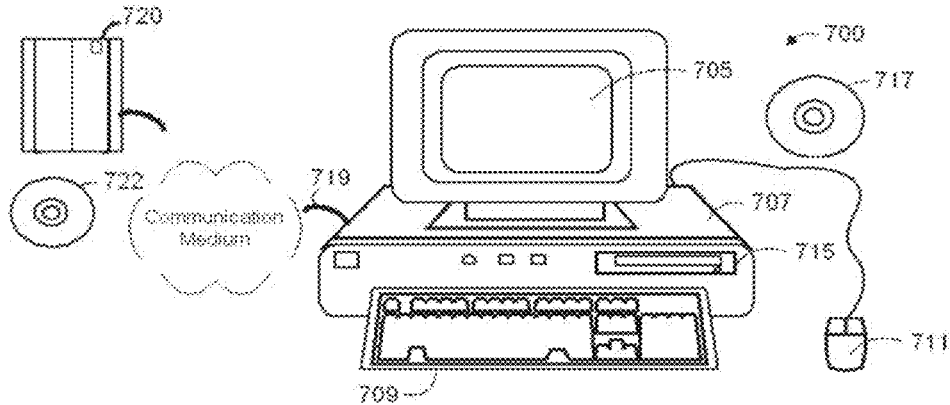

*FIG. 34*

| Disease Classification | Disease |
|---|---|
| Cardiovascular Disease | Atherosclerosis; Unstable angina; Myocardial Infarction; Restenosis after angioplasty or other percutaneous intervention; Congestive Heart Failure; Myocarditis; Endocarditis; Endothelial Dysfunction; Cardiomyopathy |
| Endocrine Disease | Diabetes Mellitus I and II; Thyroiditis; Addisson's Disease |
| Infectious Disease | Hepatitis A, B, C, D, E; Malaria; Tuberculosis; HIV; Pneumocystis Carinii; Giardia; Toxoplasmosis; Lyme Disease; Rocky Mountain Spotted Fever; Cytomegalovirus; Epstein Barr Virus; Herpes Simplex Virus; Clostridium Difficile Colitis; Meningitis (all organisms); Pneumonia (all organisms); Urinary Tract Infection (all organisms); Infectious Diarrhea (all organisms) |
| Angiogenesis | Pathologic angiogenesis; Physiologic angiogenesis; Treatment induced angiogenesis |
| Inflammatory/Rheumatic Disease | Rheumatoid Arthritis; Systemic Lupus Erythematosis; Sjogrens Disease; CREST syndrome; Scleroderma; Ankylosing Spondylitis; Crohn's; Ulcerative Colitis; Primary Sclerosing Cholangitis; Appendicitis; Diverticulitis; Primary Biliary Sclerosis; Wegener's Granulomatosis; Polyarteritis nodosa; Whipple's Disease; Psoriasis; Microscopic Polyangiitis; Takayasu's Disease; Kawasaki's Disease; Autoimmune hepatitis; Asthma; Churg-Strauss Disease; Beurger's Disease; Raynaud's Disease; Cholecystitis; Sarcoidosis; Asbestosis; Pneumoconioses |
| Transplant Rejection | Heart; Lung; Liver; Pancreas; Bowel; Bone Marrow; Stem Cell; Graft versus host disease; Transplant vasculopathy |
| Leukemia and Lymphoma | |

*FIG. 35. (TABLE 1)*

CELL CULTURE ARRAY SYSTEM FOR AUTOMATED ASSAYS AND METHODS OF OPERATION AND MANUFACTURE

CROSS REFERENCE TO RELATED APPLICATIONS

This application is a continuation of U.S. patent application Ser. No. 12/348,907 filed Jan. 5, 2009 (now U.S. Pat. No. 9,376,658 issued Jun. 28, 2016), which claims priority from provisional patent application 61/037,297 filed Mar. 17, 2008 and from 61/018,882 filed Jan. 3, 2008, each incorporated herein by reference.

This application discusses technology related to U.S. Ser. No. 11/994,997, filed Aug. 11, 2008 (now U.S. Pat. No. 9,260,688 issued Feb. 16, 2016), which is a National Stage Entry of PCT/US06/26364, filed Jul. 6, 2006 and which claims priority from provisional patent application 60/773,467 filed 14 Feb. 2006 and from provisional patent application 60/697,449 filed 7 Jul. 2005.

This application discusses technology related to U.S. application Ser. No. 12/019,857, filed Jan. 25, 2008 (now U.S. Pat. 9,354,156 issued May 31, 2016),which claims priority to U.S. Provisional Patent Application No. 60/900,651 filed on Feb. 8, 2007.

This application discusses technology related to U.S. application Ser. No. 11/648,2071, filed Dec. 29, 2006 (now U.S. Pat. 8,257,964 issued Sep. 4, 2012), which claims priority to U.S. Provisional Patent Application U.S. provisional patent application No. 60/756,399 filed on Jan. 4, 2006. All of these applications are incorporated herein by reference for all purposes.

COPYRIGHT NOTICE

Pursuant to 37 C.F.R. 1.71(e), applicants note that a portion of this disclosure contains material that is subject to copyright protection (such as, but not limited to, diagrams, device photographs, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention in various embodiments relates to handling of micro-objects, such as cells or micro-fabricated particles are beads, using a microfluidic system and particularly is directed to a configuration that can be used with various standard automated handling systems. In particular embodiments, the invention involves an automated system for cell culture.

BACKGROUND OF THE INVENTION

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Microfluidic cell culture is a promising technology for applications in the drug screening industry. Key benefits include improved biological function, higher-quality cell-based data, reduced reagent consumption, and lower cost. High quality molecular and cellular sample preparations are important for various clinical, research, and other applications. In vitro samples that closely represent their in vivo characteristics can potentially benefit a wide range of molecular and cellular applications. Handling, characterization, culturing, and visualization of cells or other biologically or chemically active materials (such as beads coated with various biological molecules) has become increasingly valued in the fields of drug discovery, disease diagnoses and analysis, and a variety of other therapeutic and experimental work.

Mammalian cell culture is particularly challenging, particularly for maintaining effective solid aggregates of cells in culture. Advances have been made by adapting various microfabrication and microfluidic technologies to cell culture, though there remains an ongoing need for a device that can be economically manufactured and used to provide effective cell culture.

Publications and/or patent documents that discuss various strategies related to cell culture using microfluidic systems and related activities include the following U.S. patent applications and non-patent literature, which, along with all citations therein, are incorporated herein by reference for all purposes. A listing of these references here does not indicate the references constitute prior art.

Cytoplex, Inc. U.S. Pat. No. 6,653,124 "Array-based microenvironment for cell culturing, cell monitoring and drug-target validation."

Cellomics, Inc. U.S. Pat. No. 6,548,263 "Miniaturized cell array methods and apparatus for cell-based screening."

Fluidigm, Inc. Published Application 20040229349 (Nov. 18, 2004) "Microfluidic particle-analysis systems."

OTHER REFERENCES I

1. T. H. Park and M. L. Shuler, Biotechnol. Prog., 2003, 19, 243.
2. G. M. Walker, H. C. Zeringue and D. J. Beebe, Lab Chip, 2004, 4, 91.
3. E. Leclerc, Y. Sakai and T. Fujii, Biotechnol. Prog., 2004, 20, 750.
4. M. J. Powers, K. Domansky, M. R. Kaazempur-Mofrad, A. Kalezi, A. Capitano, A. Upadhyaya, P. Kurzawski, K. E. Wack, D. B. Stolz, R. Kamm and L. G. Griffith, Biotechnol. Bioeng., 2002, 78, 257.
5. K. Viravaidya and M. L. Shuler, Biotechnol. Prog., 2004, 20, 590.
6. Y. Kostov, P. Harms, L. Randers-Eichhorn and G. Rao, Biotechnol. Bioeng., 2001, 72, 346.
7. N. Li Jeon, H. Baskaran, S. K. Dertinger, G. M. Whitesides, L. Van der Water and M. Toner, Nat. Biotechnol., 2002, 20, 826.
8. T. Thorsen, S. J. Maerkl and S. R. Quake, Science, 2002, 298, 580.
9. H. Andersson and A. van den Berg, Lab Chip, 2004, 4, 98.

OTHER REFERENCES II

10. Dove, A. (2003) Nature Biotechnology 21, 859-864.
11. Entzeroth, M. (2003) Current Opinion in Pharmacology 3, 522-529.
12. Boess, F.; Kamber, M.; Romer, S.; Gasser, R.; Muller, D.; Albertini, S.; Suter, L. Toxicol Sci 2003, 73, (2), 386-402.

13. Rodriguez-Antona, C.; Donato, M. T.; Boobis, A.; Edwards, R. J.; Watts, P. S.; Castell, J. V.; Gomez-Lechon, M. J. Xenobiotica 2002, 32, (6), 505-20.

14. Cukierman, E.; Pankov, R.; Stevens, D. R.; Yamada, K. M. Science 2001, 294, (5547), 1708-12.

15. Griffith, L. G.; Swartz, M. A. Nat Rev Mol Cell Biol 2006, 7, (3), 211-24.

16. Revzin, A.; Rajagopalan, P.; Tilles, A. W.; Berthiaume, F.; Yarmush, M. L.; Toner, M. Langmuir 2004, 20, (8), 2999-3005.

17. Flaim, C. J.; Chien, S.; Bhatia, S. N. Nat Methods 2005, 2, (2), 119-25.

18. Anderson, D. G.; Levenberg, S.; Langer, R. Nat Biotechnol 2004, 22, (7), 863-6.

19. Battle, T.; Stacey, G. Cell Biol Toxicol 2001, 17, (4-5), 287-99.

20. LeCluyse, E. L.; Bullock, P. L.; Parkinson, A. Advanced Drug Delivery Reviews 1996, (22), 133-186.

21. Ben-Ze'ev, A.; Robinson, G. S.; Bucher, N. L.; Farmer, S. R. Proc Natl Acad Sci USA 1988, 85, (7), 2161-5.

22. Bhatia, S. N.; Balis, U. J.; Yarmush, M. L.; Toner, M. Faseb J 1999, 13, (14), 1883-900.

23. Berthiaume, F.; Moghe, P. V.; Toner, M.; Yarmush, M. L. Faseb J 1996, 10, (13), 1471-84.

24. Stevens, M. M.; George, J. H. Science 2005, 310, (5751), 1135-8.

25. Bissell, M. J.; Rizki, A.; Mian, I. S. Curr Opin Cell Biol 2003, 15, (6), 753-62.

26. Allen, J. W.; Bhatia, S. N. Biotechnol Bioeng 2003, 82, (3), 253-62.

27. Hung, P. J.; Lee, P. J.; Sabounchi, P.; Aghdam, N.; Lin, R.; Lee, L. P. Lab Chip 2005, 5, (1), 44-8.

28. Lee, P. J.; Hung, P. J.; Rao, V. M.; Lee, L. P. Biotechnol Bioeng 2005.

29. Puhl, G.; Schaser, K. D.; Vollmar, B.; Menger, M. D.; Settmacher, U. Transplantation 2003, 75, (6), 756-61.

30. Park, J.; Berthiaume, F.; Toner, M.; Yarmush, M. L.; Tilles, A. W. Biotechnol Bioeng 2005, 90, (5), 632-44.

31. Anderson, K.; Wilkinson, R.; Grant, M. H. Int J Artif Organs 1998, 21, (6), 360-4.

32. Landry, J.; Bernier, D.; Ouellet, C.; Goyette, R.; Marceau, N. J Cell Biol 1985, 101, (3), 914-23.

33. A. Ben-Ze'ev, G. S. Robinson, N. L. Bucher, S. R. Farmer, Proc Natl Acad Sci USA 85, 2161 (April, 1988).

34. J. Landry, D. Bernier, C. Ouellet, R. Goyette, N. Marceau, J Cell Biol 101, 914 (September, 1985).

35. S. A. Stoehr, H. C. Isom, Hepatology 38, 1125 (November, 2003).

36. Zhang, X, Wang, W, Yu, W, Xie, Y, Zhang, X, Zhang, Y, Ma, X. Biotechnol Prog 2005, 21, 1289-96.

37. Kelm, J, Timmins, N, Brown, C, Fussenegger, M, Nielsen, L. Biotechnology and Bioengineering. 2003, 83(2) 173-180.

38. Kuns-Schughart, L, Freyer, J, Hofstaedter, F, Ebner, R. J. Biomolecular Screening. 2004, 9(4) 273-285.

Earlier work and patent documents as cited above involving at least one of the present inventors discuss various configurations, methods, and systems related to microfluidic cell culture and that earlier work and those patent documents are incorporated herein by reference.

SUMMARY

The present invention involves various components, systems, and methods related to improved microfluidic cell culture systems. In one aspect, the invention involves novel microfluidic cell culture systems and methods that have advantages over previously proposed microfluidic structures. In another aspect, the invention involves novel structures and methods for integrating multiple microfluidic cell culture systems to a microtiter well plate structure, such as a standard culture-well plate formats (e.g., a 96-well SBS culture plate). In a further aspect, the invention involves novel fabrication methods for creating an array of microfluidic cell culture areas suitable for integration with a well plate. In another aspect, the invention involves novel systems, methods, and components for an improved automated high-throughput cell culture and/or screening system using microfluidic cell cultures In particular embodiments, key design features include the elimination of tubing and connectors to the plates themselves, the ability to maintain long-term continuous perfusion cell culture using a passive gravity-driven flow, and direct analysis on the outlet wells and/or cellular observation wells of the microfluidic plate.

For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

In some of the drawings and detailed descriptions below, the present invention is described in terms of the important independent embodiment of a complete, fully automated, cellular culture system and components thereof. This should not be taken to limit various novel aspects of the invention, which, using the teachings provided herein, can be applied to a number of other situations. In some of the drawings and descriptions below, the present invention is described in terms of a number of specific example embodiments including specific parameters related to dimensions of structures, pressures or volumes of liquids, temperatures, electrical values, and the like. Except where so provided in the attached claims, these parameters are provided as examples and do not limit the invention to other devices or systems with different dimensions. For purposes of providing an more illuminating description, particular known fabrication steps, cell handling steps, reagents, chemical or mechanical process, and other known components that may be included to make a system or manufacture a device according to specific embodiments of the invention are given as examples. It will be understood to those of skill in the art that except were specifically noted herein otherwise, various known substitutions can be made in the processes described herein.

All references, publications, patents, and patent applications cited in this submission are hereby incorporated by reference in their entirety for all purposes.

BRIEF DESCRIPTION OF THE DRAWINGS

FIG. 34 is a block diagram showing a representative example logic device in which various aspects of the present invention may be embodied.

FIG. 35 (Table 1) illustrates an example of diseases, conditions, or states that can evaluated or for which drugs or other therapies can be tested according to specific embodiments of the present invention.

DETAILED DESCRIPTION OF SPECIFIC EMBODIMENTS

1. Overview

Definitions

Figure 1:
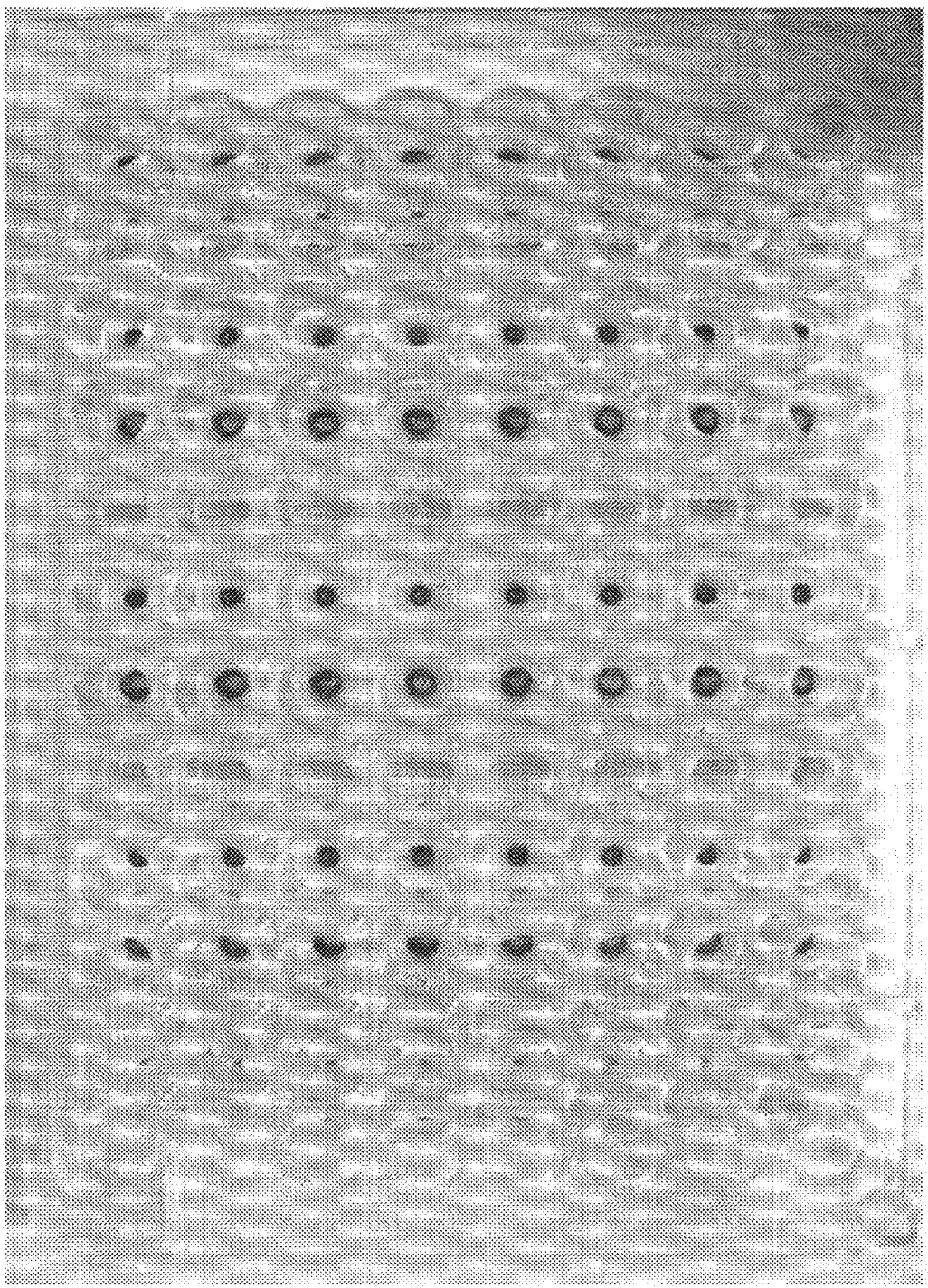
FIG. 1 is a top view of an example array of cell culture units according to specific embodiments of the invention. In this example, 32 culture units are provided on a 96-well plate (such as the Society for Biomolecular Screening (SBS) standard microfluidic bioreactor array schematic), with wells arranged in 12 columns (shown vertically) by 8 rows. In this example, each cell culture unit occupies three wells, one for use as a medium inlet, one for use as a cell inlet/medium outlet, and one for use for cell imaging (which appears as a dark rectangle in the wells in the figure) and/or for providing air passages to a cell culture area. In specific embodiments, each unit can be used as an independent biomimetic cell.

A "particle" refers to biological cells, such as mammalian or bacterial cells, viral particles, or liposomal or other particles that may be subject to assay in accordance with the invention. Such particles have minimum dimensions between about 50-100 nm, and may be as large as 20 microns or more. When used to describe a cell assay in accordance with the invention, the terms "particles" and "cells" may be used interchangeably.

A "microwell" refers to a micro-scale chamber able to accommodate a plurality of particles. A microwell is typically cylindrical in shape and has diameter and depth dimensions in a preferred embodiment of between 100 and 1500 microns, and 10 and 500 microns, respectively. When used to refer to a microwell within the microwell array device of the invention, the term "well" and "microwell" are used interchangeably.

A "microchannel" refers to a micron-scale channel used for connecting a station in the device of the invention with a microwell, or a station and a valve associated with the microwell. A microchannel typically has a rectangular, e.g., square cross-section, with side and depth dimensions in a preferred embodiment of between 10 and 500 microns, and 10 and 500 microns, respectively. Fluids flowing in the microchannels may exhibit microfluidic behavior. When used to refer to a microchannel within the microwell array device of the invention, the term "microchannel" and "channel" are used interchangeably.

A "microfluidics device" refers to a device having various station or wells connected by micron-scale microchannels in which fluids will exhibit microfluidic behavior in their flow through the channels.

A "microwell array" refers to an array of two or more microwells formed on a substrate.

A "device" is a term widely used in the art and encompasses a broad range of meaning. For example, at its most basic and least elaborated level, "device" may signify simply a substrate with features such as channels, chambers and ports. At increasing levels of elaboration, the "device" may further comprise a substrate enclosing said features, or other layers having microfluidic features that operate in concert or independently. At its most elaborated level, the "device" may comprise a fully functional substrate mated with an object that facilitates interaction between the external world and the microfluidic features of the substrate. Such an object may variously be termed a holder, enclosure, housing, or similar term, as discussed below. As used herein, the term "device" refers to any of these embodiments or levels of elaboration that the context may indicate.

Microfluidic systems provide a powerful tool to conduct biological experiments. Recently, elastomer-based microfluidics has especially gained popularity because of its optical transparency, gas permeability and simple fabrication methods. However, the interface with the end-users requires labor-intensive hole punching through the elastomer, and additional steps of tubing and syringe pump connection.

The present invention involves integrated elastomer-based microfluidics on standard well plates, with special focus on hepatocyte culture applications. The invention further involves methods of manufacture of such plates and components and a system for automating cell culture using such plates. Advantages of specific embodiments include use of a standard microtiter plate format, tubing free cell culture, and a biomimetic liver microenvironment.

A system according to specific embodiments of the invention (for example, using 96-well standard plates) can be operated using standard techniques and equipment for handling standard microtiter plates, as are well known in the art. For example, liquid dispensing is achieved with standard pipette mechanics, and cell culture and analysis can be made compatible with existing incubators and plate readers.

According to further embodiments of the invention, a novel cell loading system uses a pneumatic manifold and pneumatic pressure to place cells in the micro culture area. With the addition of this cell loading system, microfluidic cell culture and analysis can be fully automated using other automated equipment that exists for handling standard titer plates.

In further embodiments, the gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (up to 4 days) without the use of bulky external pumps or tubes.

In further embodiments, the invention involves a microfluidic system to allow control of the cell culture environment for long-term time-lapse microscopy of adherent cells. As the trend towards "systems biology" continues, it will become increasingly important to study dynamic behavior in individual live cells as well as to improve the functionality and economics of high throughput live cell screening. According to specific embodiments of the invention, the invention provides a multiplexed microfluidic flow chamber allowing for time-lapse microscopy experimentation among other assays. The microfluidic chamber uses an artificial endothelial barrier to separate cells from flow channels. The device is formatted to a standard well plate, allowing liquid and cell samples to be directly pipetted into the appropriate inlet reservoirs using standard equipment. A custom pneumatic flow controller is then used to load the cells into the culture regions as well as to switch between different exposure solutions. A digital software interface can be used to allow a user to program specific inputs (pulses, ramps, etc.) over time to expose the cells to complex functions during time-lapse imaging.

Dynamic responses in living cells are the foundation for phenomena such as biological signal processing, gene expression regulation, differentiation, and cell division. In specific embodiments, the invention involves a system capable of controlling the cellular microenvironment in a multiplexed format compatible with current cell culture methods. Cell response can be quantified using high magnification fluorescence microscopy to derive kinetic information with sub-cellular resolution. This capability has broad applications in cellular systems biology where dynamic single cell response experiments are not currently practical.

2. Microfluidic Culture System and Array

The application referenced above (U.S. Ser. No. 11/994, 997) discussed a variety of different cell culture configurations and fabrication techniques. Portions of the operation of the cell culture areas and materials are useful as background to the present discussion. In some examples therein, one or more micro culture areas are connected to a medium or reagent channel via a grid of fluidic passages (or diffusion inlets or conduits), wherein the grid comprises a plurality of intersection micro high fluidic resistance passages. In one discussed example, passages in the grid are about 1 to 4 μm in height, 25 to 50 μm in length and 5 to 10 μm in width, the grid allowing for more even diffusion between medium or reagent channels and the culture area and allowing for easier manufacturing and more even diffusion. The earlier application further discussed that the high fluidic resistance ratio between the microchamber and the perfusion/diffusion passages or grid (e.g., ratios in the range of about 10:1, 20:1 to 30:1) offers many advantages for cell culture such as: (1) size exclusion of cells; (2) localization of cells inside a microchamber; (3) promoting a uniform fluidic environment for cell growth; (4) ability to configure arrays of micro-chambers or culture areas; (4) ease of fabrication, and (5) manipulation of reagents without an extensive valve network. Examples were illustrated wherein a grid-like perfusion barrier can be much shorter than the culture area or can be near to or at the same height, according to specific embodiments of the invention and further wherein various configurations for culture devices were illustrated. The application also discussed a CAD drawing of a proposed 96-unit microfluidic bioreactor wherein each well was an SBS standard size (3.5 mm in diameter) in order to be compatible with existing robotic liquid handling systems and plate readers. The application also discussed several different configurations for an artificial sinusoid using both cut passages and grids and with a flow-around perfusion design.

FIG. 1 is a top view of an example array of cell culture units according to specific embodiments of the invention. In this example, 32 culture units are provided on a 96-well plate (such as the Society for Biomolecular Screening (SBS) standard microfluidic bioreactor array schematic), with wells arranged in 12 columns (shown vertically) by 8 rows. In this example, each cell culture unit occupies three wells, one for use as a medium inlet, one for use as a cell inlet/medium outlet, and one for use for cell imaging (which appears as a dark rectangle in the wells in the figure) and/or for providing air passages to a cell culture area. In specific embodiments, each unit can be used as an independent biomimetic cell.

Figure 2:
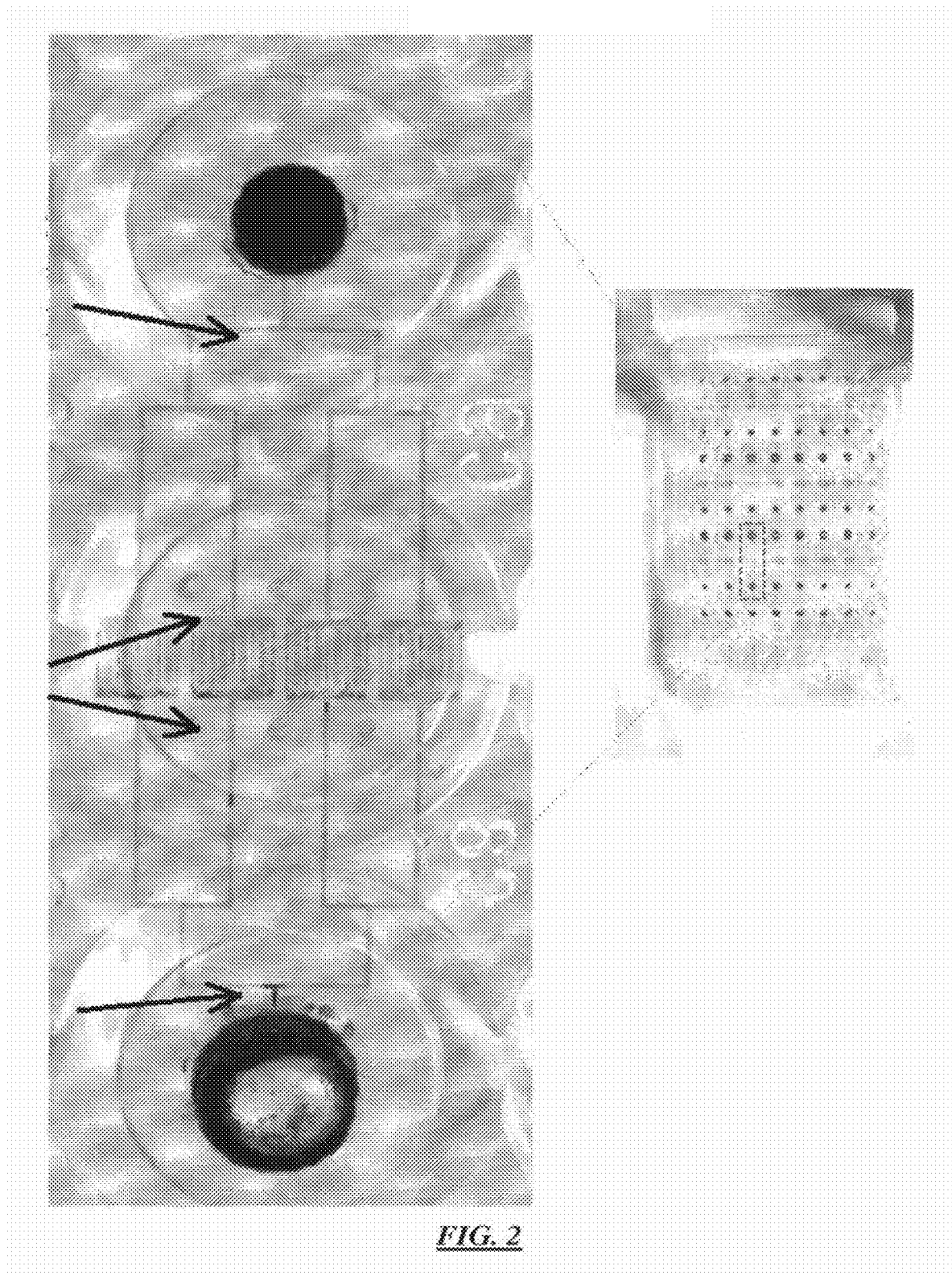
FIG. 2 is an underside view showing one culture unit occupying three wells according to specific embodiments of the invention.

FIG. 2 is an underside view showing one culture unit occupying three wells according to specific embodiments of the invention. In this example, the cell culture portion visible in the middle well is divided into four blocks, with each block having four separated cell culture channels surrounded by medium channels used for medium fluidic passage. In particular embodiments, these four separated cell culture channels may be referred to as sinusoids or artificial sinusoids, regardless of whether the far end of the areas has a rounded shape. Separation into four blocks facilitates air diffusion through the material that defines the microfluidic channels (such as silicone elastomer polydime-thylsiloxane (PDMS)) structure into the culture areas. Six air holes to facilitate air passage are shown.

Figure 3:
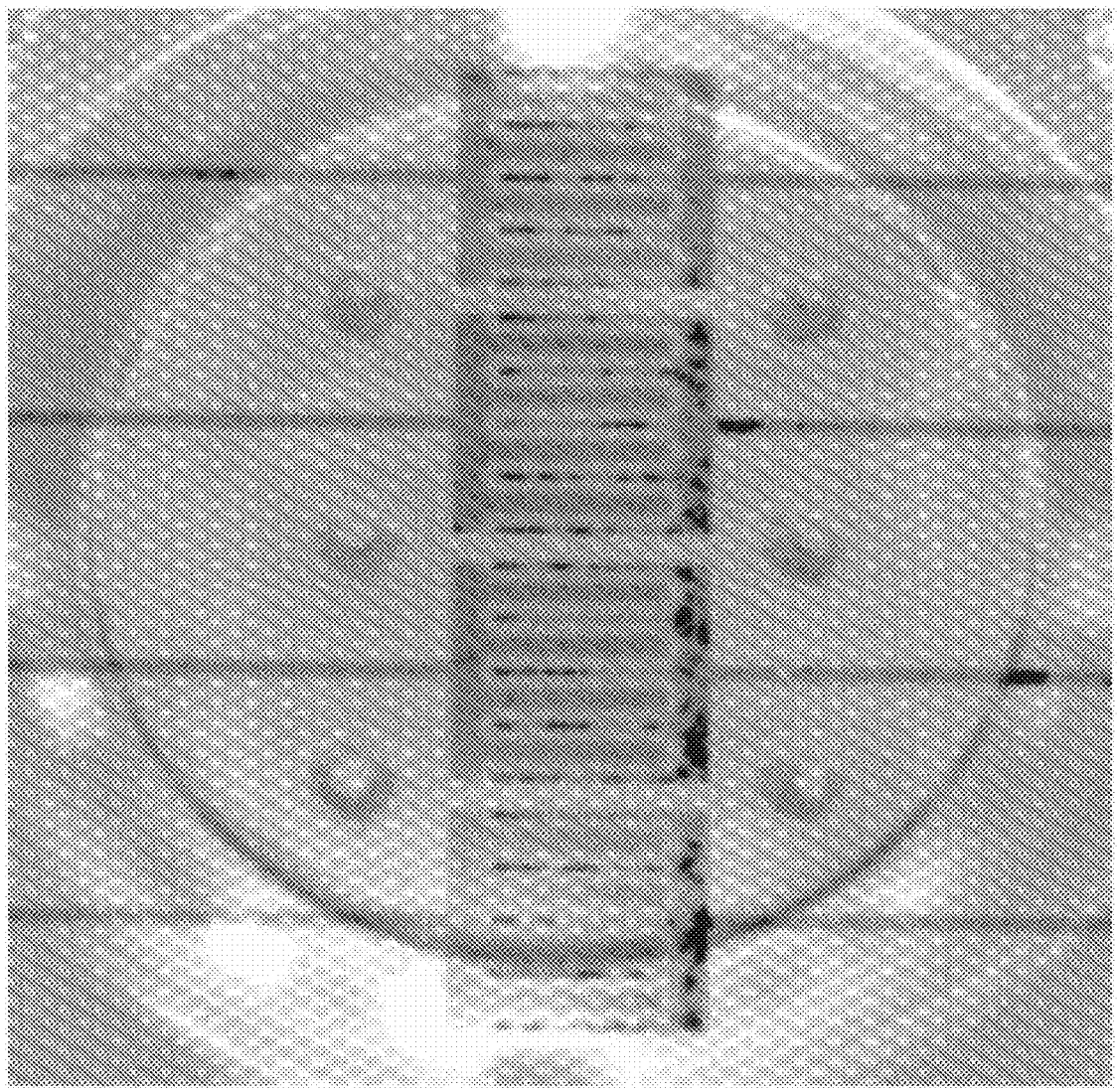
FIG. 3 is a close-up underside view illustrating details of the microfluidic cell culture areas described above according to specific embodiments of the invention. In this figure, the cell inlet/media outlet is to the left, and the media inlet is to the right.

FIG. 3 is a close-up underside view illustrating details of the microfluidic cell culture areas described above according to specific embodiments of the invention.

Figure 4:
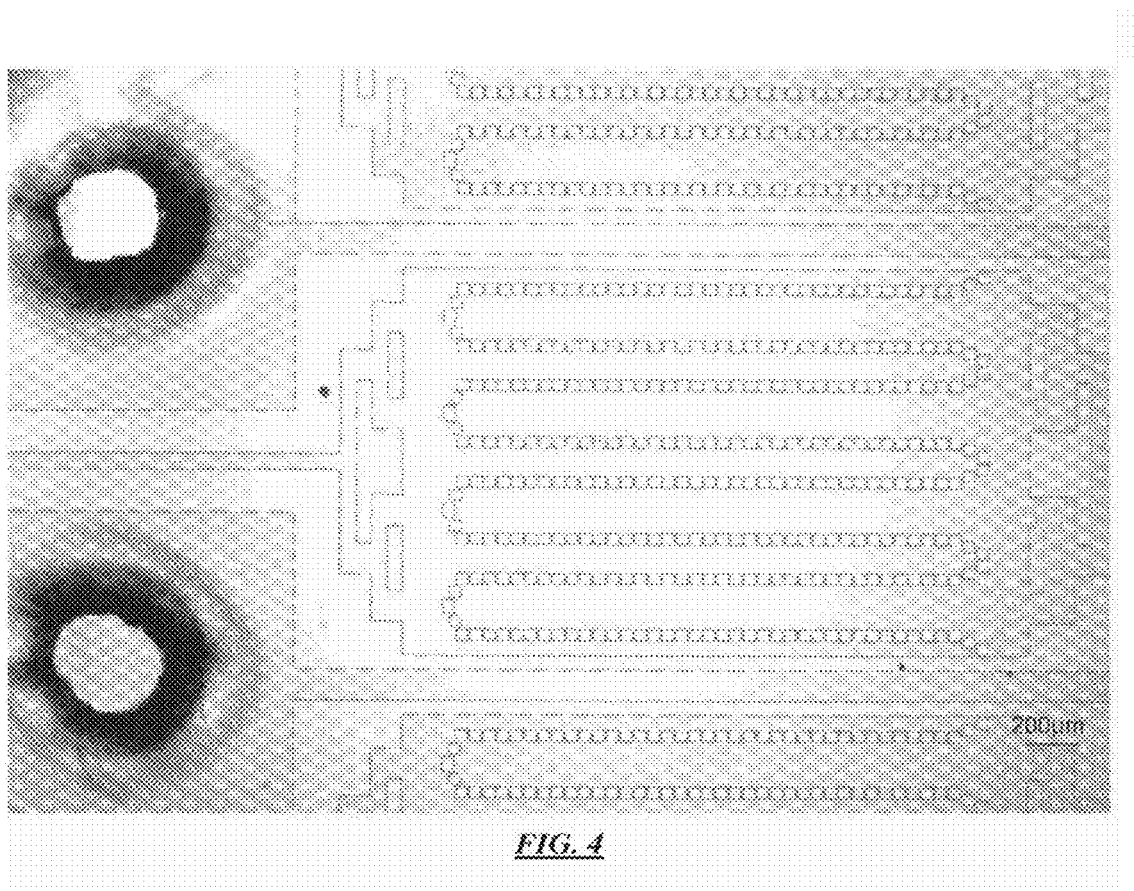
FIG. 4 is a close up micrograph of a cell culture area illustrating two large air holes at the left of the figure each connected to an air passage that is placed between the blocks, each block having four cell culture sinusoids according to specific embodiments of the invention. In this figure, the cell inlet/media outlet is to the right, and the media inlet is to the left. Also visible in the photo, are a media multiplexor structures to the left in each block, and an optional cell inlet multiplexor to the right in each block.

FIG. 4 is a close up micrograph of a cell culture area illustrating two large air holes at the left of the figure each connected to an air passage that is placed between the blocks, each block having four cell culture sinusoids according to specific embodiments of the invention.

Figure 5:
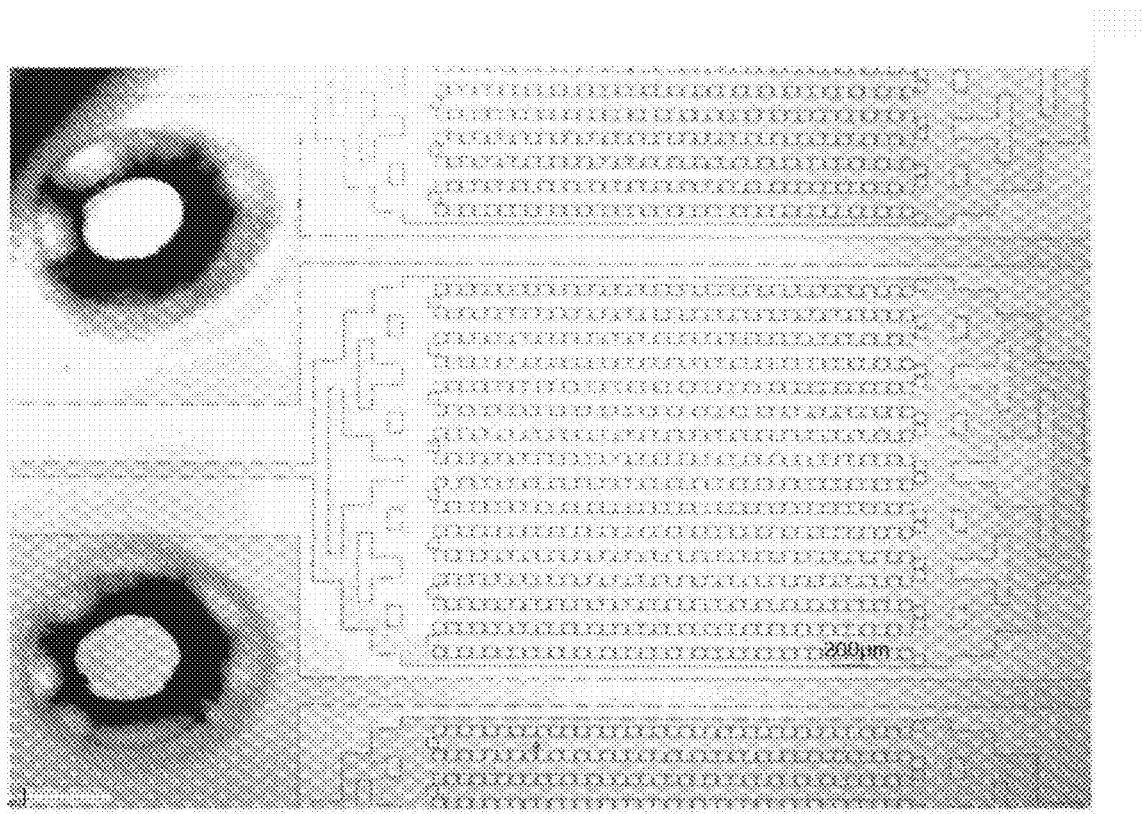
FIG. 5 is a close up micrograph of a cell culture area illustrating two large air holes at the left of the figure each connected to an air passage that is placed between the blocks, each block having eight cell culture sinusoids according to specific embodiments of the invention.

FIG. 5 is a close up micrograph of a cell culture area illustrating two large air holes at the left of the figure each connected to an air passage that is placed between the blocks, each block having eight cell culture sinusoids according to specific embodiments of the invention.

Figure 6:
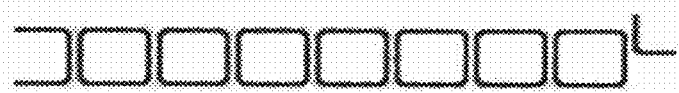
FIG. 6 illustrates high aspect ratio channels surrounding cell culture areas wherein channels between solid structures are approximately 4 µm wide and 40 µm tall to prevent cells from growing out. The channels in this example are separated by approximately 40 µm.
Figure 6:
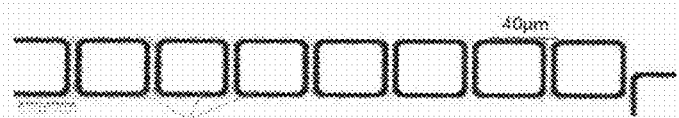

FIG. 6 illustrates high aspect ratio channels surrounding cell culture areas wherein channels between solid structures are approximately 4 μm wide and 40 μm tall to prevent cells from growing out. The channels in this example are separated by approximately 40 μm.

Figure 7A:
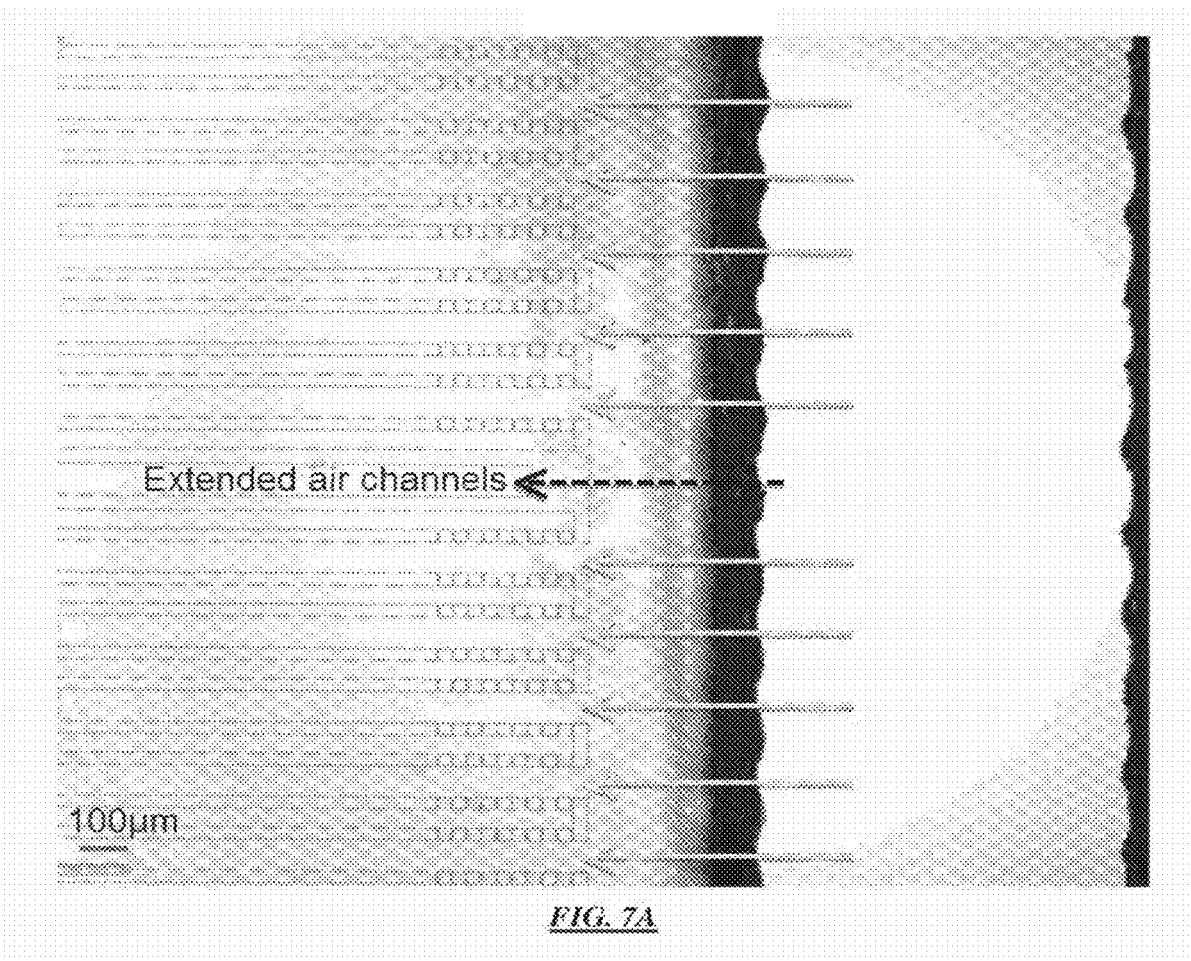
FIG. 7A illustrates a cell inlet/media outlet of a modified cell culture area with a large rectangular cell inlet to provide for easier cell loading and with a cell loading perfusion area and a solid wall cell culture area. The arrows from the right indicate cell-loading direction.

FIG. 7A illustrates a cell inlet/media outlet of a modified cell culture area with a large rectangular cell inlet to provide for easier cell loading and with a cell loading perfusion area and a solid wall cell culture area.

Figure 7B:
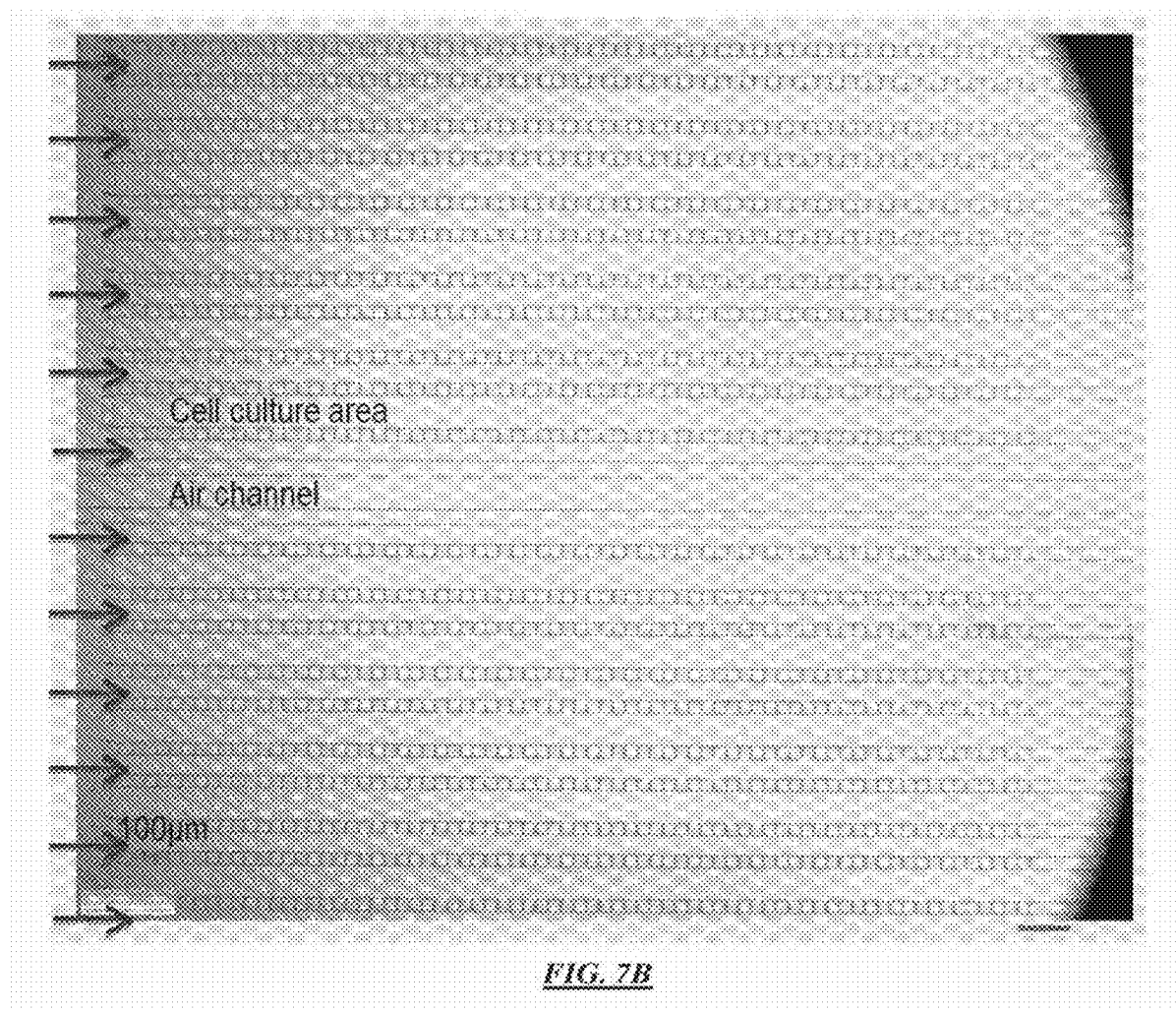
FIG. 7B illustrates the media inlet/cell culture area of a modified microfluidic cell culture system according to specific embodiments of the invention. In this example, cell loading is from the right and media flow, as indicated by the arrows, is from the left.

FIG. 7B illustrates the media inlet/cell culture area of a modified microfluidic cell culture system according to specific embodiments of the invention. In this example, cell loading is from the right and media flow, as indicated by the arrows, is from the left. A further difference in the modified design is that perfusion passages are absent in a portion of the cell culture channel (or artificial sinusoid). This has been found to more easily locate cells at the end of the cell culture channel in the cell culture area. Optionally, a portion of the cell culture channel near the fluid outlet has perfusion passages to ensure fluid flow after cells have aggregated at the culture end. The improved design provides for easier cell loading and a longer cell culture areas and cell culture channels to culture more cells and more uniform flow of nutrients. It has been found that in operation cells localize/stick to the areas of the culture channel that are immediately next to the perfusion passages. The segment of the cell culture channel between the main culture area region and the other set of perfusion passages near the cell inlet is devoid of cells, because the flow profile carries them out, particularly during cell loading. Thus, this modified design prevents the cells from spreading into the "flow" channels after a few days and stop the flow. In the modified design, the flow remains unhindered since the cells cannot spread past the long cell culture channel segment (where there are no perfusion passages). In an example system, up to about 2,500 liver cells may be cultured in each area as shown in FIG. 7 and FIG. 8.

Figure 8:
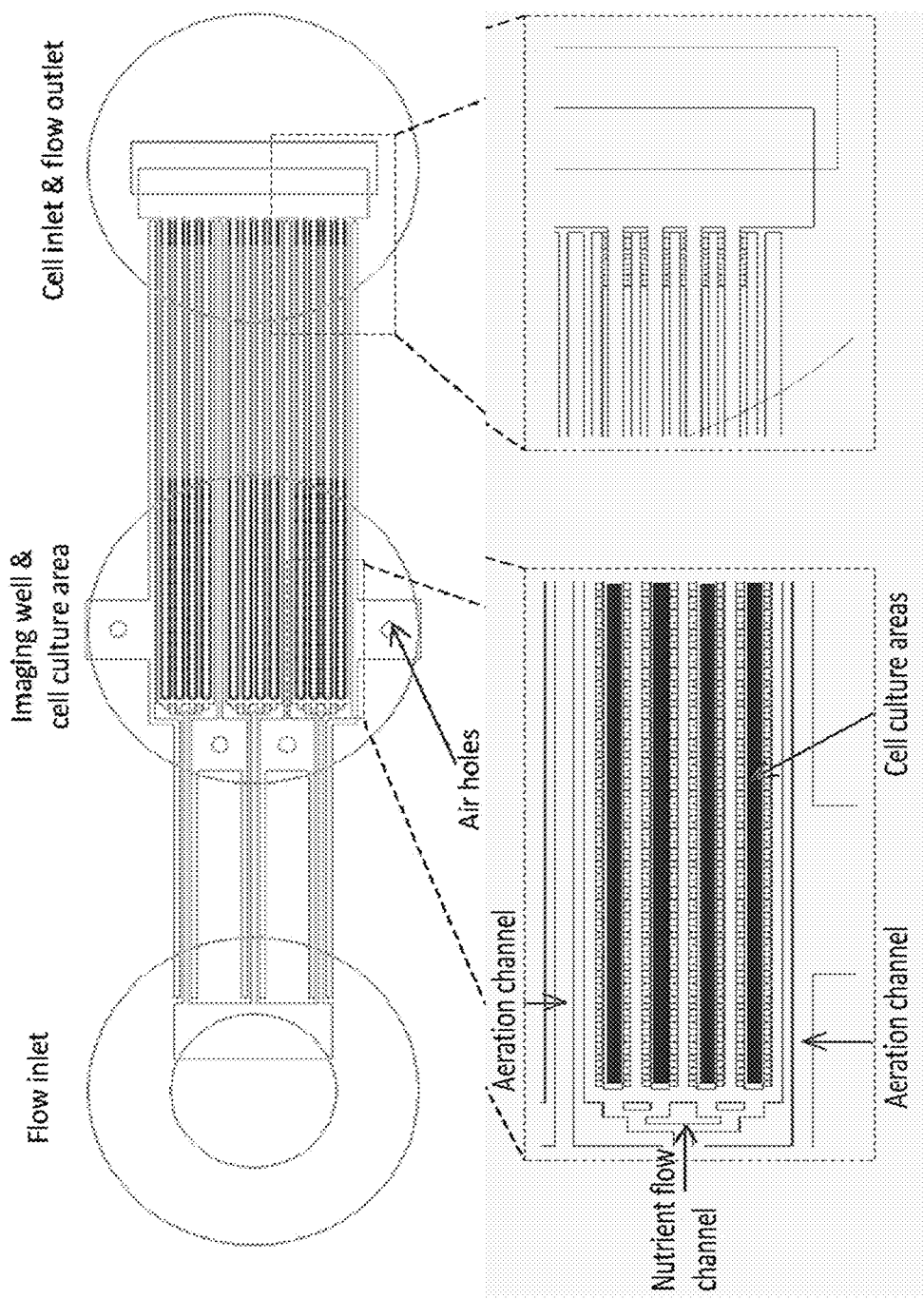
FIG. 8 is a schematic showing three blocks of four long cell culture sinusoids, where the long cell sinusoids extend across two wells, and further shows a rectangular cell inlet region/flow outlet region, and four air holes connecting to four air channels.

FIG. 8 is a schematic showing three blocks of four long cell culture sinusoids, where the long cell sinusoids extend across two wells, and further shows a rectangular cell inlet region/flow outlet region, and four air holes connecting to four air channels.

Figure 9A:
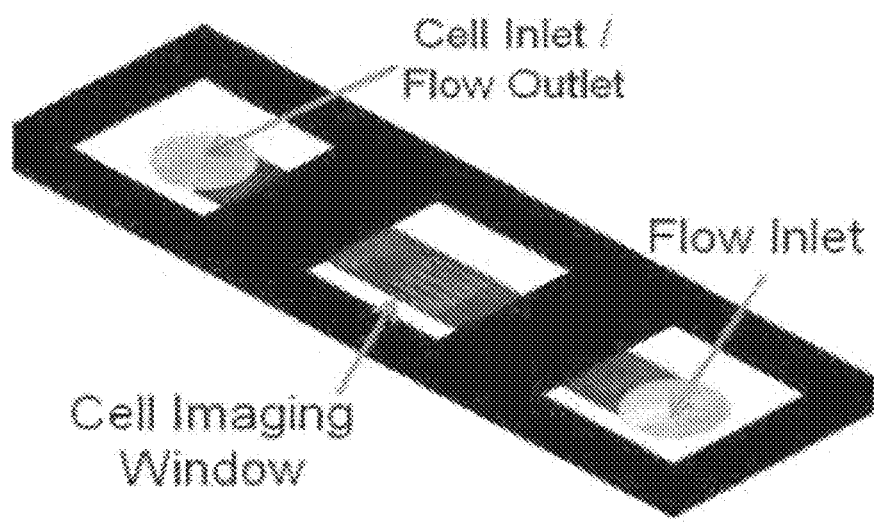
FIG. 9A-B are simplified schematic diagrams illustrating in three dimensions the components of a multi cell (e.g., 3) microfluidic system including a representation of the well frame according to specific embodiments of the invention.
Figure 9B:
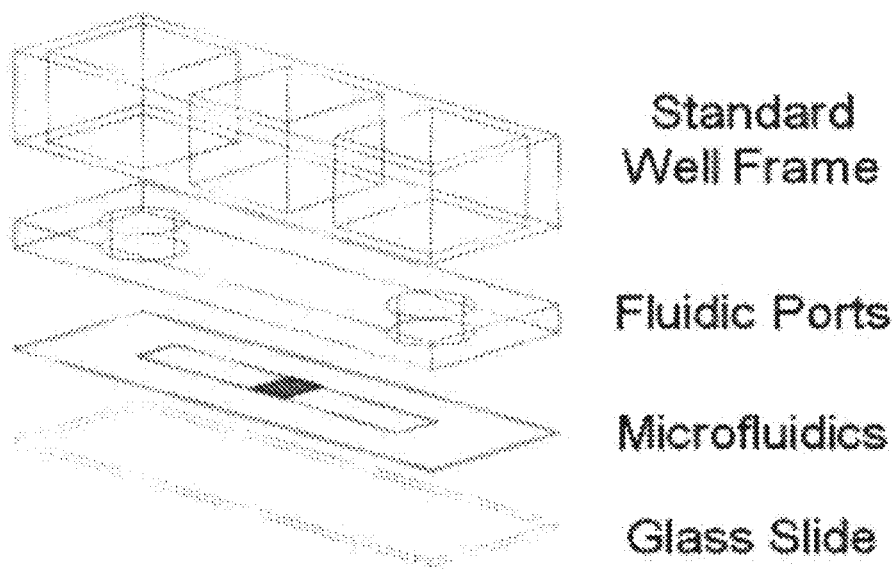

FIG. 9A-B are simplified schematic diagrams illustrating in three dimensions the components of a multi cell (e.g., 3) microfluidic system including a representation of the well frame according to specific embodiments of the invention.

Figure 10:
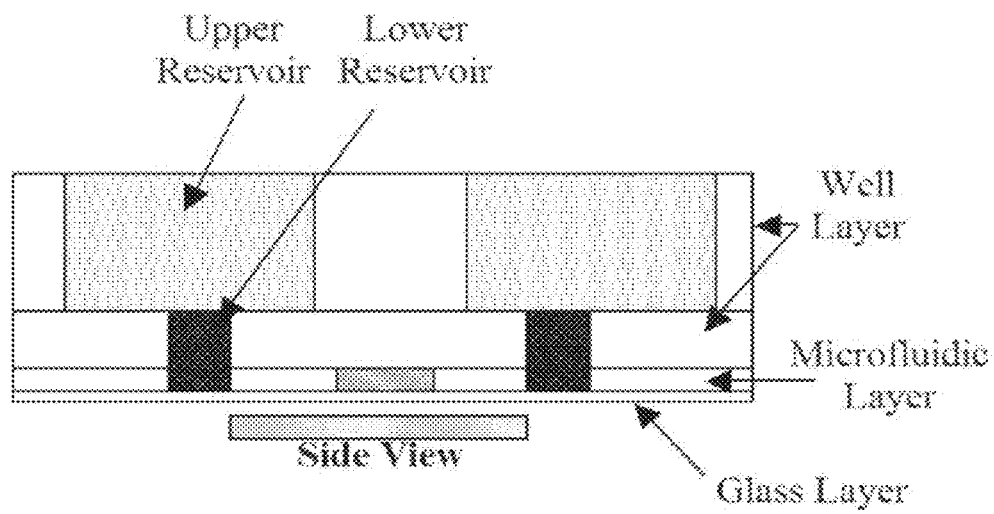
FIG. 10 is a simplified side view showing a structure according to specific embodiments of the invention illustrating two wells that are used in cell flow and fluid flow.

FIG. 10 is a simplified side view showing a structure according to specific embodiments of the invention illustrating two wells that are used in cell flow and fluid flow.

Figure 11:
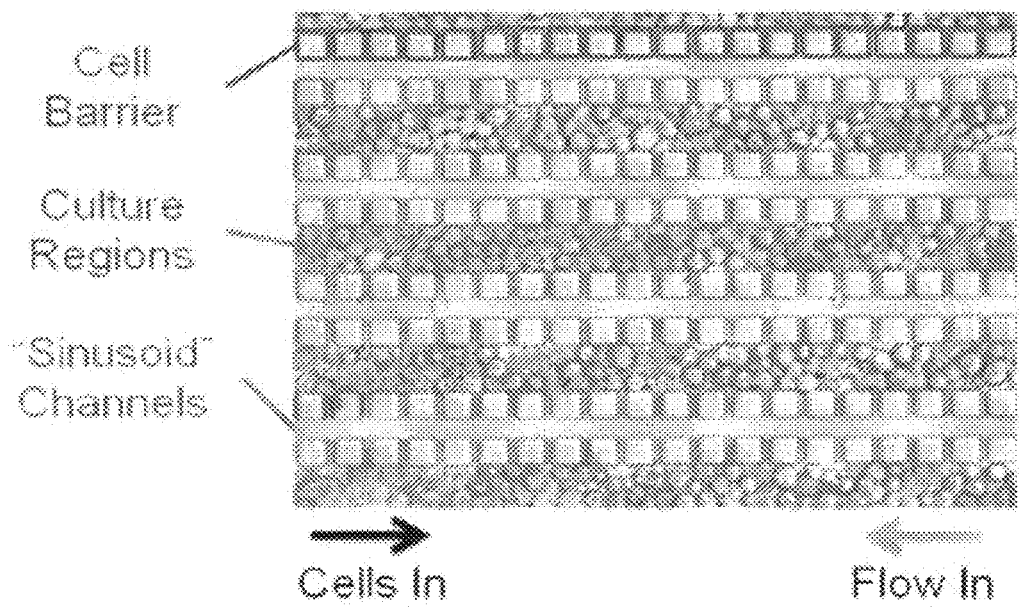
FIG. 11 is a close-up micrograph showing cells loaded in five sinusoid cell culture regions with four sinusoid channels between according to specific embodiments of the invention.

FIG. 11 is a close-up micrograph showing cells loaded in five sinusoid cell culture regions with four sinusoid channels between according to specific embodiments of the invention.

Figure 12:
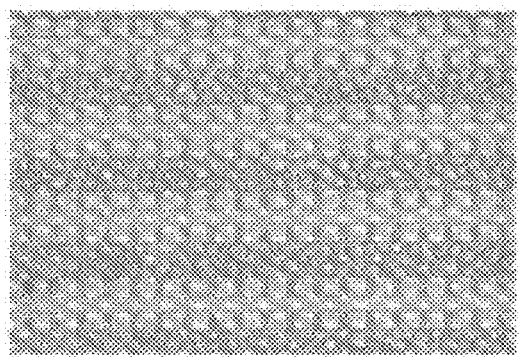
FIG. 12 shows four close-up micrographs showing cells loaded in four different sized sinusoid cell culture regions according to specific embodiments of the invention.
Figure 12:
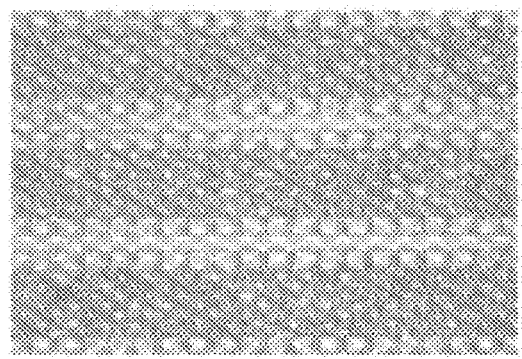
Figure 12:
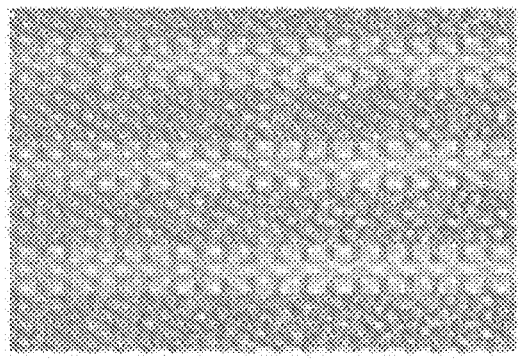
Figure 12:
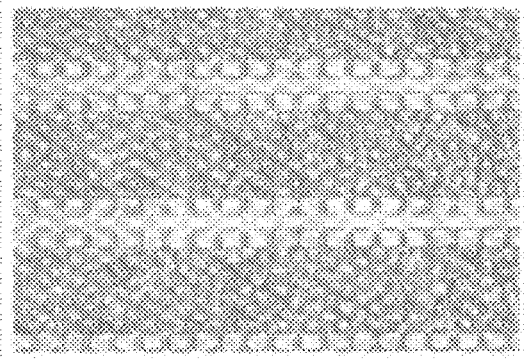

FIG. 12 shows four close-up micrographs showing cells loaded in four different sized sinusoid cell culture regions according to specific embodiments of the invention.

Thus, the present invention according to specific embodiments of the invention provides a number of novel improved microfluidic configurations. In a first aspect, three wells are used for each otherwise independent cell culture system. In a second aspect, artificial sinusoids with artificial epithelial barriers are provided with just one (optionally shared or multiplexed) fluidic inlet and one (optionally shared or multiplexed) fluidic output, where the medium output also functions as a cellular input. In a third aspect, artificial sinusoids with artificial epithelial barriers with just one fluidic inlet and one fluidic output are divided into blocks with air channels provided between blocks. In a fourth aspect, air holes are provided in the well chamber above the cell culture area of a microfluidic cellular culture array, where the medium output also functions as a cellular input. In a fifth aspect, a multiplexed medium inlet structure and multiplexed cellular input structure are provided to connect inputs and outputs to blocks of artificial sinusoids. In a sixth aspect, a multiplexed medium inlet structure and larger shared cellular input structure are provided to connect inputs and outputs to blocks of artificial sinusoids. In a seventh aspect, artificial sinusoids are configured with non-open portions of an epithelial barrier to better localize cells, and with perfusions inlets surrounding a cell culture area and optionally also present near a cell inlet area of the sinusoid. In an eighth aspect, longer artificial sinusoid chambers are provided.

As discussed elsewhere, various modifications may be made to the cell-culture area as described above. Various configurations are possible for the epithelial barrier, such as a grid-like passage structure. Other variations will be suggested to those of skill in the art having the teachings provided herein.

The structures disclosed above can also be adapted to systems using more or fewer wells on a standard microtiter well plate, such as those described in referenced documents and in other examples herein.

3. Example Device Operation

Figure 13:
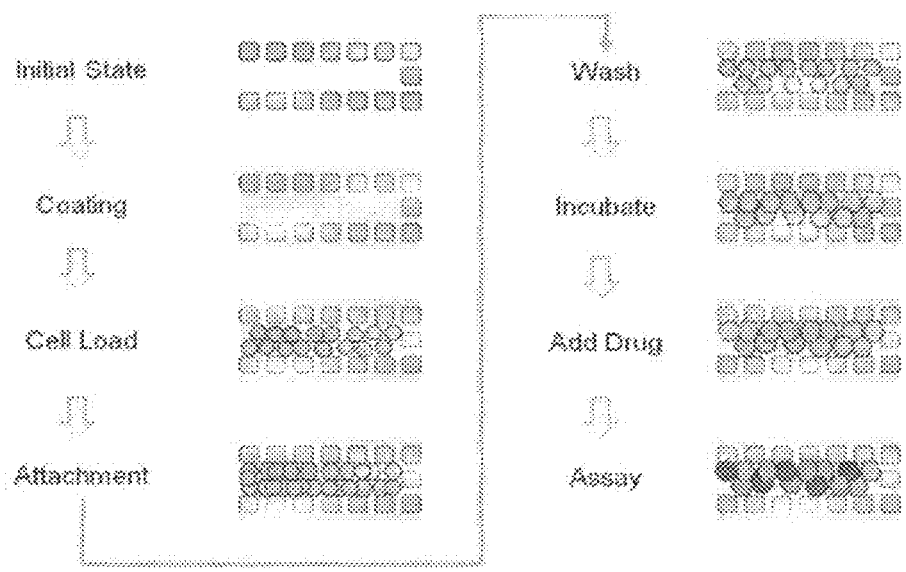
FIG. 13 is a schematic diagram showing steps from an empty culture region to performing a cell assay according to specific embodiments of the invention.

FIG. 13 is a schematic diagram showing steps from an empty culture region to performing a cell assay according to specific embodiments of the invention. Various novel aspects according to specific embodiments of the invention simplify these steps and allow them to be automated.

Cell Loading

Cell loading in specific embodiments of the invention can utilize the rapid surface tension flow between the cell inlet and the flow inlet. In this method, the cell inlet reservoir (upper and lower) is aspirated of its priming solution. Then, the flow inlet upper reservoir is aspirated. An amount (e.g., Five microliters) of cell suspension (e.g., trypsinized HeLa human cancer cell line, 5×10 5 cells/ml) is dispensed into the cell inlet lower reservoir. The flow inlet lower reservoir is aspirated, causing liquid to flow from cell inlet to flow inlet via surface tension/capillary force. Cell loading in various configurations can be completed in approximately 2-5 minutes. The cell loading reservoir is then washed with medium (e.g., Dulbecco's Modified Eagle's Medium, DMEM) and filled with e.g., 50-100 microliters of clean medium. At this state, the plate is was placed in a controlled culture environment for a period (e.g., 37 C., 5% $CO_2$ incubator for 2-4 hours) to allow for cell attachment.

While such loading is effective for some microfluidic cell culture devices, in a presently preferred embodiment, a proprietary pneumatic manifold, as described elsewhere herein, is mated to the plate and pneumatic pressure is applied to the cell inlet area for more effective cell loading. For particular cell systems, it has been found that overall cell culture area design can be made more effective when it is not necessary to allow for passive cell loading.

Figure 14B:
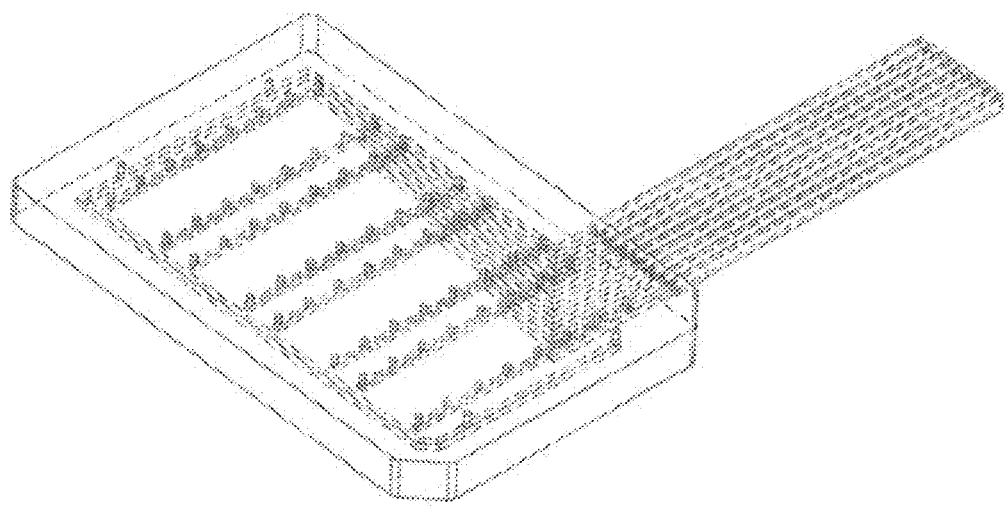
FIG. 14A-C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped.
Figure 14C:
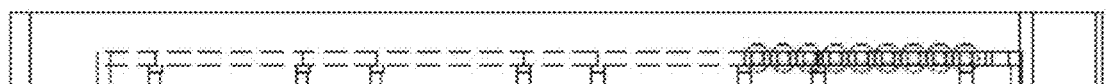
Figure 14A:
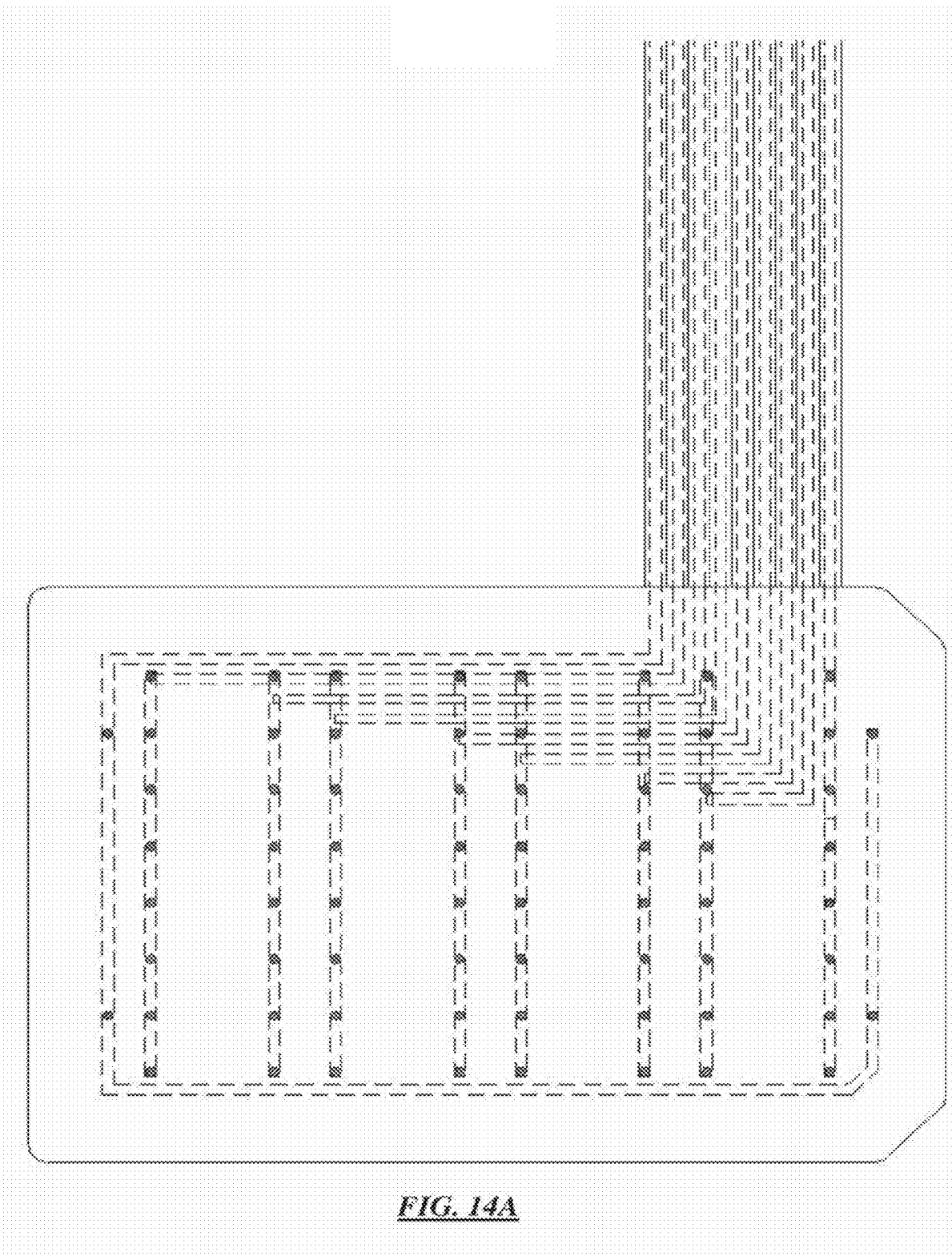

FIG. 14A-C shows a top view, side view, and plan view of a schematic of an example manifold according to specific embodiments of the invention. In this example, the eight tubing lines to the right are for compressed air, and each is configured to provide pressure to a column of cell inlet wells in a microfluidic array. The left-most line in the figure is for vacuum and connects to an outer vacuum ring around the manifold. Each column of wells is generally connected to a single pressure line with wells above imaging regions skipped. The manifold is placed on top of a standard well plate. A rubber gasket lies between the plate and manifold, with holes matching the manifold (not shown). The vacuum line creates a vacuum in the cavities between the wells, holding the plate and manifold together. Pressure is applied to the wells to drive liquid into the microfluidic channels (not shown). A typical pressure of 1 psi is used, therefore the vacuum strength is sufficient to maintain an air-tight seal. In one example there are 9 tubing lines to the pressure controller: 8 lines are for compressed air and 1 line is for vacuum (leftmost). In specific example embodiments, each column is connected to a single pressure line. Columns above the cell imaging regions are skipped.

Pressurized cell loading in a system according to specific embodiments of the invention has been found to be particularly effective in preparing cultures of aggregating cells (e.g., solid tumor, liver, muscle, etc.). Pressurized cell loading also allows structures with elongated culture regions, e.g., as shown in FIG. 7 and FIG. 8, to be effectively loaded. Use of a pressurized manifold for cell loading and passive flow for perfusion operations allows the invention to utilize a fairly simple two inlet design, without the need for additional inlet wells and/or valves as used in other designs.

Fluid Flow and Operation: Gravity and Surface Tension Flow

The format of the microfluidic plate design allows two automation-friendly flow modalities dependent on the extent of dispensing/aspiration. The first is surface tension mediated flow. In this case, when the lower reservoir is aspirated in either one of the wells, the capillary force of the fluid/air interface along with the wetted surfaces (glass, silicone, acrylic) will rapidly draw liquid in from the opposing well until the lower reservoir is filled (or in equilibrium with the opposing lower reservoir). This effect is useful for microfluidic flows as it is only evident when the reservoir diameter is small and the flow volumes are small. In an example array design, the lower reservoir wells are 1-2 mm in diameter, and with a total flow volume of approximately 3-5 microliters. Since the microfluidic channel volume is only 0.2 microliters, this mechanism is well suited for cell loading and cell exposures.

The second mechanism is gravity driven perfusion, which is well suited for longer term flows, as this is dependent on the liquid level difference and not the reservoir dimensions. According to specific embodiments of the invention, this may be accomplished by adding more liquid into one reservoir (typically filling near the top of the upper reservoir). The fluidic resistance through the microfluidic channels will determine how long (e.g., 24 hours) to reach equilibrium between the wells and thus determine how often wells should be refilled.

Figure 15:
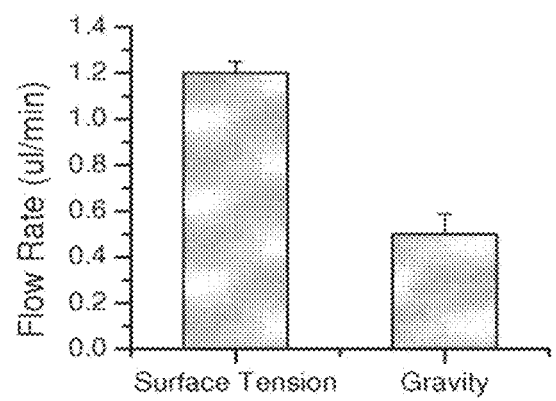
FIG. 15 is a graph illustrating an example of flow rate difference between a surface tension mechanism and a gravity driven mechanism according to specific embodiments of the invention.

FIG. 15 shows the flow rate difference between the surface tension mechanism and the gravity driven mechanism. For the surface tension flow, in an example, 5 microliters was dispensed into the lower reservoir followed by aspiration of the opposing lower reservoir. For the gravity flow, a liquid level difference of 2.5 mm was used, with both wells filled into the upper reservoir portion.

Changing Gravity Flow Rate via Liquid Level

Figure 16:
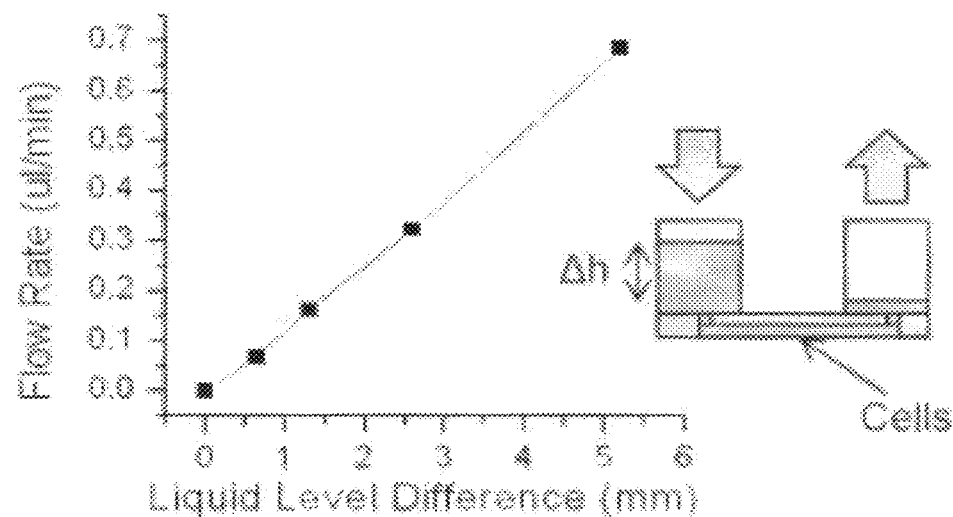
FIG. 16 is a graph illustrating an example of the extent to which gravity perfusion rate is responsive to the liquid level difference between the two upper reservoir wells according to specific embodiments of the invention.

The gravity perfusion rate is also responsive to the liquid level difference between the two upper reservoir wells as illustrated in FIG. 16. This fact allows an automated dispenser/aspirator to control and maintain a given perfusion flow rate over a 10-fold range during culture. Here, different liquid level differences were produced via dispensing volumes and measured for volumetric flow rate.

Controlling Gravity Perfusion Rate Via Plate Tilt Angle

Figure 17A:
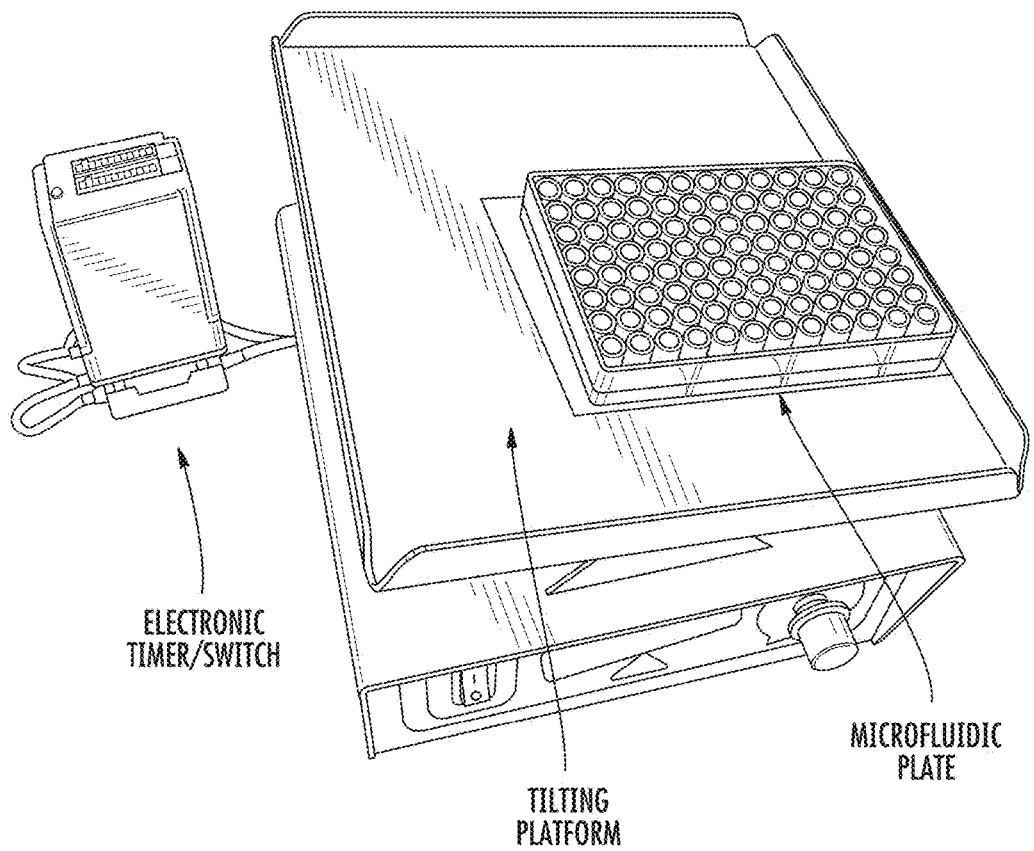
FIG. 17A-B illustrate a tilting platform that can be used to control the liquid height difference between the inlet/outlet wells in a device or system according to specific embodiments of the invention and an example of flow rate versus plate tilt angle.
Figure 17B:
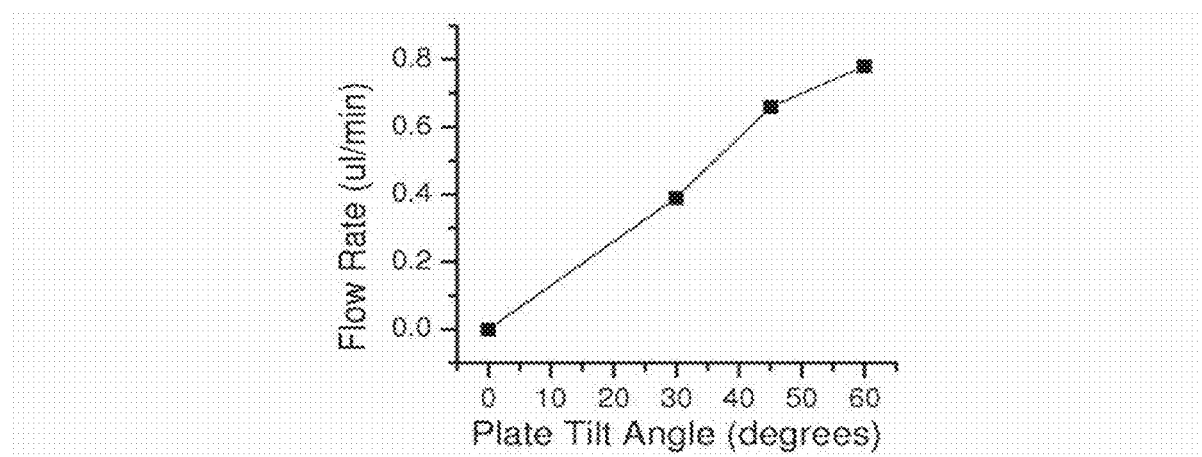

According to specific embodiments of the invention, the liquid height difference between the inlet/outlet wells across the plate can also be precisely controlled using a mechanical tilting platform. In this implementation, it is possible to maintain a constant flow rate over time, as well as back-and-forth flow with different forward and reverse times (i.e. blood flow). In the example illustrated in FIG. 17, both inlet and outlet reservoirs were filled with 50 microliters of solution. On a flat surface, there is no flow through the channels, and as the angle is increased, so is the flow rate. The photo shows a prototype controlled tilting platform, consisting of a mechanical platform, and an electronic switch.

In an example system, perfusion cell culture can be initiated by filling the flow inlet reservoir with 200-300 microliters of fresh medium (e.g., DMEM supplemented with 10% fetal bovine serum) and aspirating the cell inlet upper reservoir. The liquid level difference between the flow inlet and cell inlet wells will then cause a continuous gravity driven flow through the attached cells. For sustained culture, the flow inlet well is refilled and the cell inlet well aspirated during a period depending on fluidic resistance and reservoir volumes (e.g., every 24 hours).

Cell Assay and/or Observation

Cell assay can be performed directly on the microfluidic cell culture using standard optically based reagent kits (e.g. fluorescence, absorbance, luminescence, etc.). For example a cell viability assay utilizing conversion of a substrate to a fluorescent molecule by live cells has been demonstrated (CellTiter Blue reagent by Promega Corporation). The reagent is dispensed into the flow inlet reservoir and exposed to the cells via gravity perfusion over a period of time (e.g., 21 hours). For faster introduction of a reagent or other fluid, the new fluid can be added to the flow inlet reservoir followed by aspiration of the cell inlet reservoir.

Data can be collected directly on the cells/liquid in the microfluidic plate, such as placing the plate into a standard fluorescence plate reader (e.g., Biotek Instruments Synergy 2 model). In some reactions, the substrate may diffuse into the outlet medium, and therefore be easily detected in the cell inlet reservoir. For cell imaging assays, the plate can be placed on a scanning microscope or high content system. For example, an automated Olympus IX71 inverted microscope station can be used to capture viability of cultured liver cells with a 20× objective lens.

By repeatedly filling/aspirating the wells, cells can be maintained for long periods of time with minimal effort (e.g. compared to standard "bioreactors" which require extensive sterile preparation of large fluid reservoirs that cannot be easily swapped out during operation).

4. Automated Systems

Figure 18:
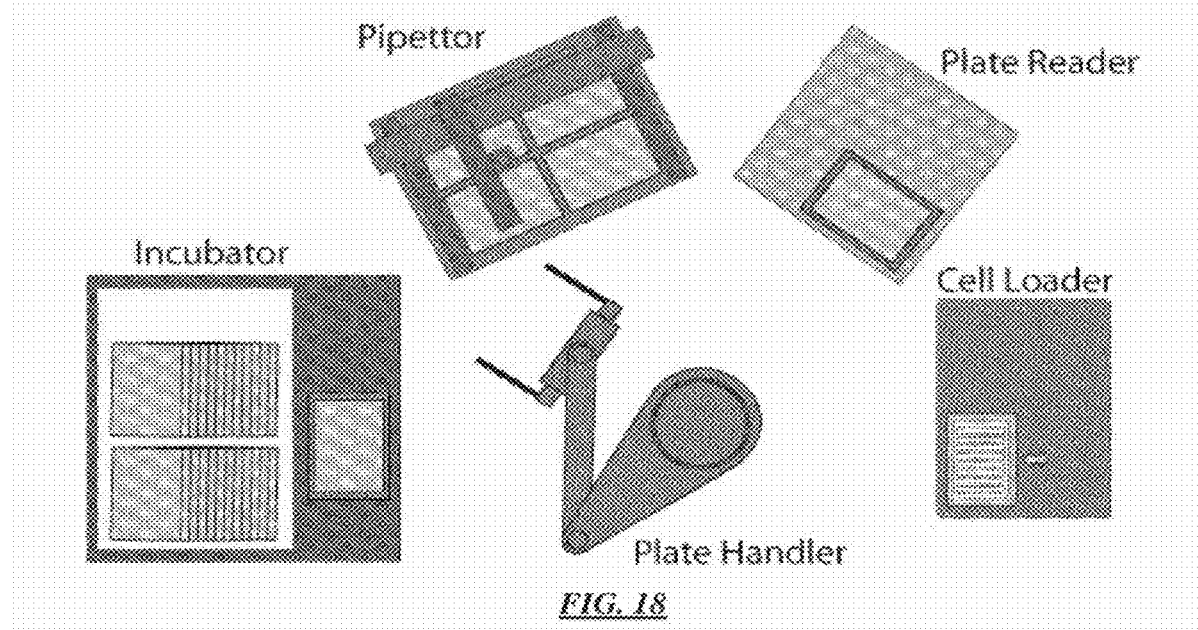
FIG. 18 illustrates a top view schematic of an example cell culture automation system according to specific embodiments of the invention.

FIG. 18 illustrates a top view schematic of an example cell culture automation system according to specific embodiments of the invention. Because the plates are designed to be handled using SBS compliant instruments, various "off-the-shelf" machines can be used to create an automated system. This schematic shows an example of how this is accomplished. A robotic arm (plate handler) moves the microfluidic plates from station to station. An automated incubator stores the plates at the proper temperature and gas environment for long term perfusion via gravity flow. The pipettor dispenses liquids (media, drugs, assay reagents, etc.) to the inlet wells and removes liquid from the outlet wells. A plate reader is used for assay. The cell loader is optionally used to introduce the cells to the microfluidic arrays at the beginning of the experiment. The cell loader in particular is generally not "off-the-shelf" and operates by applying pneumatic pressure to specified wells of the array plate to induce flow. Standard or custom computer software is available to integrate operations.

Figure 19:
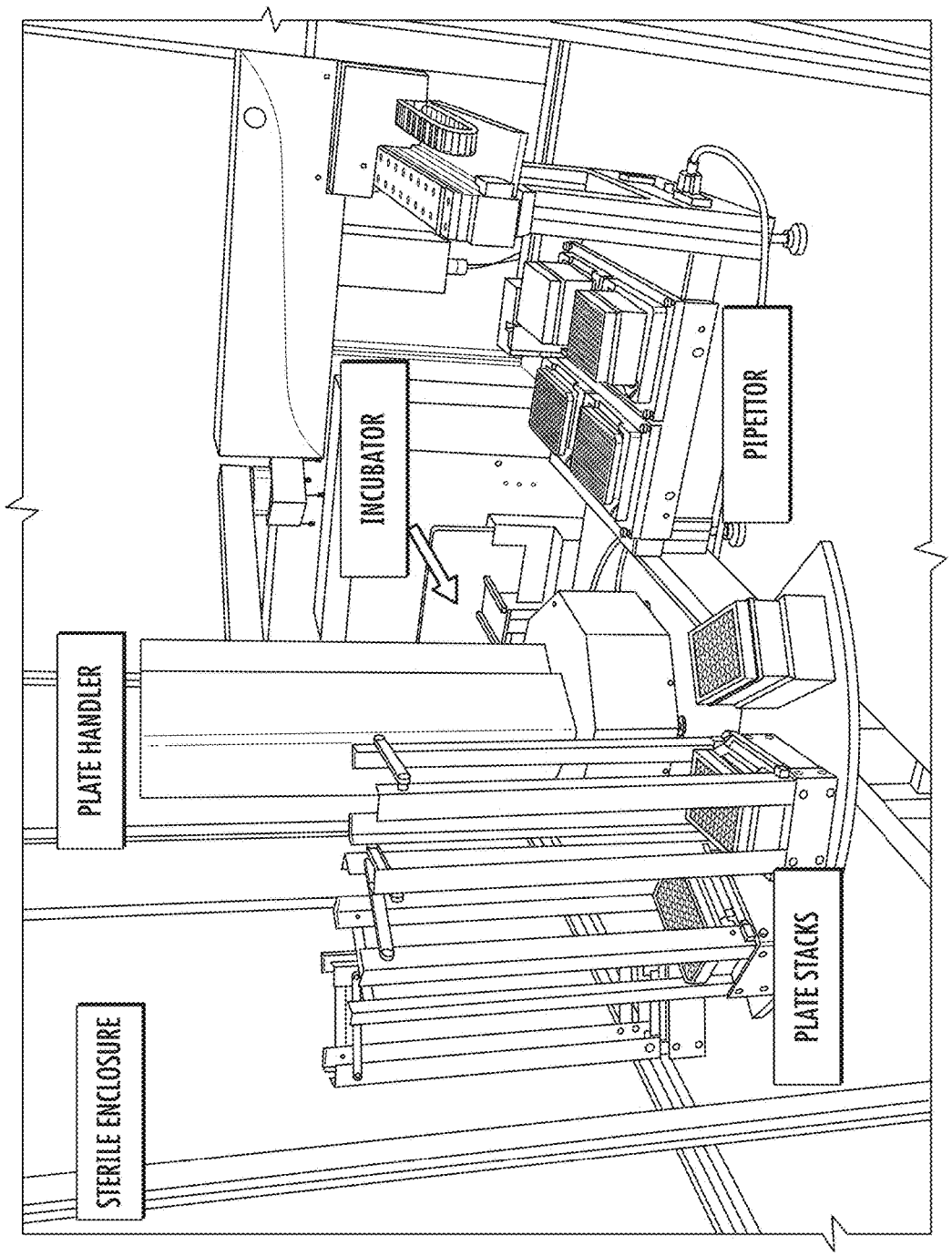
FIG. 19 is a photograph of an example automated microfluidic perfusion array system according to specific embodiments of the invention.

FIG. 19 is a photograph of an example automated microfluidic perfusion array system according to specific embodiments of the invention. The basic process includes: 1) removing the plate from the incubator, 2) removing liquid from the outlet wells via the pipettor, 3) moving a media/drug storage plate from the "plate stacks," 4) transferring liquid from the media/drug plate to the microfluidic plate via the pipettor, 5) placing the microfluidic plate into the incubator, 6) repeat for each plate, 7) repeat after specified time interval (e.g. 24 hours).

Figure 20:
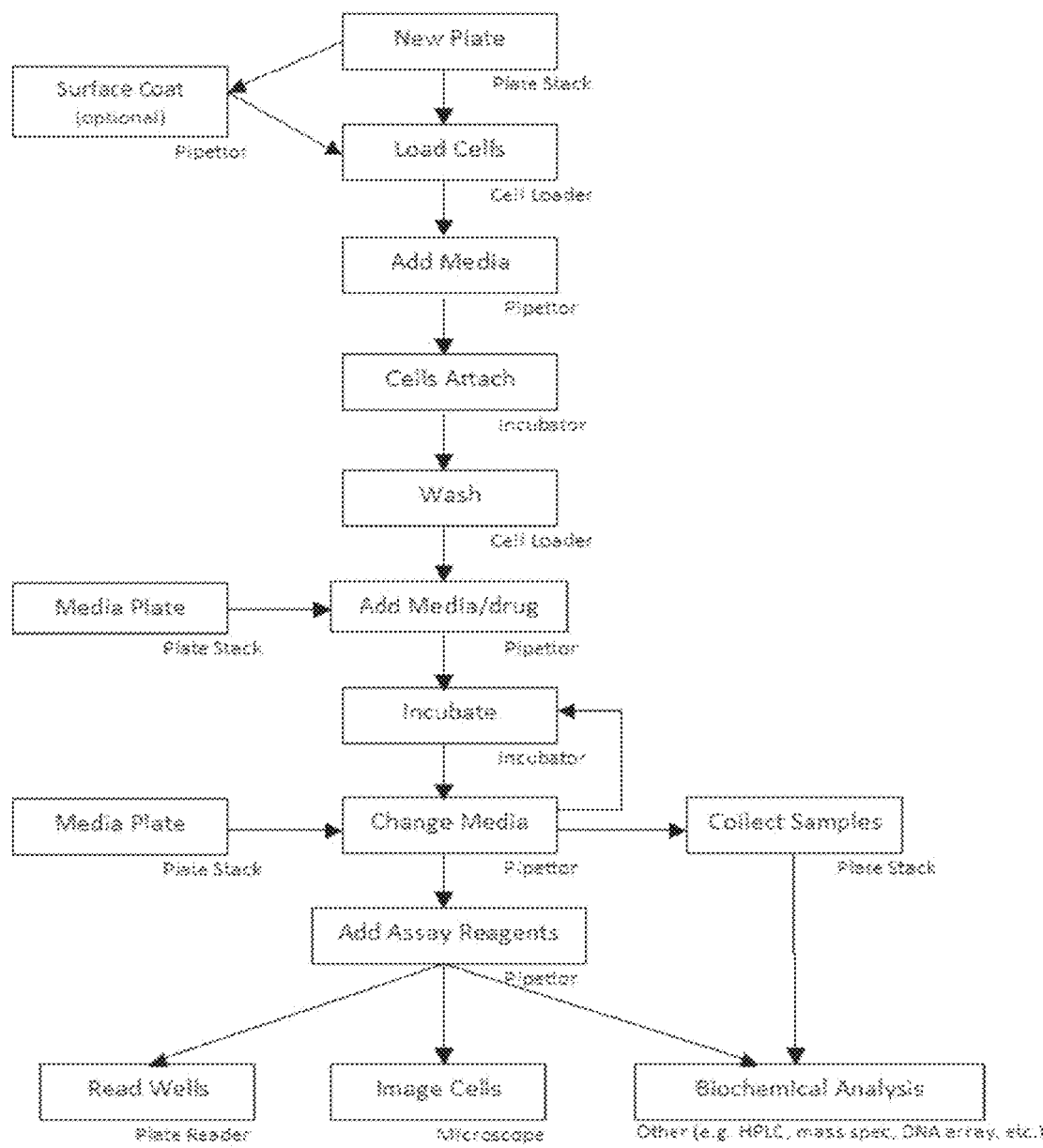
FIG. 20 is a flow chart illustrating the process flow of typical operation steps.

FIG. 20 is a flow chart illustrating the process flow of typical operation steps. This figure illustrates, as an example, automated process steps an indicates an automated device that is used to perform such a step. A standard automated pipettor is used for an optional surface coating, to add cells in suspension, to add media or drugs or reagents, and to change media. Known automated pipettors can individually deliver or withdraw fluids from specified wells. In a specific embodiment, a proprietary cell loader is used to pressurize the cell inlet wells for cell loading. After a period in an incubator designed for optimal cell attachment, the cell loader can again be used to wash fluid and unattached cells from the microfluidic culture areas. One or more reading or analysis devices is used to assay the cells.

Figure 21:
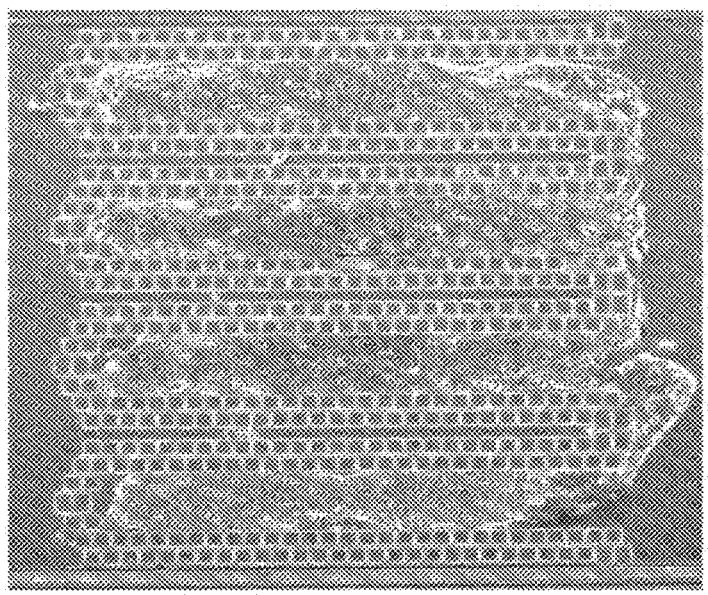
FIG. 21 illustrates four microfluidic culture areas from an example array plate prepared in the example system described above using primary rat hepatocytes.
Figure 21:
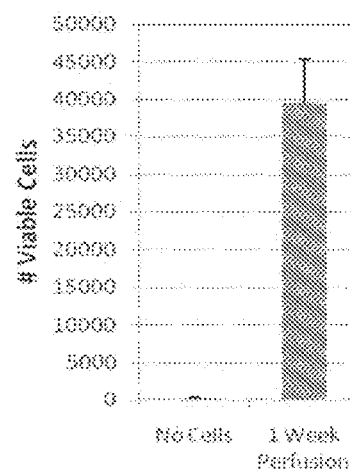

FIG. 21 illustrates four microfluidic culture areas from an example array plate prepared in the example system described above using primary rat hepatocytes. The cells were cultured for 1 week with medium changed at a rate of 150 ul per unit, twice a day. Cells were assayed at the end of 7 days for viability using the Cell Titer Blue Kit from Promega, and read on an automated fluorescence plate reader (Biotek Synergy). In this figure, an example microfluidic culture area uses a grid flow-through epithelial walls.

Figure 22:
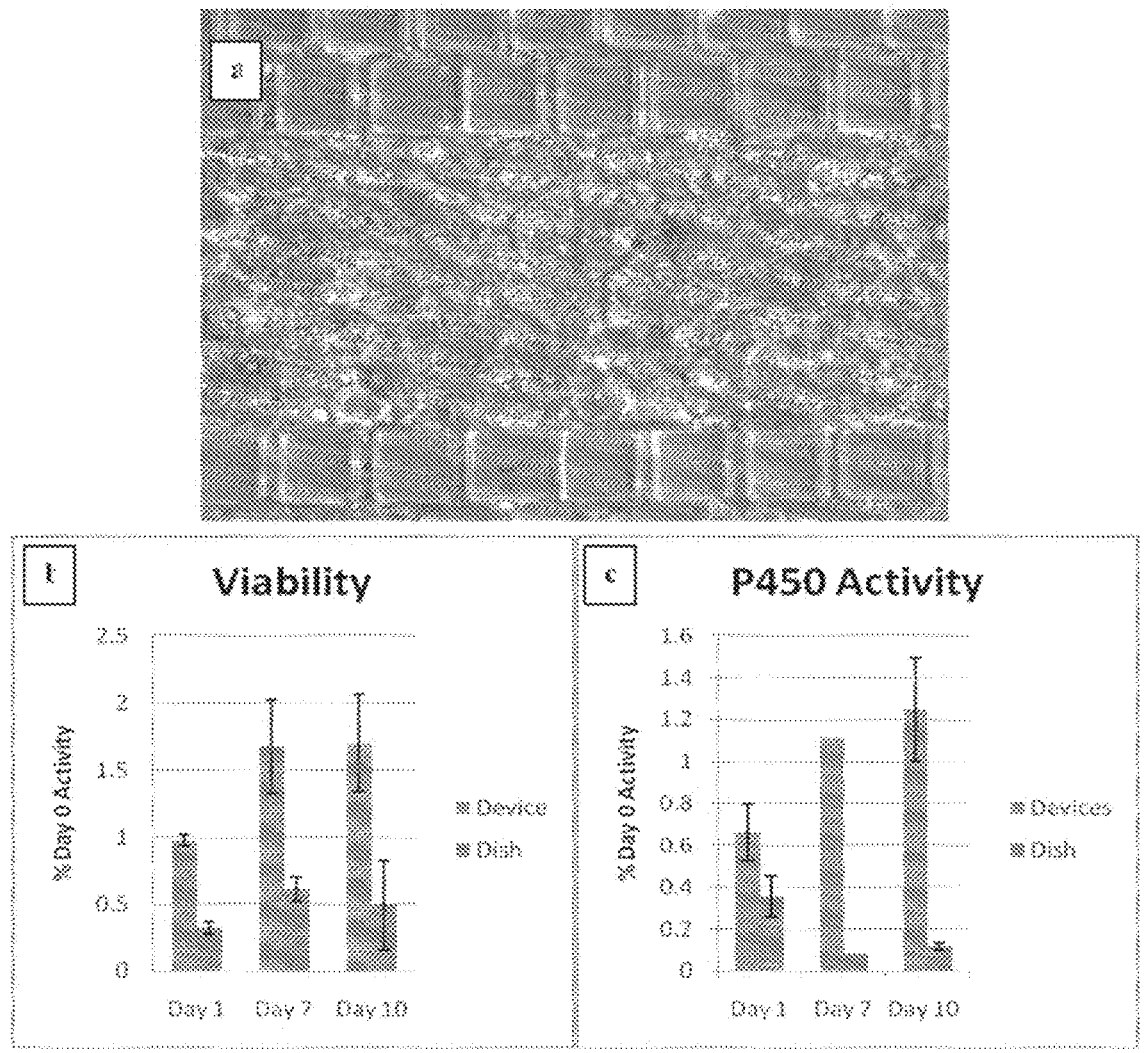
FIG. 22 illustrates a portion of a microfluidic culture area from an example array plate prepared in the example system described above using primary human hepatocytes.

FIG. 22 illustrates a portion of a microfluidic culture area from an example array plate prepared in the example system described above using primary human hepatocytes. The cells were cultured in the microfluidic array according to specific embodiments of the invention, showing (a) phase contrast of freshly isolated human hepatocytes cultured in the microfluidic device for 13 days. (b) Viability of human hepatocytes cultured in the microfluidic device and in a 96-well dish measured by the CellTiter Blue assay (Promega, Inc.). (c) P450 CYP3A4 activity of cultured hepatocytes in the microfluidic device and 96-well dish measured via the P450-Glow assay (Promega, Inc.).

Figure 23:
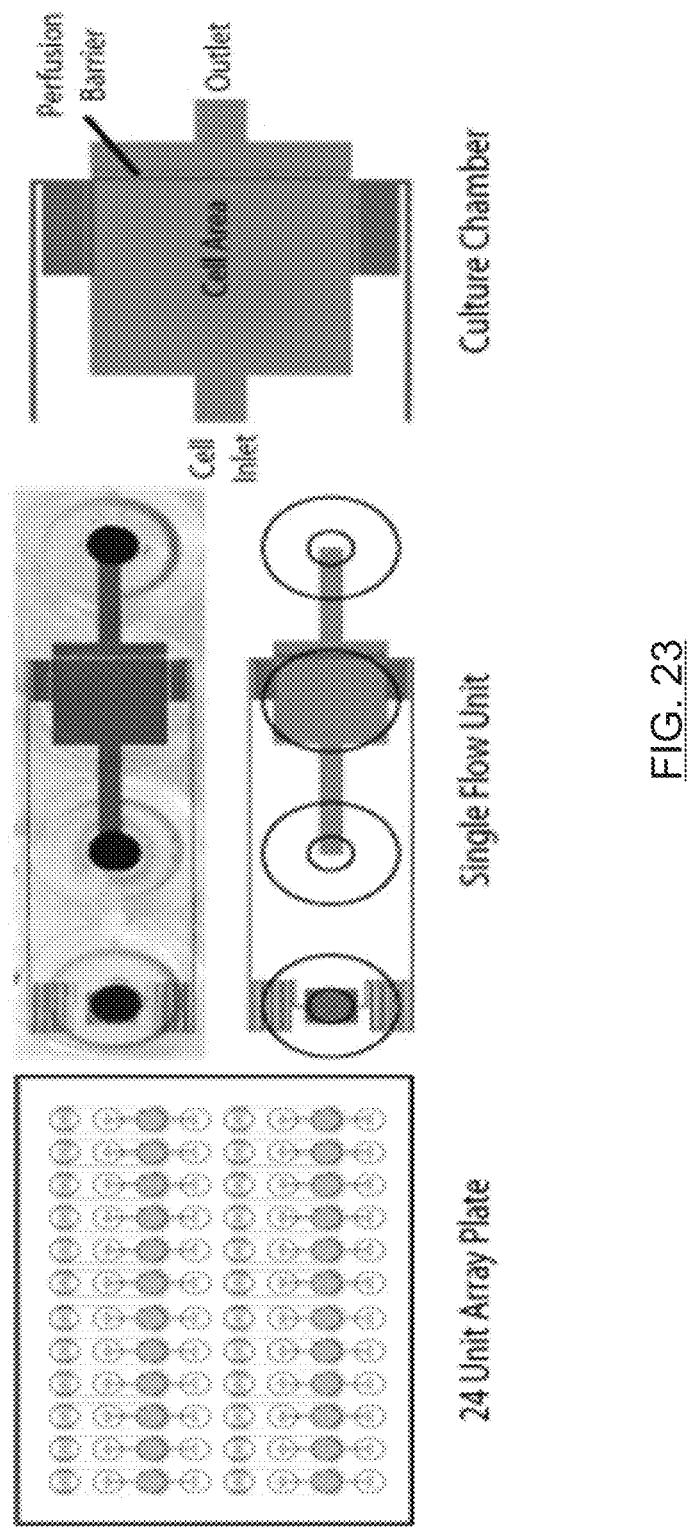
FIG. 23 illustrates a layout of another type of cell culture array designed for general cell culture automation according to specific embodiments of the invention.

FIG. 23 illustrates a layout of another type of cell culture array designed for general cell culture automation according to specific embodiments of the invention. In this design, each culture unit consists of 4 well positions. The first well is for perfusion medium, the second well is for cell inlet, the third well is for imaging the microfluidic chamber, and the fourth well is the outlet. A cell barrier/perfusion barrier localizes cells to the cell area and improves nutrient transport during continuous perfusion culture. The low fluidic resistance of the cell inlet to outlet path enables cells to be rapidly loaded via gravity or surface tension methods without an external cell loading mechanism. The high fluidic resistance of the perfusion inlet channels allows long term continuous perfusion of medium via gravity flow without any external pump mechanism.

Figure 24:
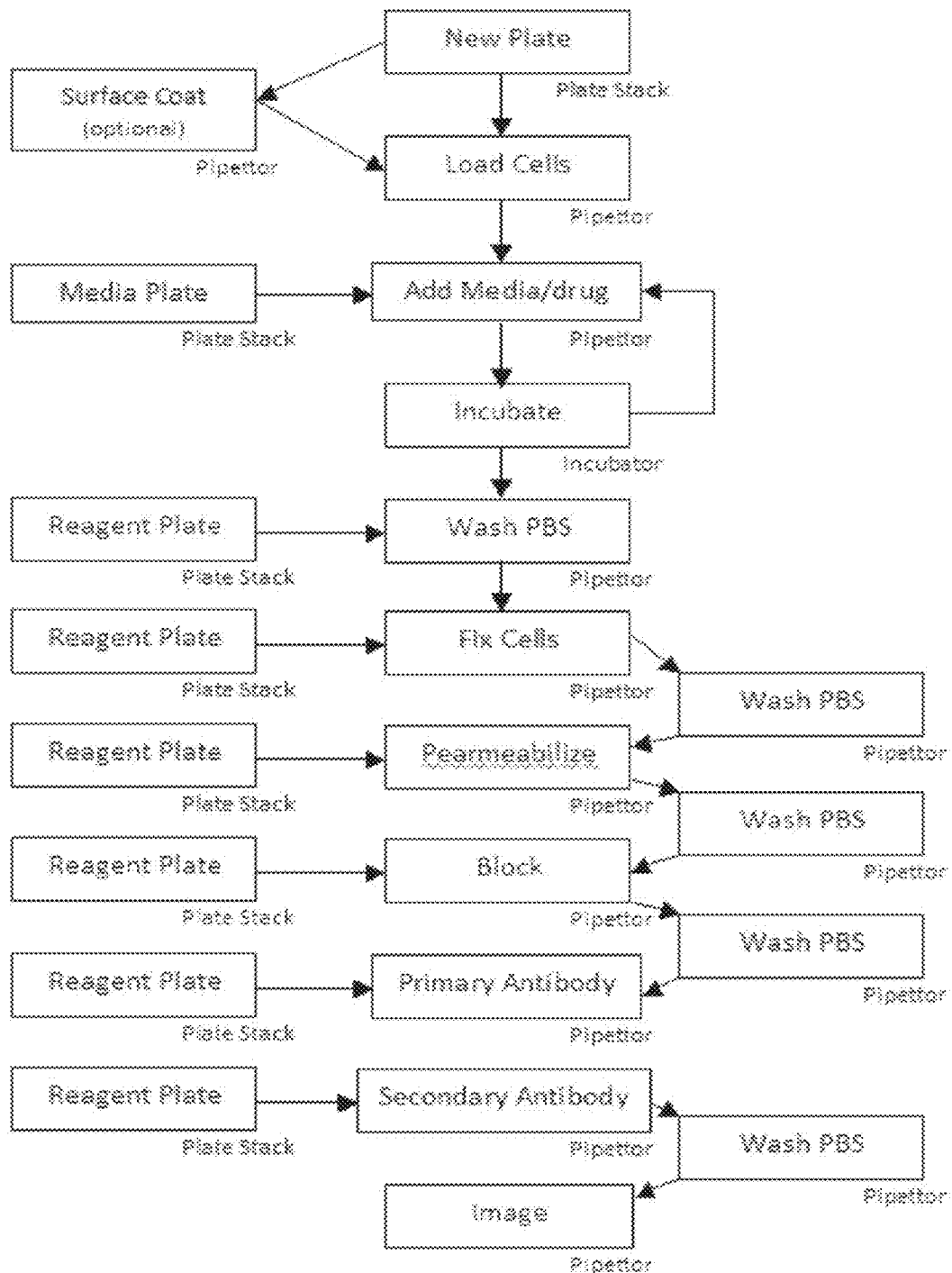
FIG. 24 illustrates an operation schematic for performing automated cell culture and immunostaining on a microfluidic array with gravity cell loading as described above. Example applications include stem cell culture and primary cell culture with immunofluorescence staining and microscopy.

FIG. 24 illustrates an operation schematic for performing automated cell culture and immunostaining on a microfluidic array with gravity cell loading as described above. Example applications include stem cell culture and primary cell culture with immunofluorescence staining and microscopy.

Figure 25:
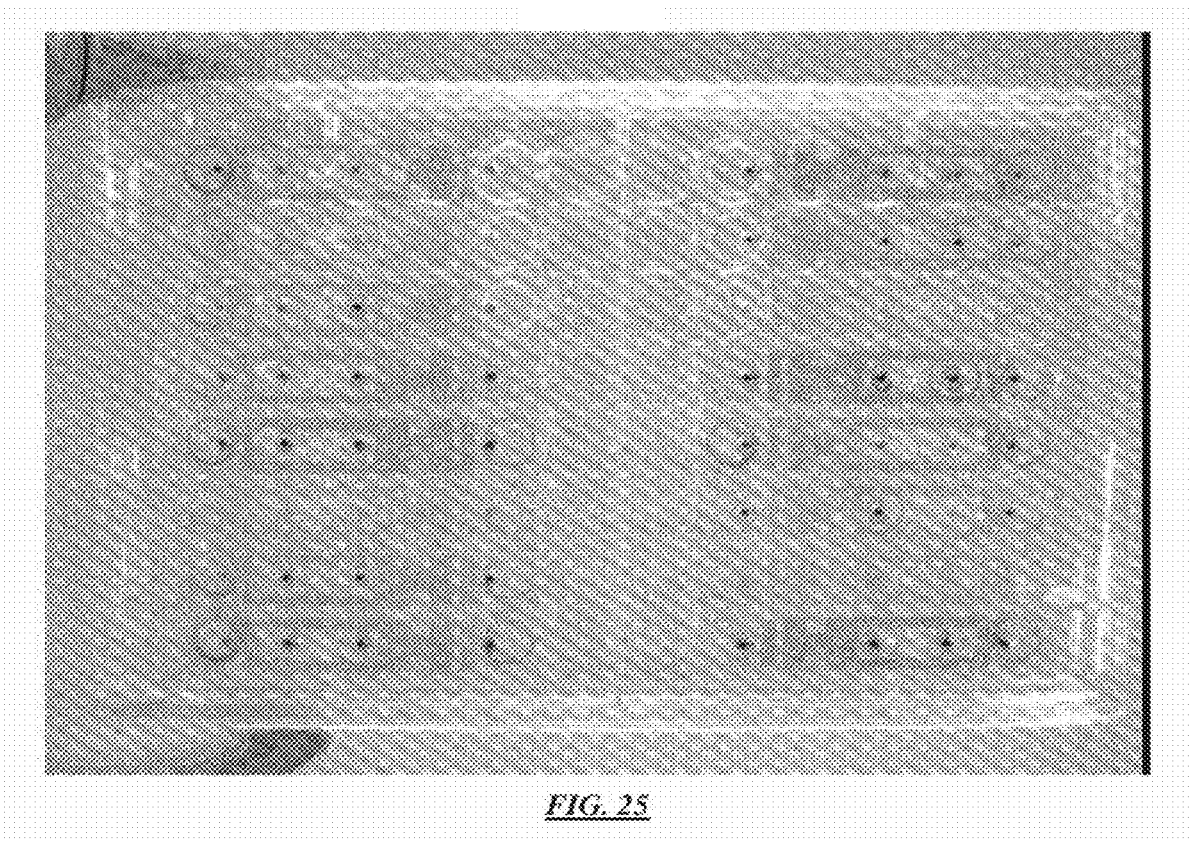
FIG. 25 illustrates an alternative example SBS (Society for Biomolecular Screening) standard microfluidic bioreactor array schematic.

FIG. 25 illustrates an alternative example SBS (Society for Biomolecular Screening) standard microfluidic bioreactor array schematic. A 16-unit microfluidic cell culture array filled with colored dyes so that microfluidic channels are visible. In this example, each unit occupies five wells, which from left to right are medium inlet, cell inlet, cell outlet, cell imaging, and medium outlet.

Figure 26A:
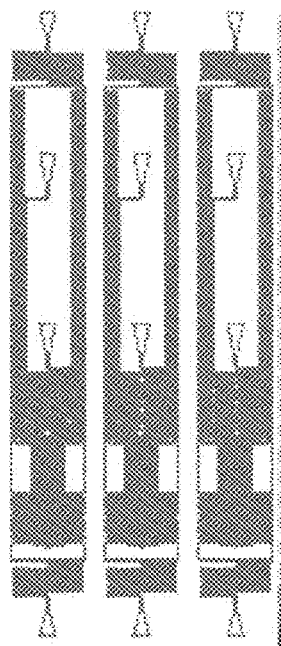
FIG. 26A-B illustrate an alternative cellular culture system assembly according to specific embodiments of the present invention showing (A) an example schematic microfluidics design for three cell units; (B) a soft lithography fabrication of this design with laser machining of four openings per culture unit.
Figure 26B:
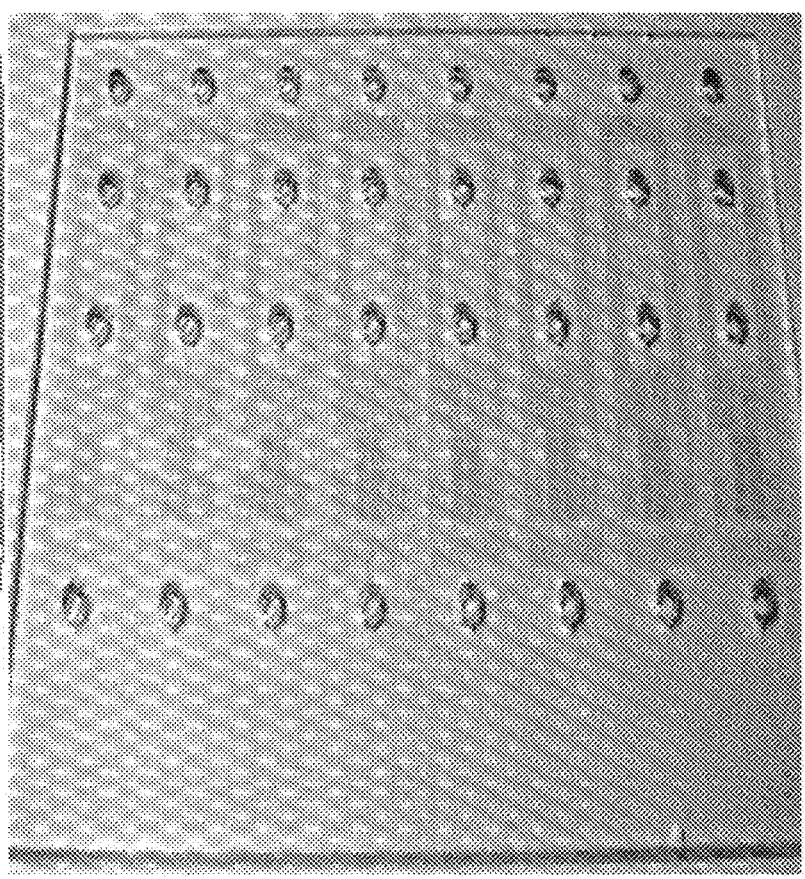

FIG. 26A-B illustrate an alternative cellular culture system assembly according to specific embodiments of the present invention showing (A) an example schematic microfluidics design for three cell units; (B) a soft lithography fabrication of this design with laser machining of four openings per culture unit. This design is attached to a microplate with wells for receiving medium and cells as described herein.

Figure 27:
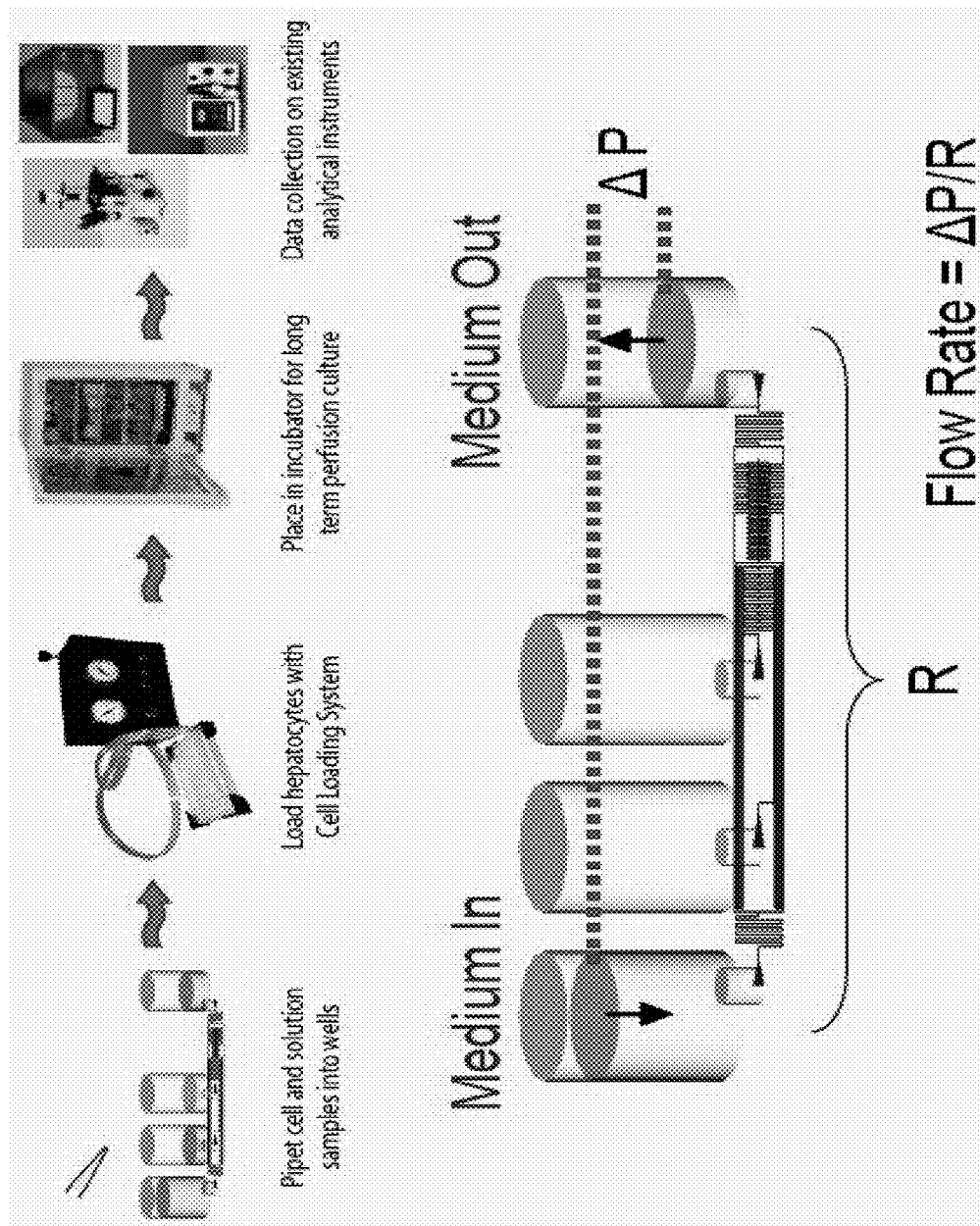
FIG. 27 illustrates operation steps of a less automated or prototype system according to specific embodiments of the invention.
Figure 28:
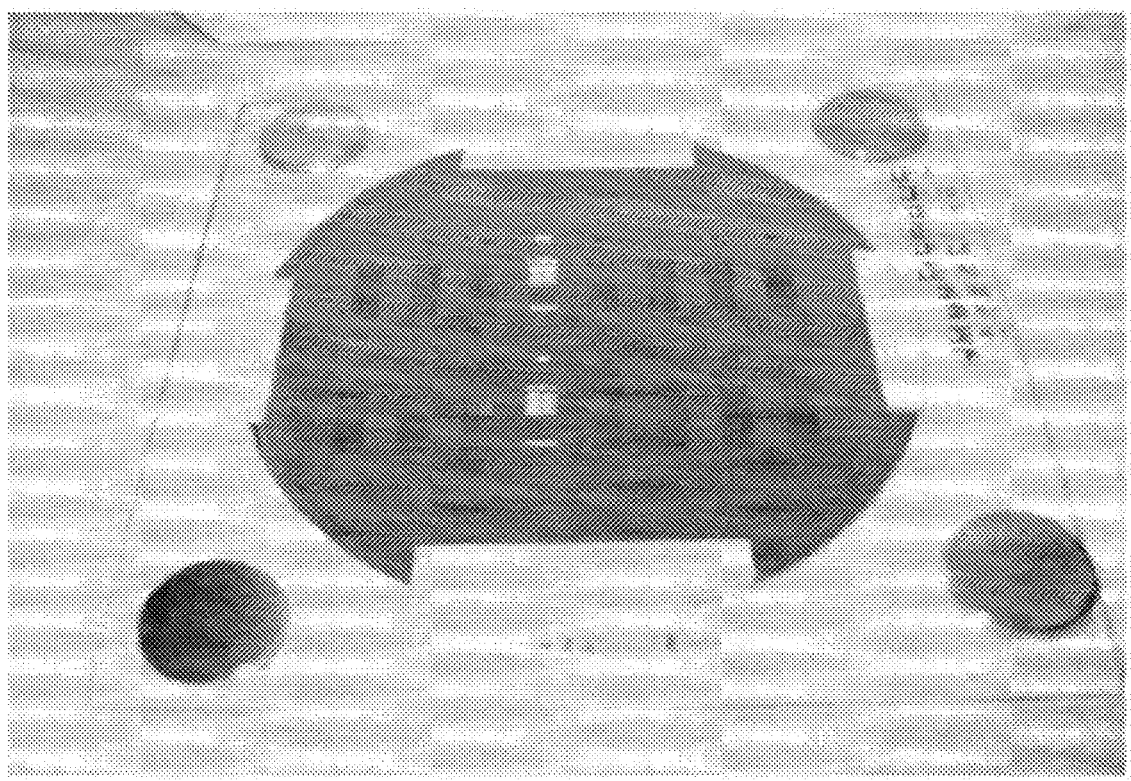
FIG. 28 illustrates a microfluidic mold fixed on glass plate with magnets according to specific embodiments of the invention. In one example embodiments, each magnet used is: ¾" Diameter×1/16" Thick fabricated, e.g., from sintered Neodymium-Iron-Boron (NdFeB) with a Plating/Coating of Ni—Cu—Ni (Nickel) and a Grade: N40 with a Pull Force of: 4.0 lbs (1814 g).
Figure 29:
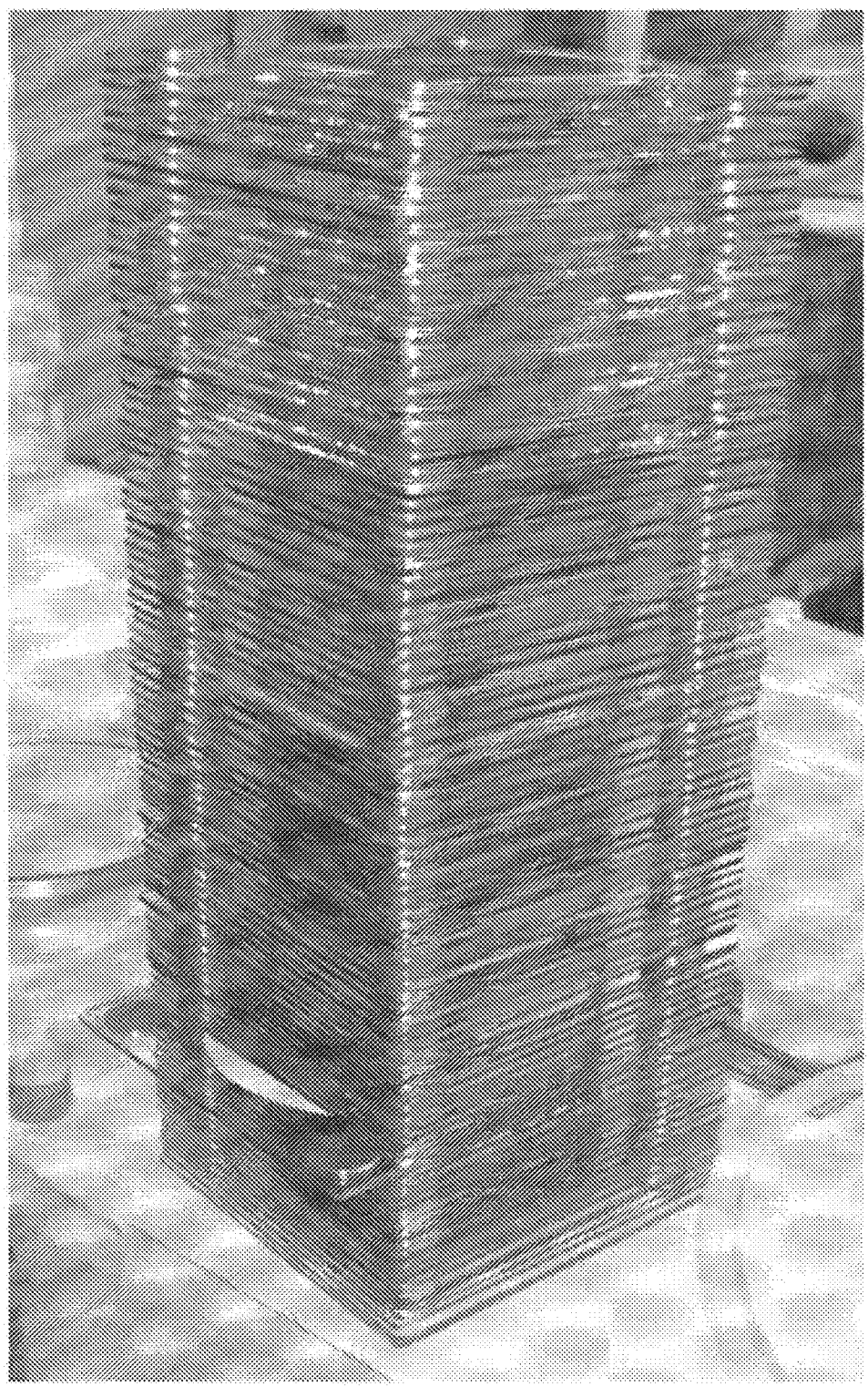
FIG. 29 illustrates a stack of molds held together with magnetic clamps (e.g., Stack of self-aligned microfluidic molds) for forming polymer micro-molded structures according to specific embodiments of the invention.

FIG. 27 illustrates operation steps of a less automated or prototype system according to specific embodiments of the invention. The 96-well plate standard allows the microfluidic system to be operated using standard techniques and equipment. For example, liquid dispensing is achieved with standard pipette mechanics, and cell culture and analysis is compatible with existing incubators and plate readers. A custom built cell loading system can be used to load the cells using air pressure as described above. The gravity driven flow culture configuration utilizes the medium level difference between the inlet and outlet well as well as engineering the fluidic resistances to achieve the desirable flow rate in nL/min regime. This provides the significant advantage of being able to "passively" flow culture medium for long periods of time (for example, up to 4 days) without the use of bulky external pumps.

Fabrication Techniques

Example 1

Figure 30:
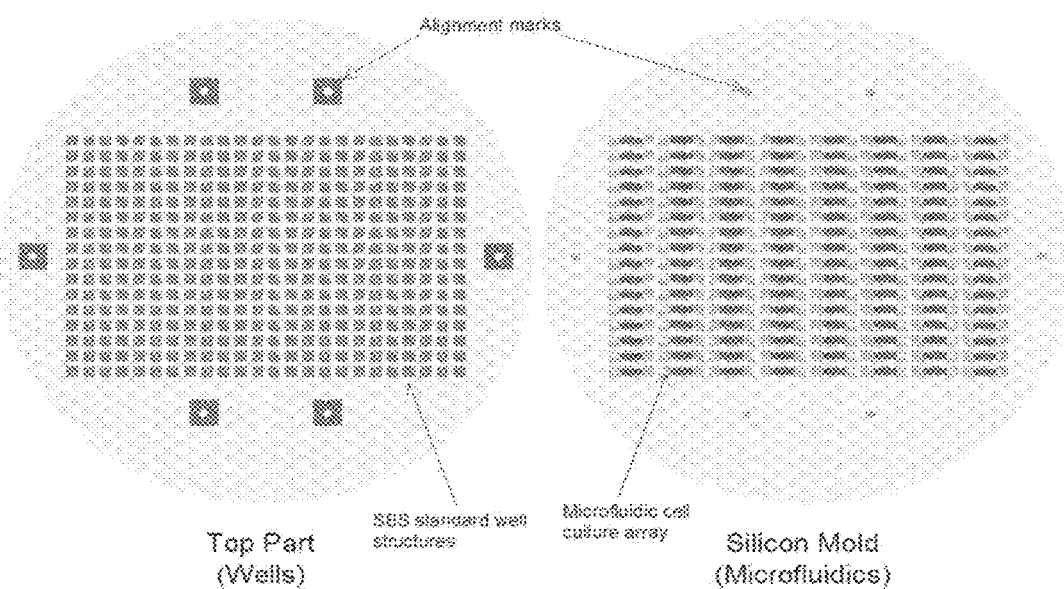
FIG. 30 is a block diagram showing an example direct soft molding process according to specific embodiments of the invention.

FIG. 30 is a block diagram illustrating two components of a direct soft molding process according to specific embodiments of the invention. The two components illustrated are: (1) An injection molded top piece made of acrylic containing at least alignment marks (to be assembled to the microfluidic mold) and well structures generally complying with standard microtiter plate formats. (Alternatively, a standard well plate may be used.) (2) A microfluidic mold fabricated using semiconductor technologies on a 6" silicon wafer containing the microfluidic cell culture arrays made of epoxy or electroplated metals, as well as the alignment marks so the well structures aligned to the microfluidic structures during the molding process. An injection molded top piece is made of acrylic or any similar suitable material and contains well structures that preferably comply with standard microtiter plate formats as will be discussed more herein. On the right is shown a microfluidic mold fabricated using any known semiconductor and/or microfabrication technologies on, for example, a 6" silicon wafer. The mold contains an impression the microfluidic cell culture arrays and can include components made of epoxy or electroplated metals, as well as the alignment marks so the well structures aligned to the microfluidic structures during the molding process. Generally, before further processing, the mold is coated with fluoropolymer to reduce stiction of the soft polymer to the mold.

Because the top piece containing the well structures is injection molded, the bottom of the wells can be flat, rounded or tapered. One particular desired feature is that the bottom of the top piece, which covers the microfluidic structures, is as flat as practically to assist uniform molding across the array. According to specific embodiments of the invention, the bottom of the top piece can be chemically or mechanically or otherwise modified or primed by a reagent (such as Sylgard Primecoat) or an abrasive surface (sanding) or laser so the soft polymers adhere to the bottom of the top piece after the molding process. This treatment of the surface is indicated by the heavy line.

Figure 31A:
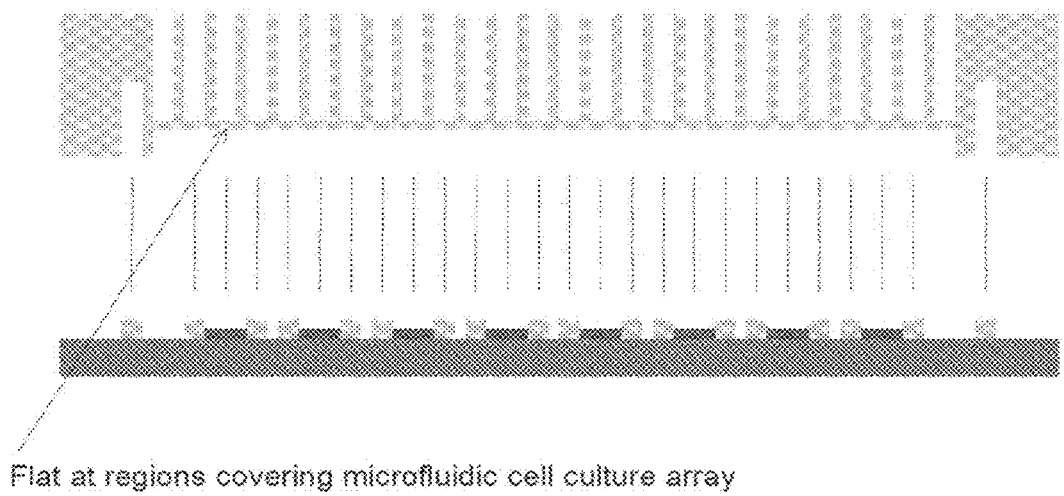
FIG. 31A illustrates the two pieces in position before mounting to glass and coating. Because the top piece is injection molded, the bottom of the wells can be flat, rounded or tapered. One particular desired feature is that the bottom of the top piece, which covers the microfluidic structures, should be flat to ensure uniform molding across the array. This top piece can be either a proprietary top piece with wells as shown or, alternatively, can be a standard SBS multi-well plate.
Figure 31B:
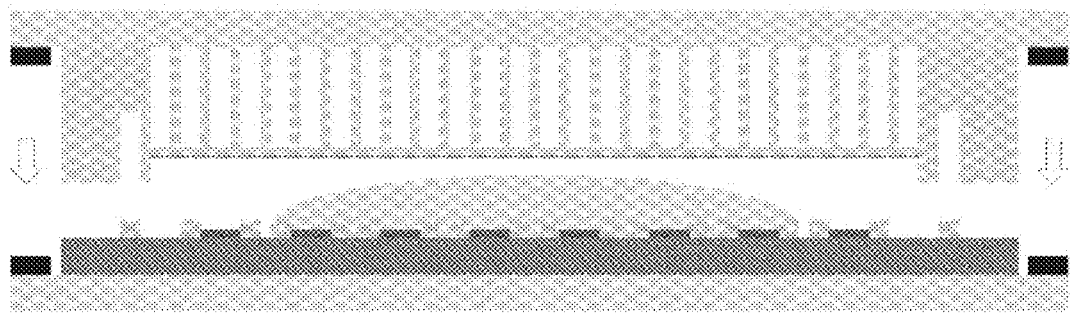
FIG. 31B illustrates an example wherein the bottom of the top piece is chemically modified by a reagent (Sylgard Primecoat) so the soft polymers adhere to the bottom of the top piece after the molding process and illustrates an appropriate amount of soft polymer poured onto the center of the mold (usually a few milliliters, depending on the area to be covered as well as the thickness of the soft polymer after molding).

FIG. 31B illustrates an example wherein an appropriate amount of soft polymer is poured onto the center of the mold (usually a few milliliters, depending on the area to be covered as well as the thickness of the soft polymer after molding). The top piece and the mold are sandwiched between two pieces of flat surfaces (usually glass plates) with clamping mechanisms (in this case, magnets).

Figure 31C:
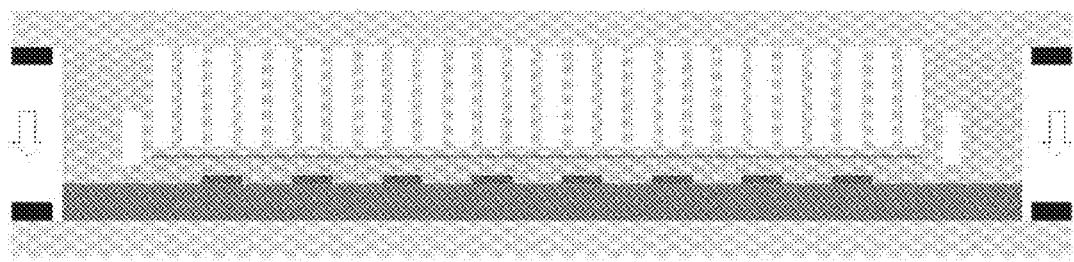
FIG. 31C illustrates an example wherein the top piece and the mold are sandwiched between two pieces of flat surfaces (usually glass plates) with clamping mechanisms (in this case, magnets) and the clamping mechanism holds the top piece and the mold together with alignment marks fitted to each other.

FIG. 31C illustrates an example wherein the clamping mechanism holds the top piece and the mold together with alignment marks fitted to each other. The soft polymer is then cured, for example by temperature or UV light of otherwise so the microfluidic cell culture array is truthfully molded onto the soft polymer. As an example, at elevated temperature (usually 60 C.) for at least 2 hours.

Figure 31D:
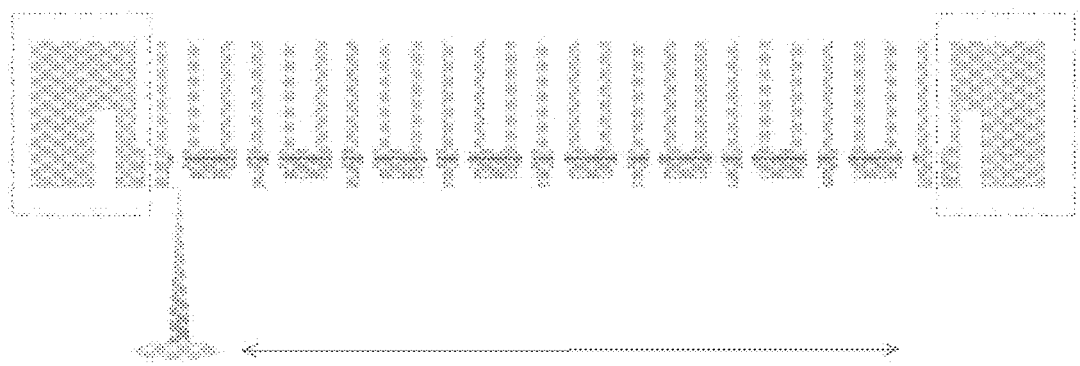
FIG. 31D illustrates an example wherein after detaching the molded microfluidic cell culture array with the top piece, a laser cutter is used to create fluidic connections between the microfluidic structures and the wells at specific locations (cell/reagent inlets/outlets).

FIG. 31D illustrates an example wherein after detaching the molded microfluidic cell culture array with the top piece, a laser cutter is used to create fluidic connections between the microfluidic structures and the wells at specific locations (cell/reagent inlets/outlets). The circular top piece is trimmed to rectangular shape at this stage. (Note that in this image, the structure is inverted.) Before enclosing the bottom of the microfluidic cell culture array, the molded piece is ultrasonically cleaned to shake off any dust created by the laser cutting step. A top piece may be trimmed to a rectangular shape at this stage. The cross section shown in through each of the fluidic connections for illustration purposes, though the laser only makes holes in the material and does not cut the wells apart. At this state, before enclosing the bottom of the microfluidic cell culture array, the molded piece is preferably ultrasonically or otherwise cleaned to shake off any dust created by the laser cutting step.

Figure 31E:
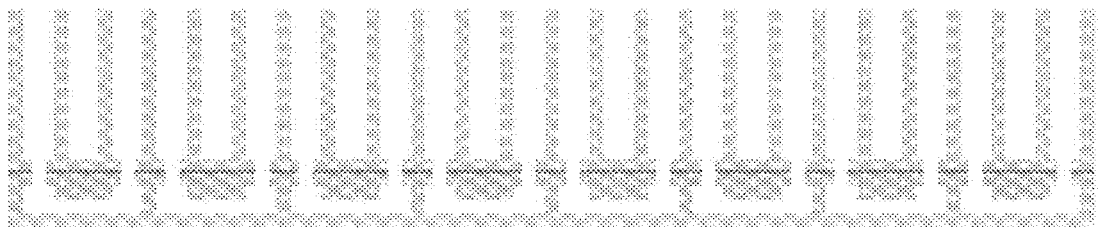
FIG. 31E illustrates an example wherein the microfluidic cell culture array is bonded to a piece of rectangular glass. The glass and/or array may be subjected to oxygen plasma treatment before the bonding.

FIG. 31E illustrates an example wherein the microfluidic cell culture array undergoes oxygen plasma treatment and is bonded to a piece of rectangular glass.

Figure 31F:
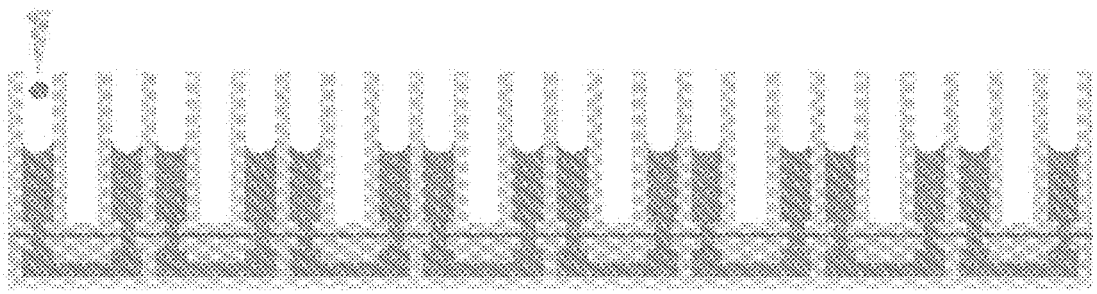
FIG. 31F illustrates an example wherein using a liquid dispenser, the microfluidic cell culture array is filled with priming solutions to maintain its modified surface chemistry. If bubbles appear to be trapped inside the array, additional vacuum steps are used to eliminate the bubbles.

FIG. 31F illustrates an example wherein using a liquid dispenser, the microfluidic cell culture array is filled with priming solutions to maintain its modified surface chemistry. If bubbles appear to be trapped inside the array, placement in a vacuum chamber may be used to eliminate the bubbles.

Figure 31G:
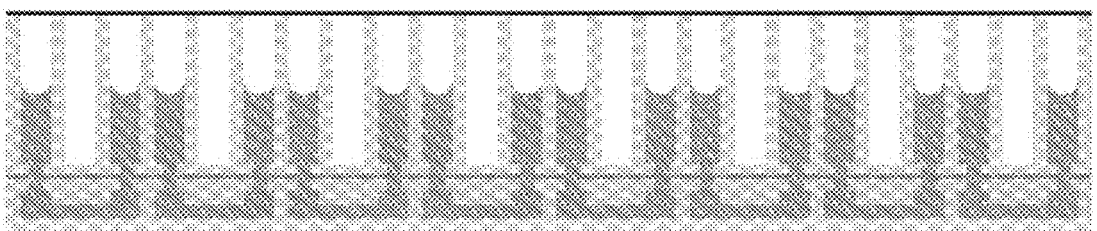
FIG. 31G illustrates an example wherein to prevent liquid evaporation, the array is sealed with a tape.
Figure 31H:
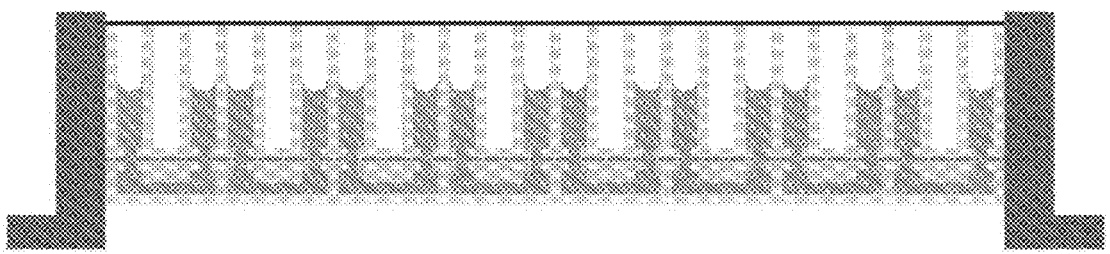
FIG. 31H illustrates an example wherein the array is optionally fit into a frame so the finished array can be treated like a standard microtiter plate with the correct outside dimensions. In the case where the top piece is a standard microtiter well plate, this step may be unnecessary.

FIG. 31G illustrates an example wherein to prevent liquid evaporation, the array is sealed with a tape. FIG. 31H illustrates an example wherein the array is fit into a frame so the finished array can be treated like a standard microtiter plate with the correct outside dimensions.

6. Example 2

Figure 32A:
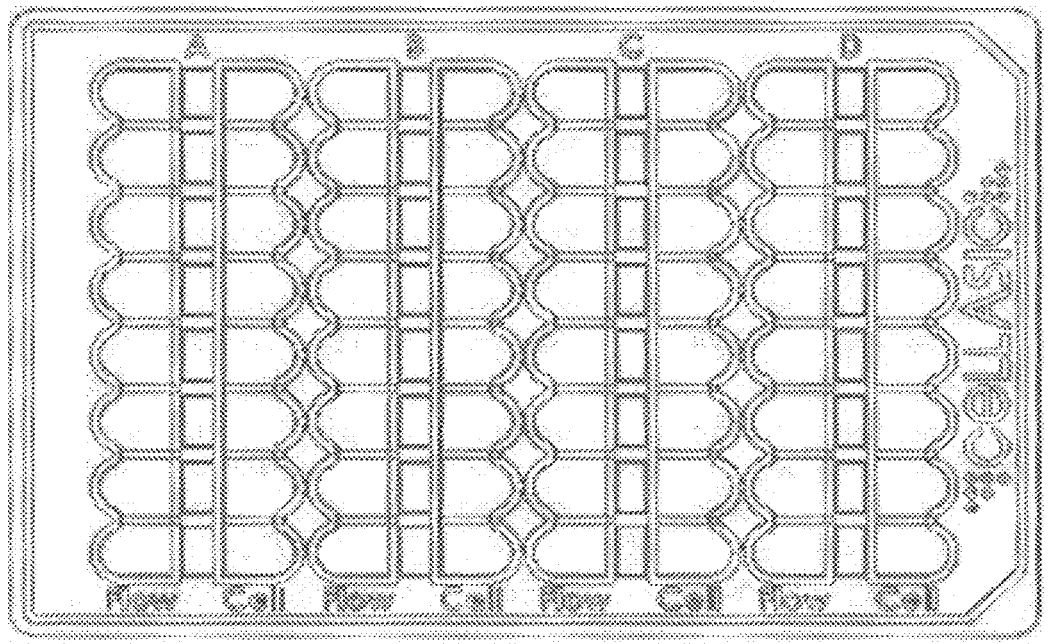
FIG. 32A-D illustrate four components of a direct soft molding process according to specific embodiments of the invention.
Figure 32B:
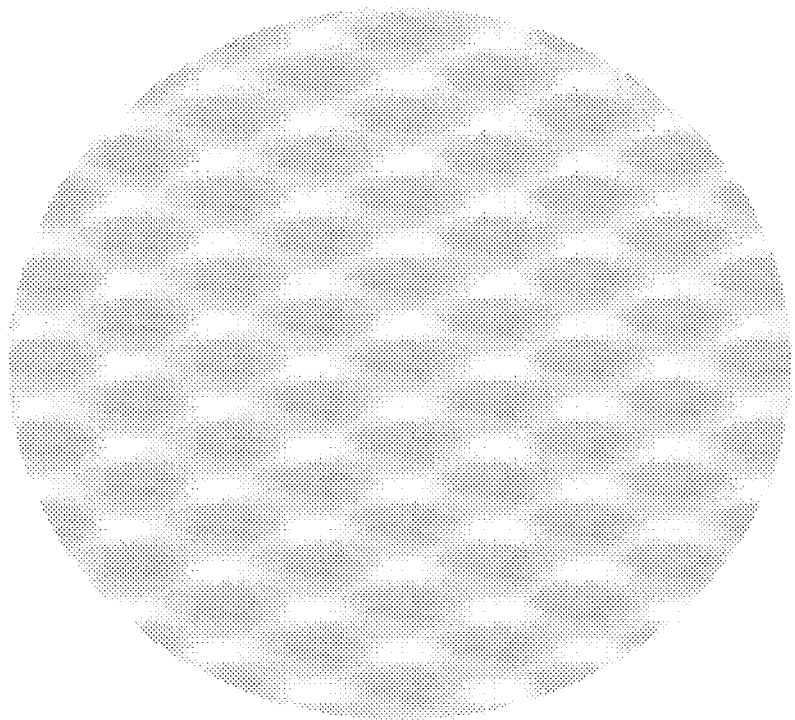
Figure 32C:
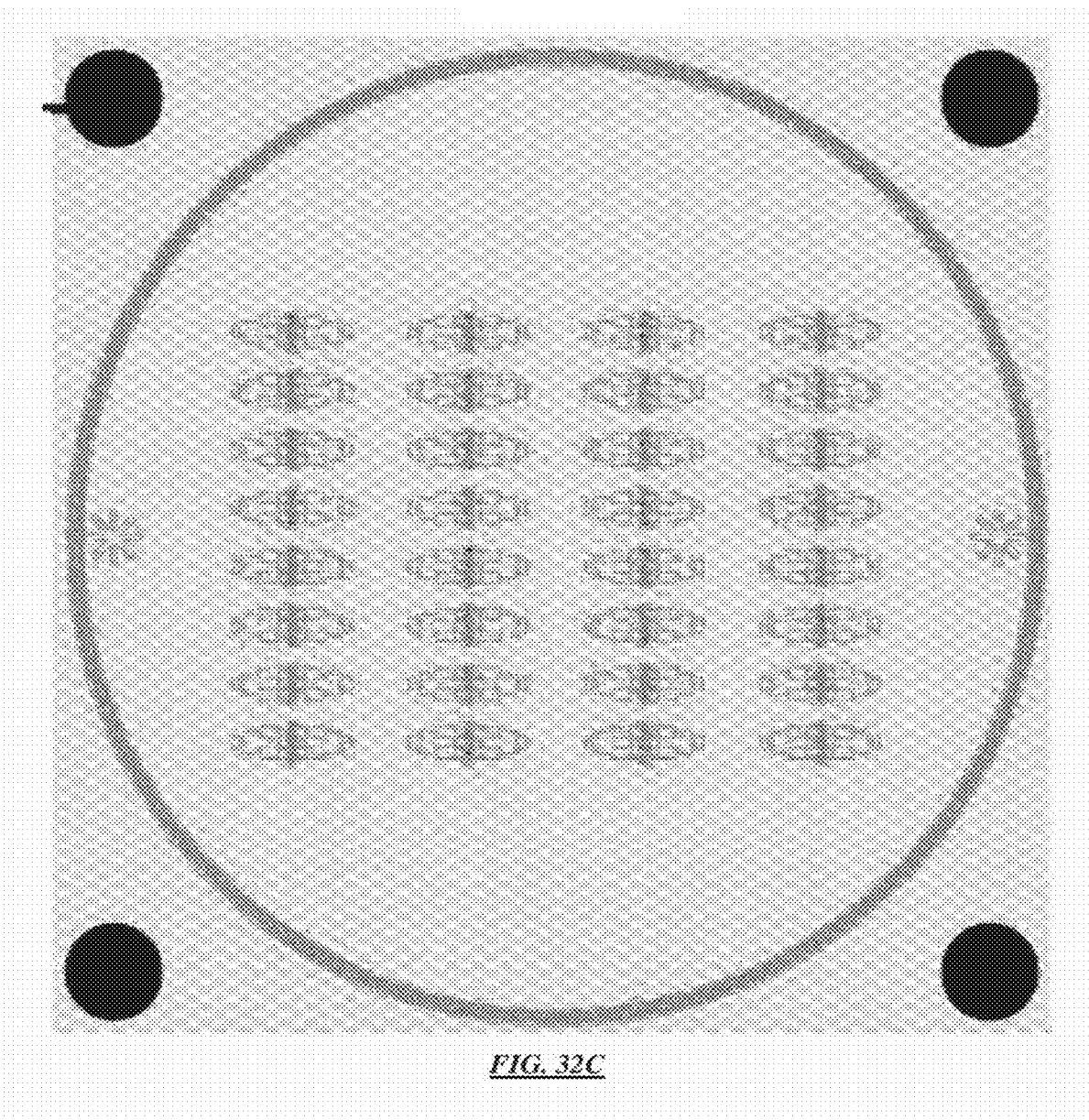

FIG. 32A-C illustrate three components of a direct soft molding process according to specific embodiments of the invention. In the figure, (A) shows an injection molded top piece that includes well structures complying with standard microtiter plate formats. As discussed above, rather than the injection molded top piece shown, a standard microtiter plate may be used as the top piece that includes well structures complying with standard microtiter plate formats, (B) Illustrates a 1.5 mm thick acrylic circular sheet (6" in diameter), and (C) illustrates a microfluidic mold fabricated on a 6" silicon wafer containing microfluidic cell culture units (in this example 8×4 units) in an arrays made of epoxy, etched silicon, or electroplated metals, as well as a spacer to control the minimum thickness of the soft polymer after molding. The mold is coated with fluoropolymer to reduce stiction of the soft polymer to the mold. As shown in the figure, the microfluidic mold is glued to a 1 mm thick soda lime glass (7"×7") with four magnets (e.g., 15 mm in diameter and 1.5 mm in thickness) glued to the four corners of the glass. The other piece of the 1 mm thick soda lime glass (7"×7") with complementary magnets is prepared in similar fashion (FIG. 32D) with the magnets of opposite polarity glued on the four corners so the magnets will self-align onto the magnets in FIG. 32C. One side of the acrylic sheet is chemically modified by a reagent (e.g., Sylgard Primecoat) to induce the strong adhesion between the acrylic and the soft polymer (e.g., Sylgard 184) to be used during the molding process.

Figures 32D, 33A:
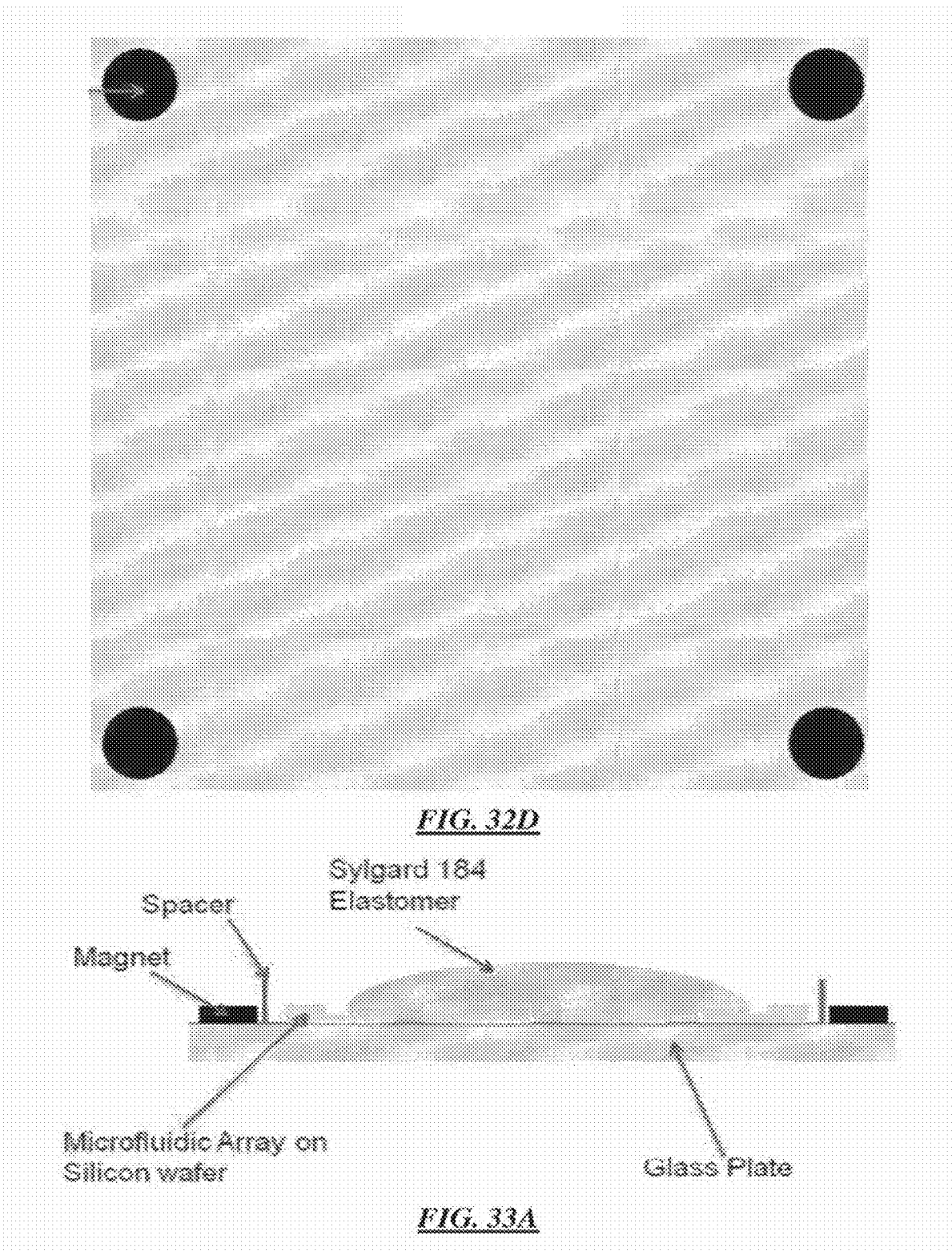
FIG. 33A illustrates a step wherein an appropriate amount of soft polymer is poured onto the center of the mold (usually a few milliliters, depending on the area to be covered as well as the spacer thickness) For example, for a mold 6" in diameter and a 150 micron spacer, the minimum amount required is $\pi \times 7.62$ cm$\times 7.62$ cm$\times 0.015$ cm~2.75 mL).

FIG. 33A illustrates a step wherein an appropriate amount of soft polymer is poured onto the center of the mold (usually a few milliliters, depending on the area to be covered as well as the spacer thickness) For example, for a mold 6" in diameter and a 150 micron spacer, the minimum amount required is π×7.62 cm×7.62 cm×0.015 cm~2.75 mL).

Figure 33B:
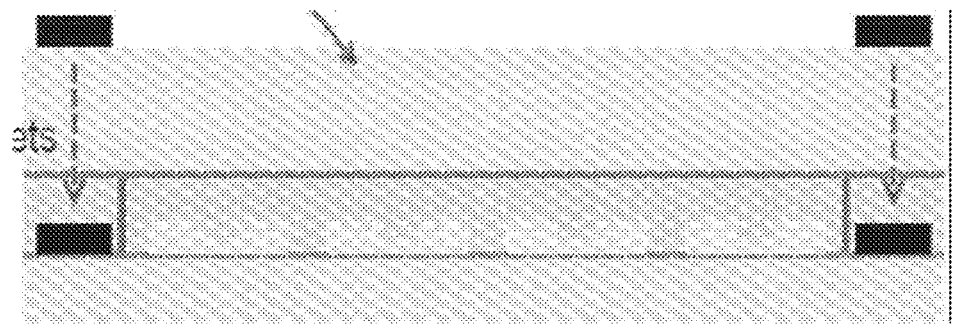
FIG. 33B illustrates a step wherein the acrylic sheet is sandwiched between two pieces of the glass plates so the magnets will press the acrylic sheet (with primer modified surface facing the mold) against the mold until the acrylic sheet hits the spacer. The soft polymer will then fill the space between the acrylic sheet and the mold to replicate the microfluidic structures. In particular embodiments, the magnet-assisted clamping mechanism holds the pieces together while the soft polymer is cured at elevated temperature (60 degree C.) for at least 2 hours.
Figure 33C:
FIG. 33C illustrates that after cooling the compartments down to approximately room temperature, the acrylic sheet with the soft polymer is detached from the mold. The microfluidic cell culture array is truthfully molded onto the soft polymer. To protect the soft polymer surface from contaminations from following processes, a surface protection tape (Ultron Blue Adhesive Plastic Film 80 micron) may be applied to the top of the surface of the elastomer by a roller.
Figure 33C:
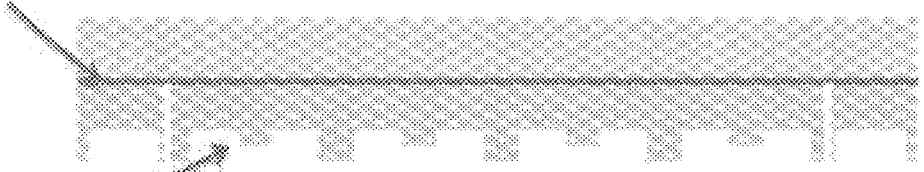
Figure 33C:
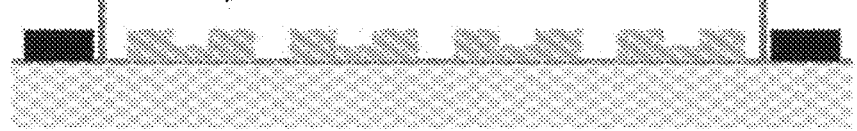

FIG. 33B illustrates a step wherein the acrylic sheet is sandwiched between two pieces of the glass plates so the magnets will press the acrylic sheet (with primer modified surface facing the mold) against the mold until the acrylic sheet hit the spacer. The soft polymer will then fill the space between the acrylic sheet and the mold to replicate the microfluidic structures. In particular embodiments, the magnet-assisted clamping mechanism holds the pieces together while the soft polymer is cured at elevated temperature (60 degree C.) for at least 2 hours.

After cooling the compartments down to approximately room temperature, the acrylic sheet with the soft polymer is detached from the mold and a microfluidic cell culture array as described herein is truthfully molded onto the soft polymer.

To protect the soft polymer surface from contaminations from following processes, a surface protection tape (e.g., Ultron Blue Adhesive Plastic Film 80 micron) is optionally applied to the top of the surface of the elastomer by a roller.

Figure 33D:
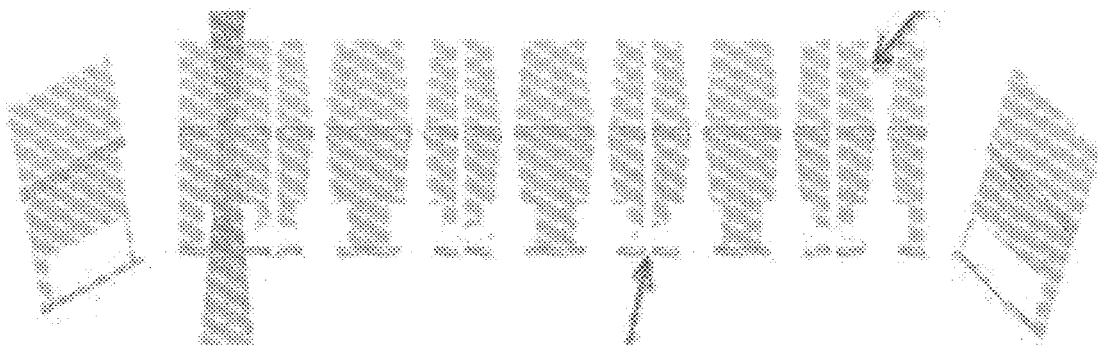
FIG. 33D illustrates that after separation from the mold a CO2 laser cutter (VersaLaser, 25W model) is used to create fluidic connections between the microfluidic structures and the injection molded wells (cell inlet and medium inlet). Since the soft polymer used in the process is gas permeable, "air holes" may be cut near the cell culture areas to promote air diffusion for better cell culture. The circular top piece is may be trimmed to rectangular shape at this stage.
Figure 33E:
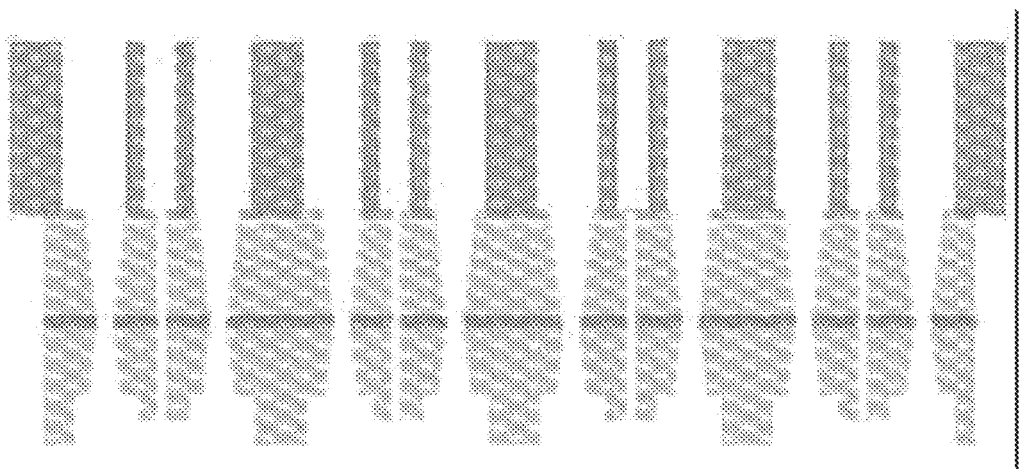
FIG. 33E illustrates that after the surface protection tape is removed and the array is optionally ultrasonically cleaned (or water-jet cleaned) to shake off any dust created by the laser cutting step and optionally a new surface protection tape is applied, the microfluidic cell culture array is glued to the injection molded plate with an ultra-violet (UV) curable glue which is also bio-compatible (Loctite 3301). The plate with the microfluidic cell culture array is cured in a UV chamber for 30 minutes. After removal of the surface protection tape, both a glass substrate (e.g., White Float Glass) and the microfluidic cell culture array undergo oxygen plasma treatment to activate the surface and the glass substrate encloses the microfluidic cell culture array through covalent bonding, as shown in FIG. 33F.
Figure 33F:
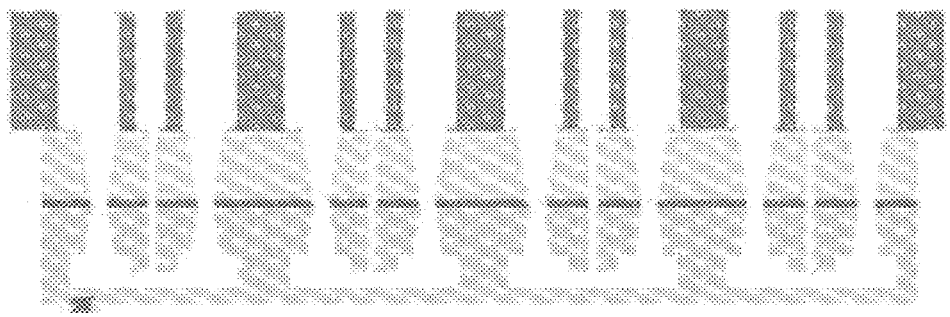
FIG. 33F illustrates the glass substrate enclosing the microfluidic cell culture array through covalent bonding.
Figure 33G:
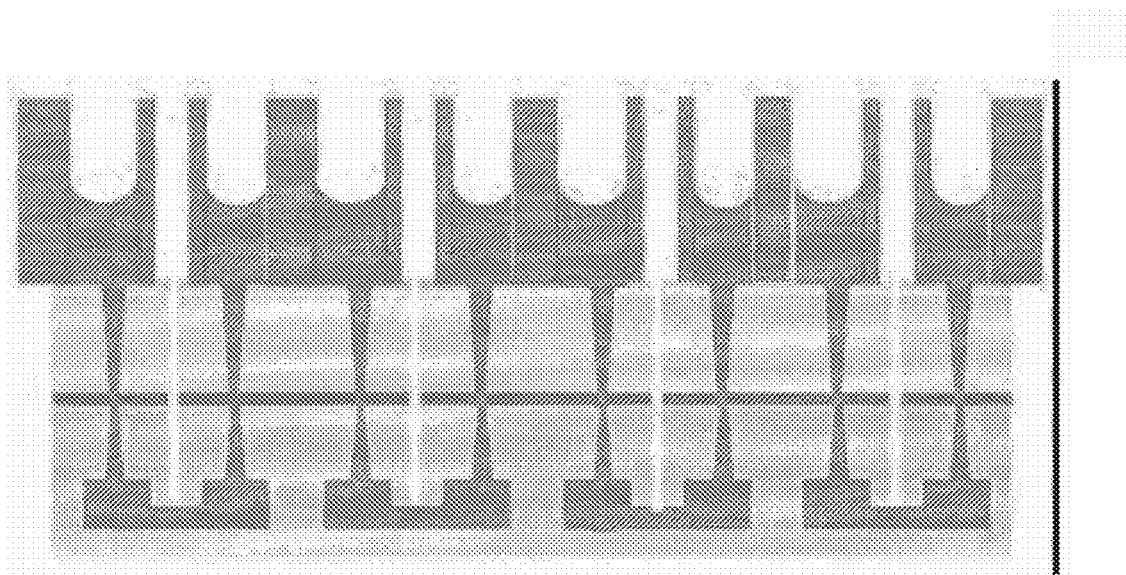
FIG. 33G illustrates that using a liquid dispenser, the microfluidic cell culture array is filled with priming solutions, as bubbles may be inside the array; and the array may be placed inside a vacuum chamber for bubbles removal and may also be placed inside a UV/Ozone chamber (Novascan) for sterilization.
Figure 33H:
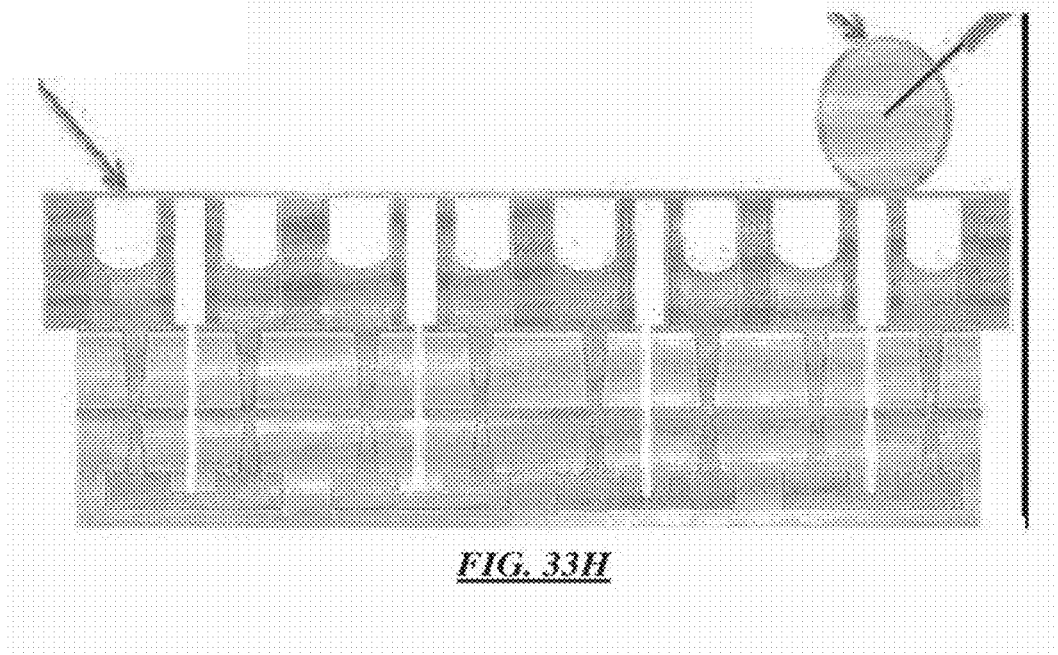
FIG. 33H illustrates that to prevent liquid evaporation, the array is sealed with a tape (Excel Scientific, AlumaSeal).

FIG. 33D illustrates a step wherein a CO2 laser cutter (VersaLaser, 25W model) is used to create fluidic connections between the microfluidic structures and the injection molded wells (cell inlet and medium inlet). Since the soft polymer used in the process is gas permeable, "air holes" are cut near the cell culture areas to promote air diffusion for better cell culture. The circular top piece may be trimmed to rectangular shape at this stage. The surface protection tape is removed and the array is ultrasonically cleaned (or water-jet cleaned) to shake off any dust created by the laser cutting step and a new surface protection tape is applied. In FIG. 33E, the microfluidic cell culture array is glued to the injection molded plate or a standard-well plate with an ultra-violet (UV) curable glue which is also bio-compatible (Loctite 3301). The plate with the microfluidic cell culture array is cured in a UV chamber for 30 minutes. After removal of the surface protection tape, both a glass substrate (White Float Glass) and the microfluidic cell culture array undergo oxygen plasma treatment to activate the surface. The glass substrate encloses the microfluidic cell culture array through covalent bonding, as shown in FIG. 33F. Using a liquid dispenser, the microfluidic cell culture array is filled with priming solutions as shown in FIG. 33G. Because bubbles may be present inside the array; the array is generally placed inside a vacuum chamber for bubbles removal. The plate may also be placed inside a UV/Ozone chamber (Novascan) for sterilization. To prevent liquid evaporation, the array is sealed with a tape (e.g., Excel Scientific, AlumaSeal) as shown in FIG. 33H.

Integrated Systems

Integrated systems for the collection and analysis of cellular and other data as well as for the compilation, storage and access of the databases of the invention, typically include a digital computer with software including an instruction set for sequence searching and/or analysis, and, optionally, one or more of high-throughput sample control software, image analysis software, collected data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises valves, concentration gradients, fluidic multiplexors and/or other microfluidic structures for interfacing to a microchamber as described.

Readily available computational hardware resources using standard operating systems can be employed and modified according to the teachings provided herein, e.g., a PC (Intel x86 or Pentium chip-compatible DOS,™ OS2,™ WINDOWS,™ WINDOWS NT,™ WINDOWS95,™ WINDOWS98,™ LINUX, or even Macintosh, Sun or PCs will suffice) for use in the integrated systems of the invention. Current art in software technology is adequate to allow implementation of the methods taught herein on a computer system. Thus, in specific embodiments, the present invention can comprise a set of logic instructions (either software, or hardware encoded instructions) for performing one or more of the methods as taught herein. For example, software for providing the data and/or statistical analysis can be constructed by one of skill using a standard programming language such as Visual Basic, Fortran, Basic, Java, or the like. Such software can also be constructed utilizing a variety of statistical programming languages, toolkits, or libraries.

FIG. 34 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

Various programming methods and algorithms, including genetic algorithms and neural networks, can be used to perform aspects of the data collection, correlation, and storage functions, as well as other desirable functions, as described herein. In addition, digital or analog systems such as digital or analog computer systems can control a variety of other functions such as the display and/or control of input and output files. Software for performing the electrical analysis methods of the invention are also included in the computer systems of the invention.

Other Embodiments

Although the present invention has been described in terms of various specific embodiments, it is not intended that the invention be limited to these embodiments. Modification within the spirit of the invention will be apparent to those skilled in the art.

It is understood that the examples and embodiments described herein are for illustrative purposes and that various modifications or changes in light thereof will be suggested by the teachings herein to persons skilled in the art and are to be included within the spirit and purview of this application and scope of the claims.

All publications, patents, and patent applications cited herein or filed with this submission, including any references filed as part of an Information Disclosure Statement, are incorporated by reference in their entirety.

What is claimed:

1. A microfluidic cell culture system integrated into a standard well plate, the microfluidic cell culture system comprising:
a medium inlet reservoir fluidically connected to a plurality of microfluidic medium channels; a plurality of cell culture areas each located at an end of a cell culture channel;
said cell culture channel having a cell inlet opening fluidically connected to a cell inlet/medium outlet reservoir for introducing cells to said plurality of cell culture areas and for removing media;
a first well in communication with the medium inlet reservoir acting as a medium inlet; a second well in communication with the cell inlet/medium outlet reservoir acting as a cell inlet/medium outlet;
a third well acting as a viewing well for the plurality of cell culture areas;
a perfusion barrier between said plurality of cell culture areas and said plurality of microfluidic medium channels, said perfusion barrier containing a plurality of perfusion passages;
such that fluid introduced into said medium inlet reservoir must pass through said perfusion barrier before reaching said cell inlet/medium outlet reservoir; wherein a plurality of said perfusion passages are substantially narrower than cells to be cultured.

2. The system of claim 1, further comprising robotic equipment and wherein, the standard well plate is capable of being handled by the robotic equipment allowing for automated cell culture and analysis, said robotic equipment being in part equipment designed for use with standard well plates.

3. The system of claim 1, further wherein said cell culture channels include a first portion near said cell inlet that contains solid walls with no perfusion passages, thereby to prevent cell adhesion.

4. The system of claim 1, further wherein said cell culture channels include a first portion near said cell inlet that contains solid walls with no perfusion passages, thereby to prevent cell adhesion and include a second portion nearer to said cell inlet than said first portion, said second portion having a plurality of perfusion passages to facilitate media flow out of said cell culture region.

5. The system of claim 1, further wherein:
said plurality of cell culture areas are separated into at least three blocks, each block containing at least two cell culture areas;
each block having an air channel adjacent thereto.

6. The system of claim 1, further wherein:
the device is configured so that cells are introduced into said cell culture areas using pneumatic pressure, and thereafter, cells are maintained by perfusion of media using a passive gravity driven fluid flow.

7. The system of claim 1, further comprising:
a large fluidic opening directly connected to said cell culture channels to allow for easier cell flow.

8. The system of claim 1, further comprising:
a fluidic multiplexor connecting said media inlet reservoir to said microfluidic medium channels;
and further wherein a plurality of said cell culture channels comprise a cell culture area with perfusion passages to said media channels and a non perfusion cell channel portion for better localizing cells introduced under pneumatic pressure and an outlet portion with perfusion passages near to an inlet of said cell culture channel.

9. The system of claim 1, further wherein:
said plurality of cell culture areas are elongated areas mimetic of a liver sinusoid;
said plurality of cell culture areas are loaded with cells from said cell inlet reservoir;
after cell loading and settling, media is loaded from said media inlet and removed from said cell inlet/medium outlet reservoir.

10. A method of culturing cells using the system of claim 1, comprising:
placing cells into a well of a standard well plate, said well in communication with the cell inlet/medium outlet reservoir;
placing media into a different well of said standard well plate, said well in communication with the medium inlet reservoir;
allowing said cells to culture for an appropriate time;
observing and/or assaying cells and or media in said standard well plate.

11. The method of claim 10, further comprising:
interfacing said standard well plate with a pneumatic manifold for providing air pressure to drive said cells into said cell culture areas, said pneumatic manifold providing sufficient pressure to form cell aggregates in said cell culture areas.

12. The method of claim 11, further wherein said pneumatic manifold interfaces with said well plate using a vacuum seal.

13. The method of claim 11, further comprising:
using a pipette to introduce and/or remove fluids from said reservoirs, said fluids passively perfusing through said plurality of cell culture areas as a result of gravity and/or differential fluid levels; and or surface tensions.

14. The method of claim 10, further wherein said steps are performed by fully automated robotic equipment and further wherein said combination of pneumatic cell loading and passive perfusion allows simultaneous automatic culture of a large number of plates using one pneumatic manifold and one automated pipettor because plates do not need to be attached to any equipment during perfusion fluid flow.

15. The system of claim 1, further comprising a pneumatic manifold, the standard well plate further capable of being pneumatically coupled with the pneumatic manifold, said manifold providing pneumatic pressure to drive cells into said plurality of cell culture areas.

* * * * *